United States Patent
Schäfer et al.

(10) Patent No.: US 9,362,510 B2
(45) Date of Patent: Jun. 7, 2016

(54) ELECTROLUMINESCENT METAL COMPLEXES WITH BENZOTRIAZOLES

(75) Inventors: Thomas Schäfer, Liestal (CH); Peter Murer, Oberwil (CH); Gisèle Baudin, Allschwil (CH); Manuela Kocher, Sisseln (CH); François Maike, Gelspitzen (FR); Stephan Allenbach, Sisseln (CH); Rosemarie Sift, Freiburg-Tiengen (DE); Beat Schmidhalter, Bubendorf (CH)

(73) Assignee: BASF SE, Ludwigshafen (DE)

( * ) Notice: Subject to any disclaimer, the term of this patent is extended or adjusted under 35 U.S.C. 154(b) by 400 days.

(21) Appl. No.: 12/527,437

(22) PCT Filed: Feb. 13, 2008

(86) PCT No.: PCT/EP2008/051702
§ 371 (c)(1),
(2), (4) Date: Aug. 17, 2009

(87) PCT Pub. No.: WO2008/101842
PCT Pub. Date: Aug. 28, 2008

(65) Prior Publication Data
US 2010/0108994 A1 May 6, 2010

(30) Foreign Application Priority Data
Feb. 23, 2007 (EP) .................................... 07102949

(51) Int. Cl.
*H01L 51/54* (2006.01)
*C09K 11/06* (2006.01)
*H01L 51/00* (2006.01)
*C07F 15/00* (2006.01)
*H01L 51/50* (2006.01)

(52) U.S. Cl.
CPC ........ *H01L 51/0085* (2013.01); *C07F 15/0033* (2013.01); *C07F 15/0086* (2013.01); *C09K 11/06* (2013.01); *H01L 51/0087* (2013.01); *C09K 2211/1059* (2013.01); *C09K 2211/185* (2013.01); *H01L 51/006* (2013.01); *H01L 51/0081* (2013.01); *H01L 51/5016* (2013.01)

(58) Field of Classification Search
CPC ........... C09K 11/06; C09K 2211/1059; C09K 2211/185; C09K 2211/188; C07F 15/0033; C07F 15/006; C07F 15/0073; C07F 15/0086; C07F 13/00; H01L 51/0084; H01L 51/0085; H01L 51/0087; H01L 51/5016
See application file for complete search history.

(56) References Cited

U.S. PATENT DOCUMENTS

| | | |
|---|---|---|
| 5,247,190 A | 9/1993 | Friend et al. |
| 5,408,109 A | 4/1995 | Heeger et al. |
| 5,486,406 A | 1/1996 | Shi |
| 5,552,678 A | 9/1996 | Tang et al. |
| 2001/0019782 A1 | 9/2001 | Igarashi et al. |
| 2002/0055014 A1 | 5/2002 | Okada et al. |
| 2006/0202197 A1 | 9/2006 | Nakayama et al. |
| 2006/0287498 A1 | 12/2006 | Morishita et al. |
| 2007/0009759 A1 | 1/2007 | Burn et al. |
| 2008/0015355 A1 | 1/2008 | Schafer et al. |

FOREIGN PATENT DOCUMENTS

| | | |
|---|---|---|
| EP | 443861 | 8/1991 |
| EP | 710655 A1 | 5/1996 |
| GB | 2423518 A | 8/2006 |
| WO | 2004/101707 A1 | 11/2004 |
| WO | 2006000544 A | 1/2006 |

OTHER PUBLICATIONS

O'Brien et al., Improved energy transfer in electrophosphorescent devices, Appl. Phys. Lett. vol. 74 No. 3 (1999).
Djurovich et al., Ir(III) Cyrlometalated Complexes as Efficient Phosphorescent Emitters in Polymer Blend and Organic LEDs, Polymer Preprints 41(1), 770 (2000).
J.A.C. Allison et al., Chloropalladation of 2-Phenyl-1,2,3-triazoles as a Means of Selective o-Chlorination, Department of Chemistry and Chemical Engineering, Michigan Technological University, 1275-1277 (1975).
Nonoyama et al., Palladium (II), Platinum (II), Rhodium (III) and Iridium (III) Complexes Coordinated with 2-Aryl-4,5-dimethyl-1,2,3-triazoles as Bidentate Nitrogen—Carbon Chelate Ligands, Transition Met. Chem. 3, 366-369 (1978).

(Continued)

*Primary Examiner* — Marie R. Yamnitzky
(74) *Attorney, Agent, or Firm* — Shruti Costales

(57) ABSTRACT

This invention relates to electroluminescent metal complexes with benzotriazoles of the formula (I), a process for their preparation, electronic devices comprising the metal complexes and their use in electronic devices, especially organic light emitting diodes (OLEDs), as oxygen sensitive indicators, as phosphorescent indicators in bioassays, and as catalysts.

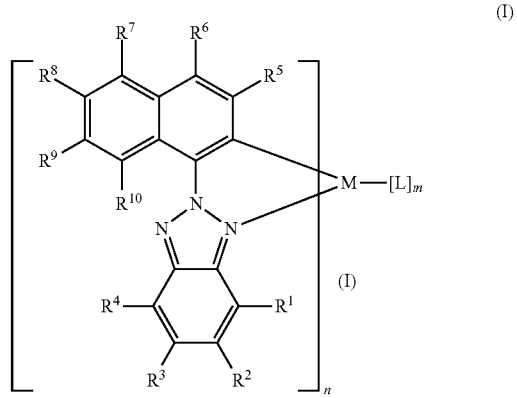

6 Claims, No Drawings

(56) References Cited

OTHER PUBLICATIONS

Huang et al., Highly Phosphorescent Bis-Cyclometalated Iridium Complexes Containing Benzoimidazole-Based Ligands, Chem. Mater. 16, 2480-2488 (2004).
Patent abstracts of Japan Pub. No. 2005029783, (Feb. 2005).
Patent abstracts of Japan Pub. No. 2005023072, (Jan. 2005).
Patent abstracts of Japan Pub. No. 2005023071, (Jan. 2005).
Patent abstracts of Japan Pub. No. 2005023070, (Jan. 2005).
Patent abstracts of Japan Pub. No. 2005029784, (Feb. 2005).
Patent abstracts of Japan Pub. No. 2005029782, (Feb. 2005).

ELECTROLUMINESCENT METAL COMPLEXES WITH BENZOTRIAZOLES

This invention relates to electroluminescent metal complexes with benzotriazoles, a process for their preparation, electronic devices comprising the metal complexes and their use in electronic devices, especially organic light emitting diodes (OLEDs), as oxygen sensitive indicators, as phosphorescent indicators in bioassays, and as catalysts.

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, in U.S. Pat. No. 5,247,190, U.S. Pat. No. 5,408,109 and EP-A-443 861. Complexes of 8-hydroxyquinolate with trivalent metal ions, particularly aluminum, have been extensively used as electroluminescent components, as has been disclosed in, for example, U.S. Pat. No. 5,552,678.

Burrows and Thompson have reported that fac-tris(2-phenylpyridine) iridium can be used as the active component in organic light-emitting devices. (Appl. Phys. Lett. 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-$C^{i2}$,N]iridium(III). (Polymer Preprints 2000, 41(1), 770.)

J. A. C. Allison et al., J. Heterocyclic Chem. 12 (1975) 1275-1277 discloses 2-phenyl-1,2,3-triazole chloro complexes of palladium and their use as catalysts in the synthesis of chlorinated phenyl triazines.

M. Nonoyama and C. Hayata, Transition Met. Chem. 3 (1978) 366-369 describe cyclometallations of 2-aryl-4,5-dimethyl-1,2,3-triazoles [H(C—N)] with palladium(II), platinum(II), rhodium(III) and iridium(III)chloride which results in [MCl(C—N)]$_2$ for M=Pd, or Pt and [MCl(C—N)$_2$]$_2$ species for M=Rh, or Ir. These complexes react with monodentate ligands, L, such as pyridine and tri-n-butylphosphine to give MCl(C—N)L and MCl(C—N)$_2$L complexes US20020055014 relates to a light-emitting device comprising a phosphorescent compound. Preferred phosphorescent compounds include compounds having a partial structure represented by the formula shown below

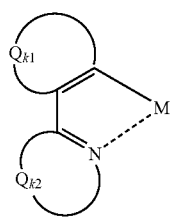

wherein M represents a transition metal; $Q_{k1}$ represents an atomic group necessary for forming a 5- or 6-membered aromatic ring; and $Q_{k2}$ represents an atomic group necessary for forming a 5- or 6-membered aromatic azole ring. The 5- or 6-membered aromatic azole ring completed by $Q_{k2}$ may include triazole.

US20010019782 discloses a light-emitting material comprising a compound having a partial structure represented by the following formula

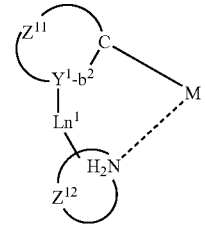

wherein $Z^{11}$ and $Z^{12}$ each represent a nonmetallic atom group required to form a 5- or 6-membered ring with at least one of carbon atom and nitrogen atom, said ring optionally having a substituent or forming a condensed ring with the other ring; $Ln^1$ represents a divalent group; $Y^1$ represents a nitrogen atom or carbon atom; and $b^2$ represents a single bond or double bond. Among the preferred examples of the 5- or 6-membered ring formed by $Z^{11}$ and $Z^{12}$ are 1,2,3-triazole rings, and 1,2,4-triazole rings. The divalent group $Ln^1$ does not comprise a single bond.

Phosphorescent bis-cyclometalated iridium complexes containing benzoimidazole-based ligands are described by W.-S. Huang et al. in Chem. Mater. 16 (2004) 2480-2488.

WO06/000544 relates to electroluminescent metal complexes with triazoles and benzotriazoles, a process for their preparation, electronic devices comprising the metal complexes and their use in electronic devices, especially organic light emitting diodes (OLEDs), as oxygen sensitive indicators, as phosphorescent indicators in bioassays, and as catalysts.

JP2005023070, JP2005023071, JP2005023072, JP2005029782, JP2005029783, JP2005029784 and US2006/0287498 disclose metal coordination compounds comprising benzotriazole based ligands. The metal coordination compounds are distinguished from the compounds of formula I according to the present invention by the group bonded to the nitrogen atom of the benzotriazole backbone, which is not derived from 1-naphthyl.

However, there is a continuing need for electroluminescent compounds, especially orange, or red emitters, having improved efficiency.

Accordingly the present invention is directed to compounds (metal complexes) of the formula

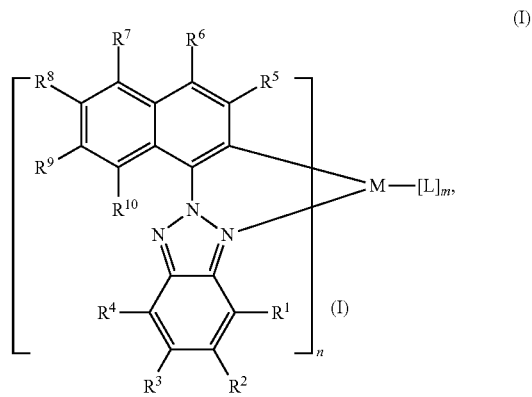

$R^1$ to $R^{10}$ are independently of each other hydrogen, an organic substituent, or fluorine, or two substituents $R^1$ to $R^{10}$ which are adjacent to each other, together form a ring, L is a mono-, or bi-dentate ligand, n is an integer 1 to 3, m is 0, an integer 1 to 4 depending on the ligand and the metal, and M is a metal with an atomic weight of greater than 40, especially Fe, Ru, Ni, Co, Ir, Pt, Pd, Rh, Re, or Os, very especially Ir, or Pt, a process for their preparation, electronic devices comprising the metal complexes and their use in electronic devices, especially organic light emitting diodes (OLEDs), as oxygen sensitive indicators, as phosphorescent indicators in bioassays, and as catalysts.

The compounds of the present invention are preferably orange, or red emitters having a $\lambda_{max}$ above about 520 nm, especially above about 560 nm and very especially above about 600 nm. The 2H-benzotriazole compound or compounds should have a NTSC coordinate of between about (0.62, 0.37) and about (0.68, 0.32), especially a NTSC coordinate of between about (0.64, 0.35) and about (0.68, 0.32), very especially a NTSC coordinate of about (0.67, 0.33) or (0.68, 0.32).

According to the present invention the metal complex comprise at least a 2H-benzotriazole ligand, i.e. it may comprise two or three or more 2H-benzotriazole ligands.

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one triangular face of the octahedron. The term "meridional" is intended to mean one isomer of a complex, $Ma_3b_3$, having octahedral geometry, in which the three "a" groups occupy three positions such that two are trans to each other, i.e. the three "a" groups sit in three coplanar positions, forming an arc across the coordination sphere that can be thought of as a meridian. The phrase "adjacent to" when used to refer to layers in a device, does not necessarily mean that one layer is immediately next to another layer. The term "photoactive" refers to any material that exhibits electroluminescence and/or photosensitivity.

The metal complexes of the present invention are characterized in that at least one ligand is derived from a benzotriazole compound. Suitable benzotriazoles are known or can be produced according to known procedures. The synthesis of suitable benzotriazoles is, for example, described in WO03/105538, and WO05/054212 as well as the references cited therein.

The metal is generally a metal M with an atomic weight of greater than 40, Preferably the metal M is selected from the group consisting of Fe, Ru, Ni, Co, Ir, Pt, Pd, Rh, Re, Os, Tl, Pb, Bi, In, Sn, Sb, Te, Ag and Au. More preferably the metal M is selected from Ir, Rh and Re as well as Pt and Pd, wherein Ir is most preferred.

$R^1$, $R^2$, $R^3$ and $R^4$ are independently of each other hydrogen, CN, fluorine, $C_1$-$C_{24}$alkyl, $C_1$-$C_{24}$alkoxy, $C_1$-$C_{24}$alkylthio, $C_1$-$C_{24}$ perfluoroalkyl, $C_6$-$C_{18}$aryl, which is optionally substituted by G; —$NR^{25}R^{26}$, —$CONR^{25}R^{26}$, —$COOR^{27}$, or —$COR^{28}$; or $C_2$-$C_{10}$heteroaryl, which is optionally substituted by G; or $R^1$ and $R^2$, $R^2$ and $R^3$, $R^3$ and $R^4$, $R^5$ and $R^6$, $R^7$ and $R^8$, $R^8$ and $R^9$, $R^9$ and $R^{10}$ are a group of formula

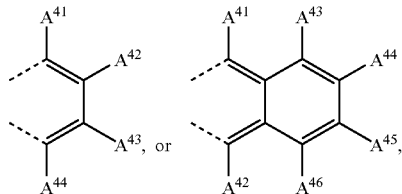

or $R^6$ and $R^7$ are a group of formula

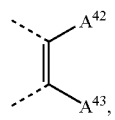

wherein $A^{41}$, $A^{42}$, $A^{43}$, $A^{44}$, $A^{45}$, and $A^{46}$ are independently of each other H, halogen, CN, $C_1$-$C_{24}$alkyl, $C_1$-$C_{24}$ perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl; especially

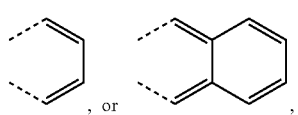

wherein $R^{25}$ and $R^{26}$ are independently of each other $C_6$-$C_{18}$aryl, $C_6$-$C_{18}$aryl which is substituted by $C_1$-$C_{18}$alkyl or $C_1$-$C_{18}$alkoxy; $C_1$-$C_{24}$alkoxy which is interrupted by —O—, or —$NR^{25'}$—, $C_7$-$C_{18}$aralkyl, or $C_1$-$C_{24}$alkyl, $R^{27}$ and $R^{28}$ are independently of each other $C_1$-$C_{24}$alkyl, $C_6$-$C_{18}$aryl, or $C_7$-$C_{18}$aralkyl, which may optionally be substituted by $C_1$-$C_{18}$alkyl or $C_1$-$C_{18}$alkoxy;

$R^5$ is hydrogen, fluorine, $C_1$-$C_{24}$alkyl, CN, $C_1$-$C_{24}$alkyl, which is substituted by F, $C_6$-$C_{18}$-aryl, $C_6$-$C_{18}$-aryl which is substituted by $C_1$-$C_{12}$alkyl, $C_1$-$C_{18}$alkoxy, or $C_2$-$C_{18}$heteroaryl, $R^6$ is hydrogen, CN, halogen, especially F, $C_1$-$C_{24}$alkyl, which may be substituted by F, $C_1$-$C_{24}$alkoxy; $C_1$-$C_{24}$alkoxy which is interrupted by —O—, or —$NR^{25}$—, $C_6$-$C_{18}$aryl, $C_6$-$C_{18}$aryl which is substituted by $C_1$-$C_{12}$alkyl, $C_2$-$C_{18}$heteroaryl, or $C_1$-$C_8$alkoxy, —$NR^{25}R^{26}$, —$CONR^{25}R^{26}$, —$COOR^{27}$, or

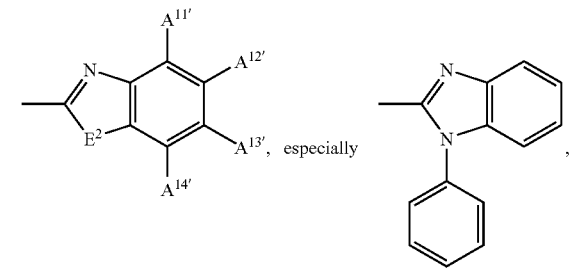

wherein
E² is —S—, —O—, or —NR²⁵'—, wherein R²⁵' is $C_1$-$C_{24}$alkyl, or $C_6$-$C_{10}$aryl, or $R^5$ and $R^6$ are a group of formula

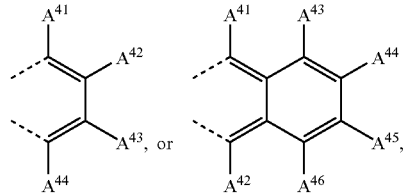

wherein $A^{41}$, $A^{42}$, $A^{43}$, $A^{44}$, $A^{45}$, and $A^{46}$ are as defined above, $A^{11'}$, $A^{12'}$, $A^{13'}$, and $A^{14'}$ are independently of each other H, halogen, CN, $C_1$-$C_{24}$alkyl, $C_1$-$C_{24}$alkoxy, $C_1$-$C_{24}$alkylthio, —NR²⁵R²⁶, —CONR²⁵R²⁶, or —COOR²⁷, $R^7$, $R^8$, $R^9$, and $R^{10}$ are independently of each other H, halogen, especially F, CN, $C_1$-$C_{24}$alkyl, $C_2$-$C_{18}$-hereroaryl, or $C_6$-$C_{10}$aryl, which may be substituted by $C_1$-$C_{18}$alkyl, or $C_1$-$C_{18}$alkoxy, $C_1$-$C_{24}$alkoxy, $C_1$-$C_{24}$alkoxy which is interrupted by —O—, or —NR²⁵—, $C_1$-$C_{24}$alkylthio, —NR²⁵R²⁶, —CONR²⁵R²⁶, or —COOR²⁷, wherein R²⁵, R²⁶ and R²⁷ are as defined above and G is $C_1$-$C_{18}$alkyl, —OR³⁰⁵, —SR³⁰⁵, —NR³⁰⁵R³⁰⁶, —CONR³⁰⁵R³⁰⁶, or —CN, wherein R³⁰⁵ and R³⁰⁶ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or R³⁰⁵ and R³⁰⁶ together form a five or six membered ring, in particular

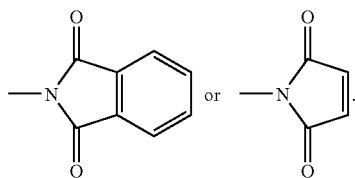

$R^5$ is preferably hydrogen, or $C_1$-$C_{24}$alkyl, $C_6$-$C_{18}$aryl, $C_6$-$C_{18}$aryl which is substituted by $C_1$-$C_{18}$alkyl, or $C_1$-$C_{18}$alkoxy; or fluorine; most preferably hydrogen, $C_6$-$C_{18}$aryl, or $C_6$-$C_{18}$aryl which is substituted by $C_1$-$C_6$alkyl, or $C_1$-$C_6$alkoxy. Among hydrogen, $C_6$-$C_{18}$aryl, and $C_6$-$C_{18}$aryl hydrogen is most preferred.

$R^6$ is preferably hydrogen, $C_1$-$C_{24}$alkyl, such as methyl, ethyl, or n-butyl, $C_1$-$C_{18}$alkoxy, such as methoxy, ethoxy, n-propoxy, iso-propoxy, n-butoxy, 2-butoxy, iso-butoxy, or 2-ethylhexyloxy, $C_6$-$C_{18}$-aryl, $C_6$-$C_{18}$-aryl which is substituted by $C_1$-$C_{18}$alkyl, or $C_1$-$C_{18}$alkoxy, —NR²⁵R²⁶, or fluorine; most preferable hydrogen, $C_6$-$C_{18}$aryl, $C_6$-$C_{18}$aryl which is substituted by $C_1$-$C_6$alkyl, or $C_1$-$C_6$alkoxy, or —NR²⁵R²⁶, wherein R²⁵ and R²⁶ are independently of each other $C_1$-$C_{18}$alkyl, or $C_6$-$C_{18}$aryl which may be substituted by $C_1$-$C_6$alkyl, or $C_1$-$C_6$alkoxy, such as —NR²⁵R²⁶, wherein R²⁵ and R²⁶ are methyl, R²⁵ and R²⁶ are phenyl, or R²⁵ is phenyl and R²⁶ naphthyl.

$R^7$, $R^8$, $R^9$, and $R^{10}$ are preferably hydrogen, $C_1$-$C_{24}$alkyl, $C_6$-$C_{18}$aryl, $C_6$-$C_{18}$aryl which is substituted by $C_1$-$C_{18}$alkyl, or $C_1$-$C_{18}$alkoxy, —NR²⁵R²⁶, or fluorine; most preferably hydrogen, $C_6$-$C_{18}$-aryl, $C_6$-$C_{18}$-aryl which is substituted by $C_1$-$C_6$alkyl, or $C_1$-$C_6$alkoxy, or $R^5$ and $R^6$ are a group of formula

Compounds of formula I are preferred, wherein $R^2$ and $R^3$ are H, $CF_3$, CN, or fluorine, $R^6$ is H, $C_1$-$C_{24}$alkyl, such as methyl, ethyl, or n-butyl, $C_1$-$C_{18}$alkoxy, such as methoxy, ethoxy, n-propoxy, iso-propoxy, n-butoxy, 2-butoxy, iso-butoxy, or 2-ethylhexyloxy, NR²⁵R²⁶, wherein R²⁵ and R²⁶ are $C_1$-$C_{18}$alkyl, or $C_6$-$C_{18}$aryl, such as phenyl, or naphthyl which may be substituted by $C_1$-$C_8$alkyl, or $C_1$-$C_8$alkoxy.

M is Pd, Rh, or Re, especially Pt, or Ir,

L is a bidentate ligand, m is 0, or 1, and n is 1, or 2, if M is Pd, or Pt, m is 0, 1, or 2, and n is 1, 2, or 3, if M is Rh, Ir or Re, and $R^1$, $R^4$, $R^5$, $R^7$, $R^8$, $R^9$ and $R^{10}$ are hydrogen.

Monodentate ligands are preferably monoanionic. Such ligands can have O or S as coordinating atoms, with coordinating groups such as alkoxide, carboxylate, thiocarboxylate, dithiocarboxylate, sulfonate, thiolate, carbamate, dithiocarbamate, thiocarbazone anions, sulfonamide anions, and the like. In some cases, ligands such as β-enolates can act as monodentate ligands. The monodentate ligand can also be a coordinating anion such as halide, nitrate, sulfate, hexahaloantimonate, and the like. Examples of suitable monodentate ligands are shown below:

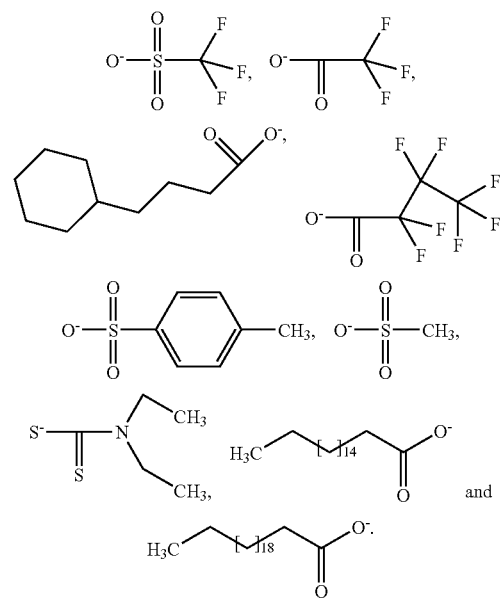

The monodentate ligands are generally available commercially.

Among the compounds of formula I compounds having a structure (Va), (Vb), (Vc); (VIa), (VIb), (VIc); (VIIa), (VIIb); (VIIIa), or (VIIIb) below are more preferred:

(Va)
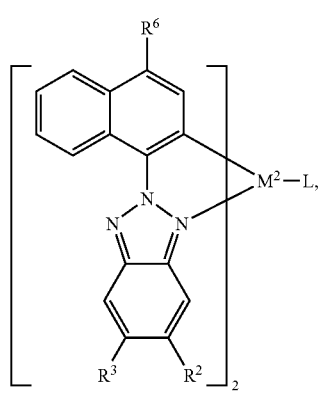
(Vb)
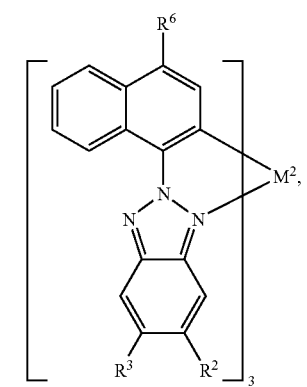
(Vc)
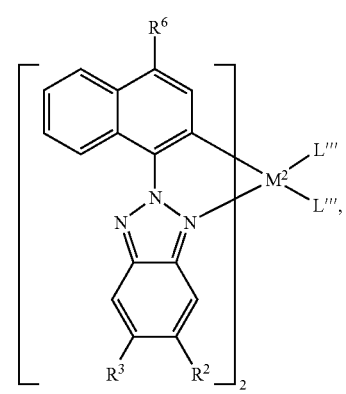
(VIa)
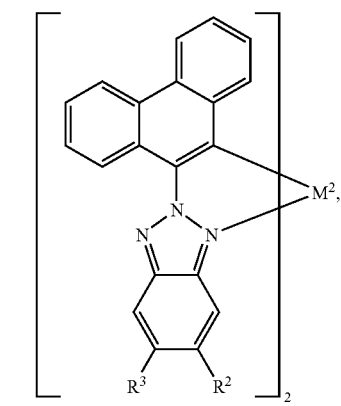
(VIb)
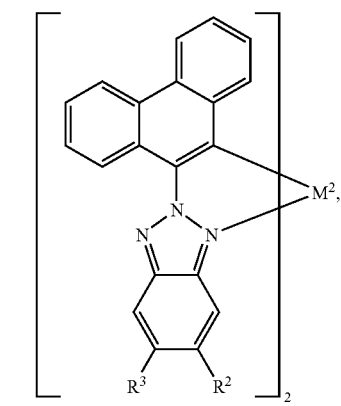
(VIc)
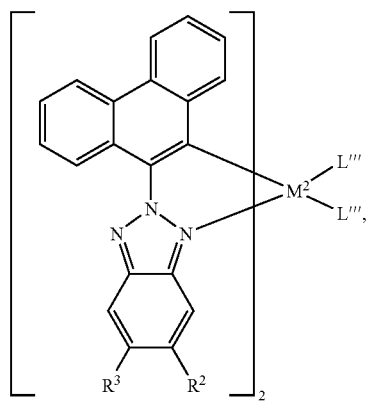
(VIIa)
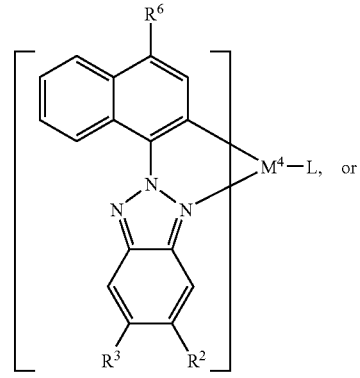
(VIIb)
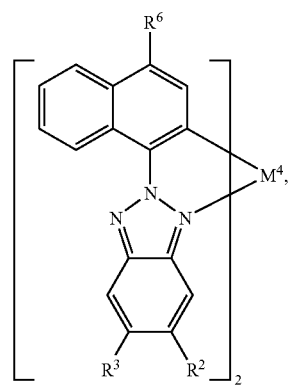

-continued

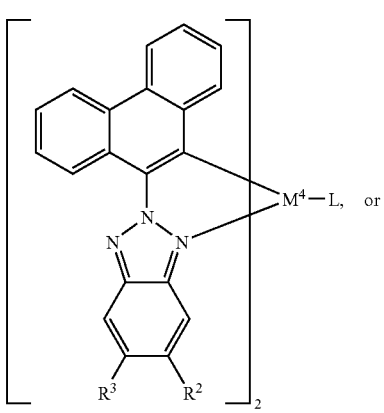
(VIIIa)

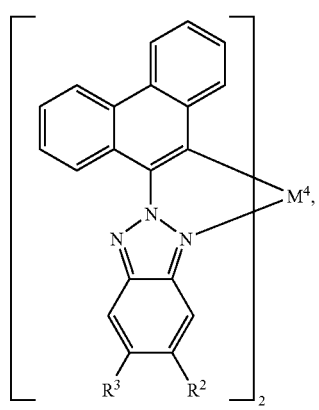
(VIIIb)

wherein

M² is Rh, or Re, especially Ir,

R² and R³ are independently of each other H, $C_1$-$C_8$alkyl, $C_1$-$C_8$ perfluoroalkyl, especially $CF_3$, or CN, R⁶ is H, —NR²⁵R²⁶, or $C_1$-$C_{18}$alkoxy, wherein R²⁵ and R²⁶ are independently of each other $C_1$-$C_{18}$alkyl, or $C_6$-$C_{10}$aryl, especially phenyl, which may be substituted by one, or more groups $C_1$-$C_{18}$alkoxy, or $C_1$-$C_{18}$alkyl, L is a bidentate ligand, and L''' is a monodentate ligand, and M⁴ is Pd, especially Pt.

Most preferred are compounds of formula Va and Vb which show orange or red luminescence. Of particular interest are compounds of formula Va, wherein M² is Ir, R² and R³ are H, or one of R² and R³ is $C_1$-$C_8$alkyl, or $C_1$-$C_8$ perfluoroalkyl, especially $CF_3$, and the other is H, R⁶ is H, or $C_1$-$C_{18}$alkoxy, and L is

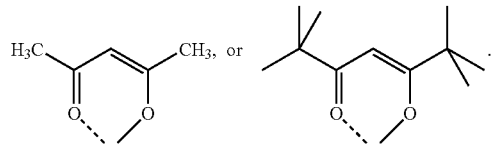

In a preferred embodiment of the present invention the ligand is a (monoanionic) bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).

Examples of such bidentate ligands L are

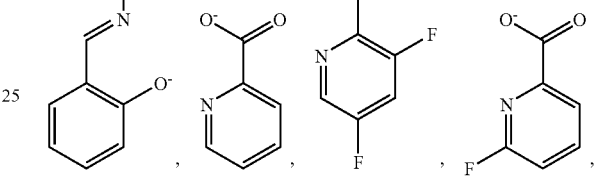

(US2004/0001970)

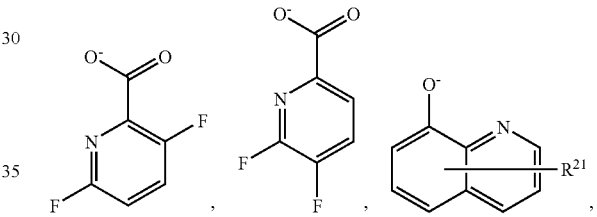

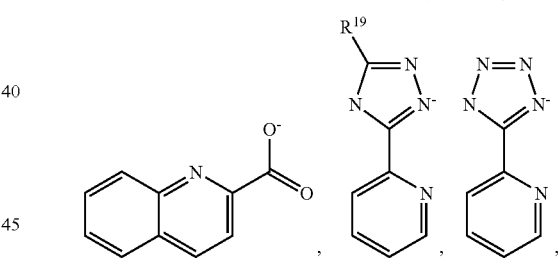

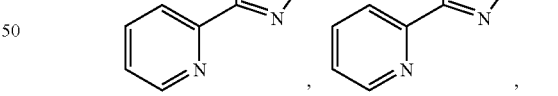

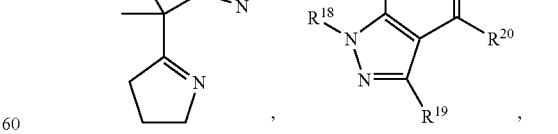

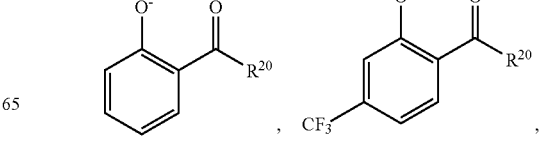

-continued
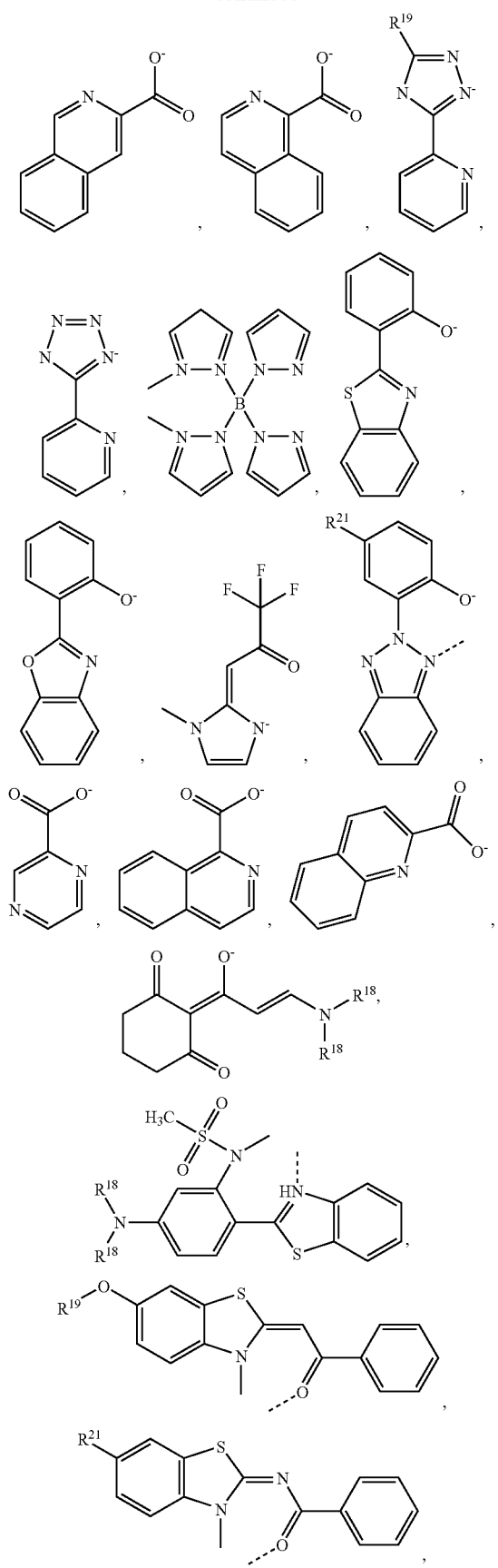
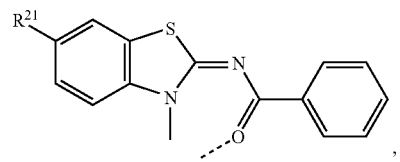
-continued
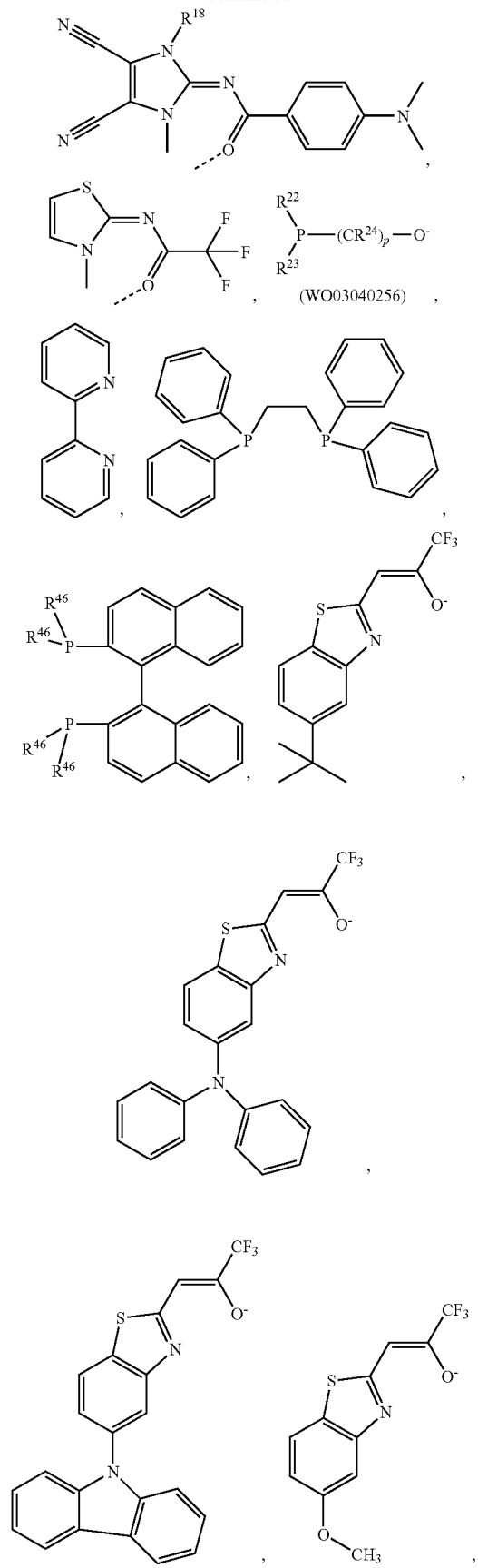

-continued

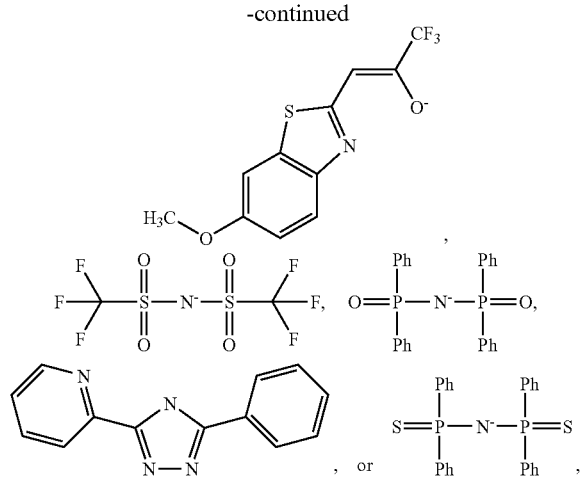

wherein $R^{11}$ and $R^{15}$ are independently of each other hydrogen, $C_1$-$C_8$alkyl, $C_6$-$C_{18}$aryl, $C_2$-$C_{10}$heteroaryl, or $C_1$-$C_8$perfluoroalkyl, $R^{12}$ and $R^{16}$ are independently of each other hydrogen, $C_6$-$C_{18}$aryl, or $C_1$-$C_8$alkyl, and $R^{13}$ and $R^{17}$ are independently of each other hydrogen, $C_1$-$C_8$alkyl, $C_6$-$C_{18}$aryl, $C_2$-$C_{10}$heteroaryl, $C_1$-$C_8$ perfluoroalkyl, or $C_1$-$C_8$alkoxy, and $R^{14}$ is $C_1$-$C_8$alkyl, $C_6$-$C_{10}$aryl, or $C_7$-$C_{11}$aralkyl, $R^{18}$ is $C_6$-$C_{10}$aryl, $R^{19}$ is $C_1$-$C_8$alkyl, $C_1$-$C_8$ perfluoroalkyl, $R^{20}$ is $C_1$-$C_8$alkyl, or $C_6$-$C_{10}$aryl, $R^{21}$ is hydrogen, $C_1$-$C_8$alkyl, or $C_1$-$C_8$alkoxy, which may be partially or fully fluorinated, $R^{22}$ and $R^{23}$ are independently of each other $C_q(H+F)_{2q+1}$, or $C_6(H+F)_5$, $R^{24}$ can be the same or different at each occurrence and is selected from H, or $C_q(H+F)_{2q+1}$, q is an integer of 1 to 24, p is 2, or 3, and $R^{46}$ is $C_1$-$C_8$alkyl, $C_6$-$C_{18}$aryl, or $C_6$-$C_{18}$aryl, which is substituted by $C_1$-$C_8$alkyl.

Examples of suitable phosphino alkoxide ligands

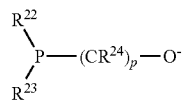

(WO03040256) are listed below:

3-(diphenylphosphino)-1-oxypropane [dppO]

1,1-bis(trifluoromethyl)-2-(diphenylphosphino)-ethoxide [tfmdpeO].

Examples of particularly suitable compounds HL,

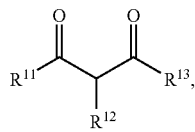

from which the ligands L are derived, include

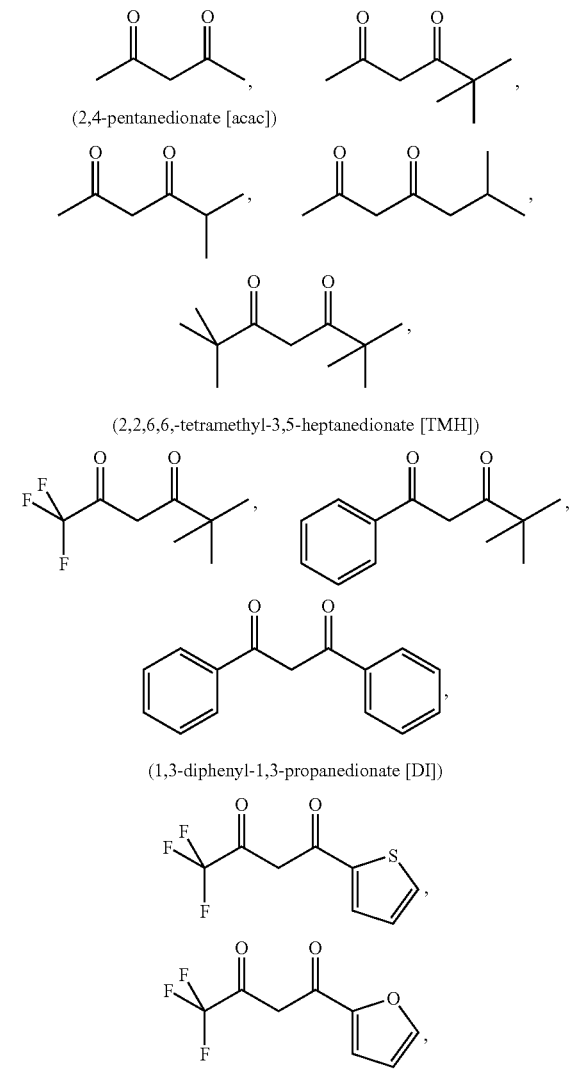

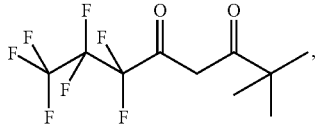

(1,1,1,3,5,5,5-heptafluoro-2,4-pentanedionate [F7acac])

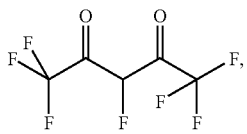

(1,1,1,5,5,5-hexafluoro-2,4-pentanedionate [F6acac])

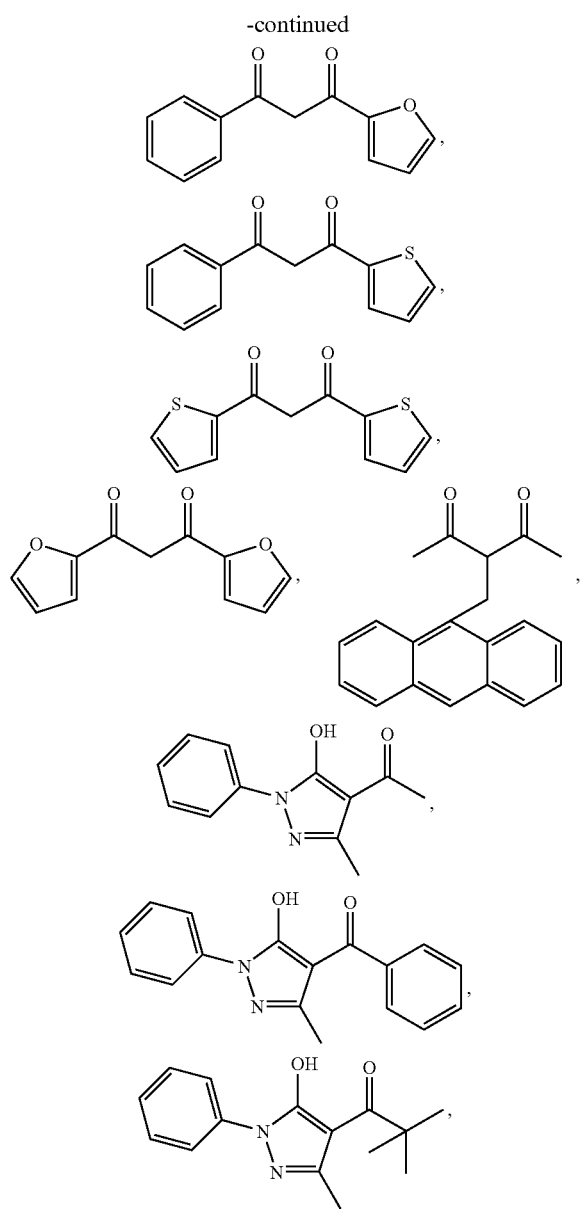

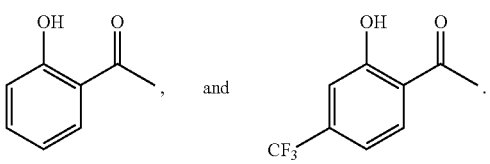

(1-phenyl-3-methyl-4-i-butyryl-pyrazolinonate [FMBP])

The hydroxyquinoline parent compounds, HL, can be substituted with groups such as alkyl or alkoxy groups which may be partially or fully fluorinated. In general, these compounds are commercially available. Examples of suitable hydroxyquinolinate ligands, L, include:

8-hydroxyquinolinate [8hq]

2-methyl-8-hydroxyquinolinate [Me-8hq]

10-hydroxybenzoquinolinate [10-hbq]

In a further embodiment of the present invention the bidentate ligand L is a ligand of formula

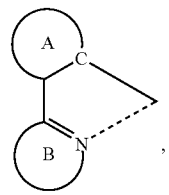

wherein the ring A,

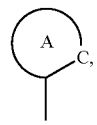

represents an optionally substituted aryl group which can optionally contain heteroatoms, the ring B,

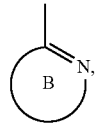

represents an optionally substituted nitrogen containing aryl group, which can optionally contain further heteroatoms, or the ring A may be taken with the ring B binding to the ring A to form a ring.

The preferred ring A includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like.

In said embodiment the bidentate ligand

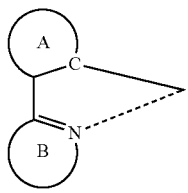

is preferably a group of formula

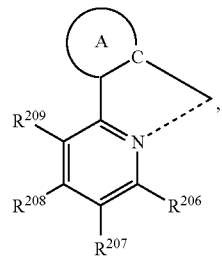

wherein $R^{206}$, $R^{207}$, $R^{208}$, and $R^{209}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{206}$, $R^{207}$, $R^{208}$, and $R^{209}$ may be substituted; or $R^{208}$ and $R^{209}$ or $R^{207}$ and $R^{208}$ are a group of formula

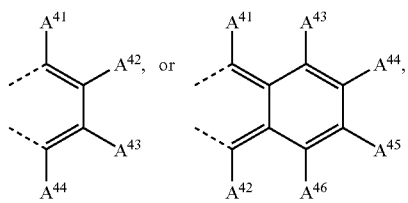

wherein $A^{41}$, $A^{42}$, $A^{43}$, $A^{44}$, $A^{45}$ and $A^{46}$ are as defined above.

Examples of preferred classes of such bidentate ligands L are compounds of the formula

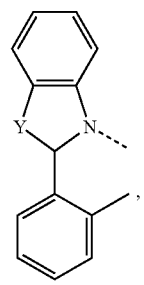 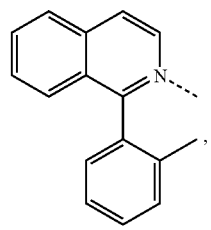 or

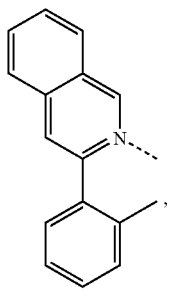 especially 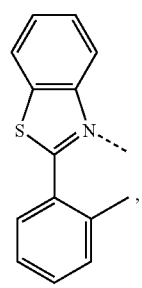, or

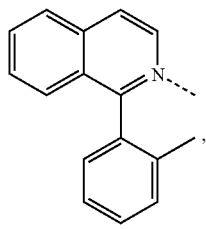, wherein Y is S, O, $NR^{200}$, wherein $R^{200}$ is $C_1$-$C_4$alkyl, $C_2$-$C_4$alkenyl, optionally substituted $C_6$-$C_{10}$aryl, especially phenyl, —$(CH_2)_r$—Ar, wherein Ar is an optionally substituted $C_6$-$C_{10}$aryl, especially

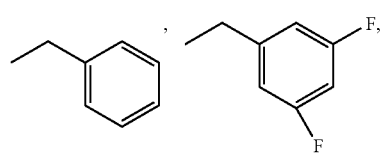

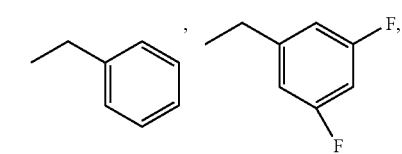

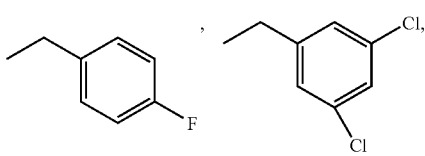

a group —$(CH_2)_{r'}X^{20}$, wherein r' is an integer of 1 to 5, $X^{20}$ is halogen, especially F, or Cl; hydroxy, cyano, —O—$C_1$-$C_4$alkyl, di($C_1$-$C_4$alkyl)amino, amino, or cyano; a group —$(CH_2)_r OC(O)(CH_2)_{r''}CH_3$, wherein r is 1, or 2, and r'' is 0, or 1;

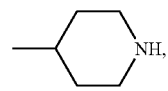

—NH-Ph, —$C(O)CH_3$, —$CH_2$—O—$(CH_2)_2$—$Si(CH_3)_3$, or

Another preferred class of ligands L is described in WO06/000544, of which the following can advantageously be used according to the present invention:

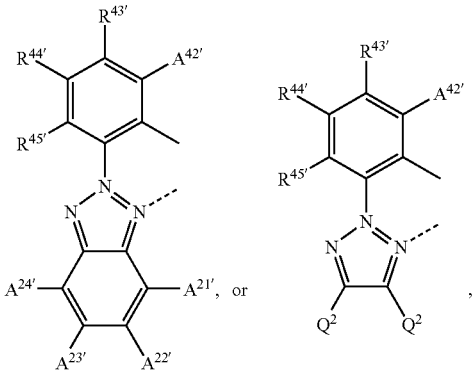

wherein $Q^1$ and $Q^2$ are independently of each other hydrogen, $C_1$-$C_{24}$alkyl, or $C_6$-$C_{18}$aryl, $A^{21'}$ is hydrogen, $A^{22'}$ is hydrogen, or $C_6$-$C_{10}$aryl, $A^{23'}$ is hydrogen, or $C_6$-$C_{10}$aryl, $A^{24'}$ is hydrogen, or $A^{23'}$ and $A^{24'}$, or $A^{23'}$ and $A^{24'}$ together form a group

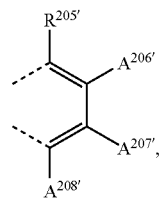

wherein $R^{205'}$, $R^{206'}$, $R^{207'}$ and $R^{208'}$ are independently of each other H, or $C_1$-$C_8$alkyl, $R^{42'}$ is H, F, $C_1$-$C_4$alkyl, $C_1$-$C_8$alkoxy, or $C_1$-$C_4$ perfluoroalkyl, $R^{43'}$ is H, F, $C_1$-$C_4$alkyl, $C_1$-$C_8$alkoxy, $C_1$-$C_4$ perfluoroalkyl, or $C_6$-$C_{10}$aryl, $R^{44'}$ is H, F, $C_1$-$C_4$alkyl, $C_1$-$C_8$alkoxy, or $C_1$-$C_4$ perfluoroalkyl, and $R^{45'}$ is H, F, $C_1$-$C_4$alkyl, $C_1$-$C_8$alkoxy, or $C_1$-$C_4$ perfluoroalkyl.

Another preferred class of bidentate ligands L is a compound of formula

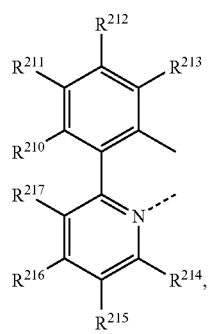

wherein $R^{214}$ is hydrogen, halogen, especially F, or Cl; $C_1$-$C_4$alkyl, $C_1$-$C_4$perfluoroalkyl, $C_1$-$C_4$alkoxy, or optionally substituted $C_6$-$C_{10}$aryl, especially phenyl, $R^{215}$ is hydrogen, halogen, especially F, or Cl; $C_1$-$C_4$alkyl, $C_1$-$C_4$ perfluoroalkyl, optionally substituted $C_6$-$C_{10}$aryl, especially phenyl, or optionally substituted $C_6$-$C_{10}$perfluoroaryl, especially $C_6F_5$, $R^{216}$ is hydrogen, $C_1$-$C_4$alkyl, $C_1$-$C_4$ perfluoroalkyl, optionally substituted $C_6$-$C_{10}$aryl, especially phenyl, or optionally substituted $C_6$-$C_{10}$perfluoroaryl, especially $C_6F_5$, $R^{217}$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $R^{210}$ is hydrogen, $R^{211}$ is hydrogen, halogen, especially F, or Cl; nitro, cyano, $C_1$-$C_4$alkyl, $C_1$-$C_4$alkoxy, $C_2$-$C_4$alkenyl, $C_1$-$C_4$ perfluoroalkyl, —O—$C_1$-$C_4$ perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $R^{212}$ is hydrogen, halogen, especially F, or Cl; nitro, hydroxy, mercapto, amino, $C_1$-$C_4$alkyl, $C_2$-$C_4$alkenyl, $C_1$-$C_4$ perfluoroalkyl, $C_1$-$C_4$alkoxy, —O—$C_1$-$C_4$ perfluoroalkyl, —S—$C_1$-$C_4$alkyl, tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, and $R^{213}$ is hydrogen, nitro, cyano, $C_1$-$C_4$alkyl, $C_2$-$C_4$alkenyl, $C_1$-$C_4$ perfluoroalkyl, —O—$C_1$-$C_4$perfluoroalkyl, tri($C_1$-$C_4$alkyl)silanyl, or optionally substituted $C_6$-$C_{10}$aryl, especially phenyl.

Specific examples of bidentate ligands L are the following compounds (X-1) to (X-57):

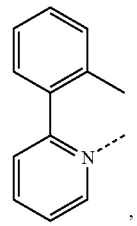
(X-1)

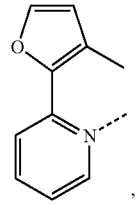
(X-2)

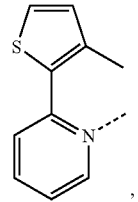
(X-3)

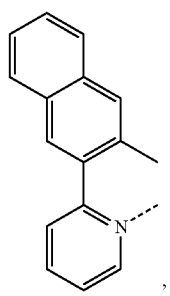 (X-4),
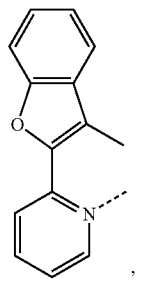 (X-5),
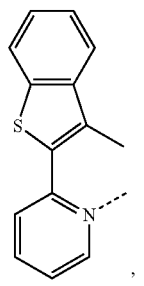 (X-6),
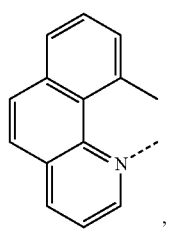 (X-7),
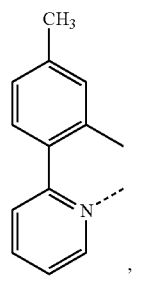 (X-8),
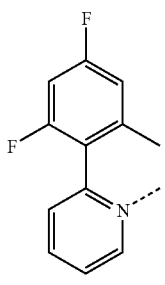 (X-9),
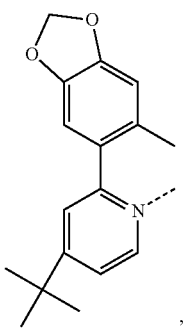 (X-10),
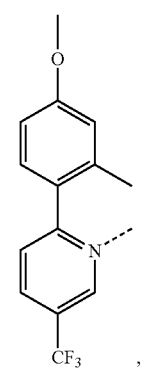 (X-11),
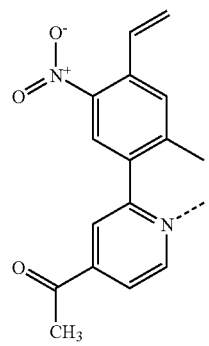 (X-12),
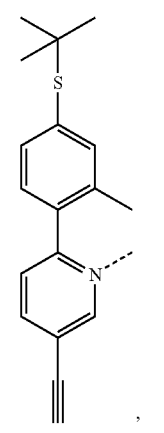 (X-13), -continued
(X-14)
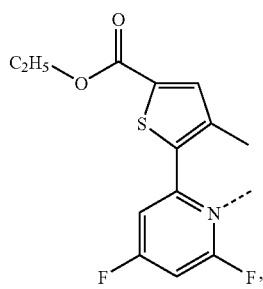
(X-15)
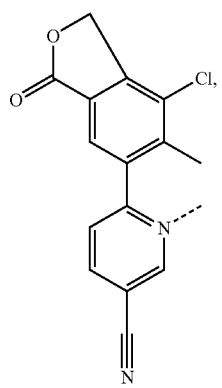
(X-16)
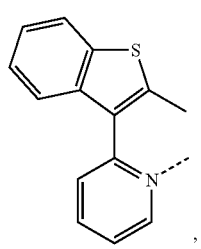
(X-17)
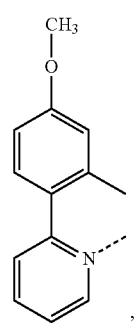
(X-18)
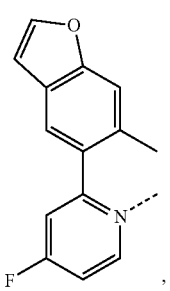
-continued
(X-19)
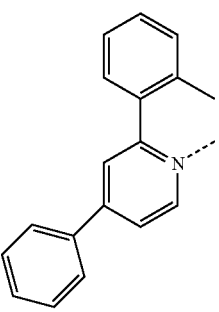
(X-20)
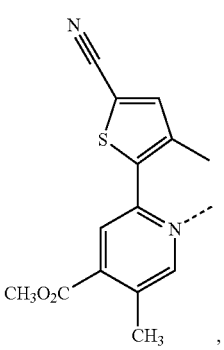
(X-21)
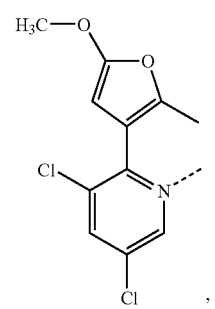
(X-22)
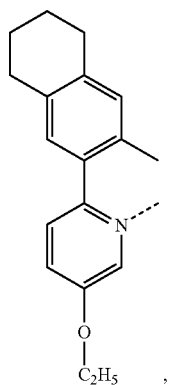
(X-23)
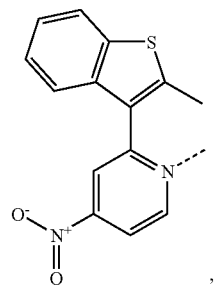

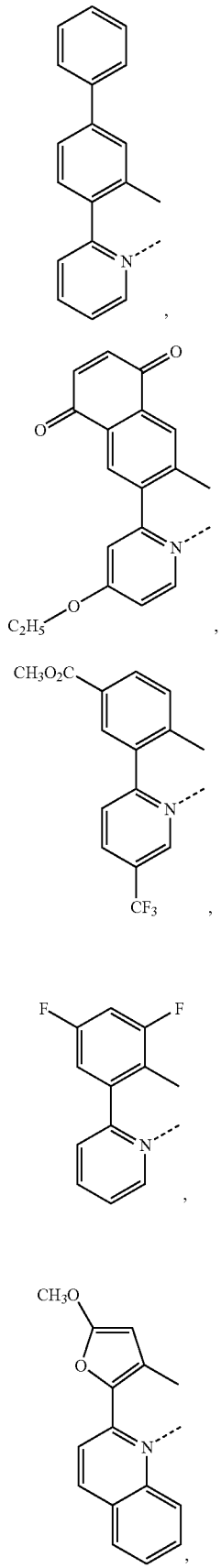
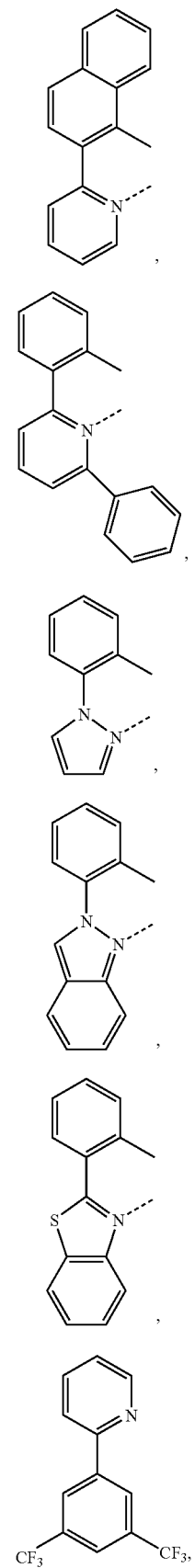

(X-35) 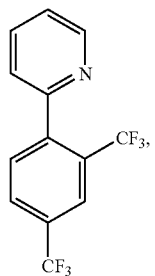
(X-36) 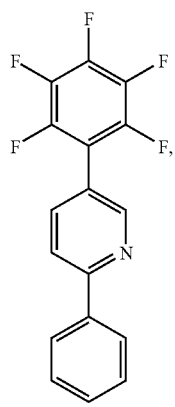
(X-37) 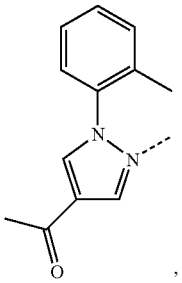
(X-37) 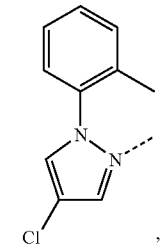
(X-38) 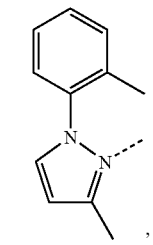
(X-39)
(X-40)
(X-41)
(X-42) 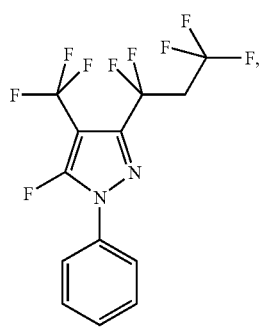

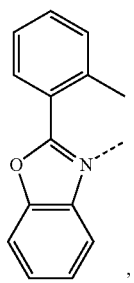 (X-43)
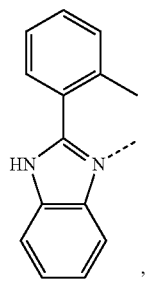 (X-44)
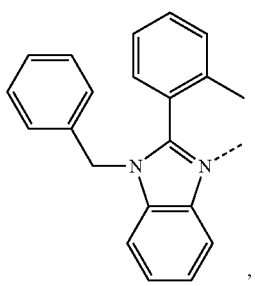 (X-45)
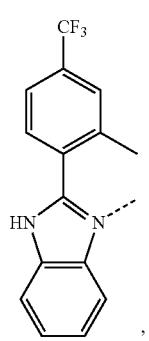 (X-46)
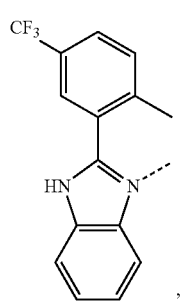 (X-47)
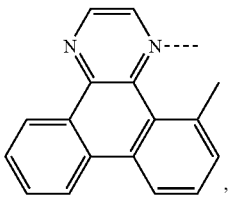 (X-48)
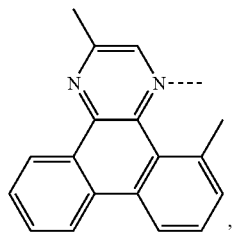 (X-49)
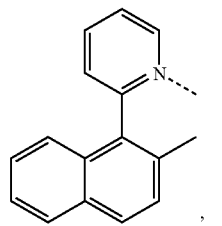 (X-50)
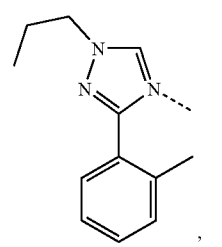 (X-51)
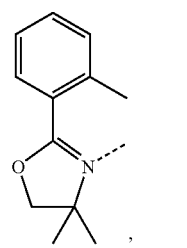 (X-52)
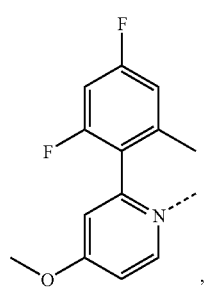 (X-53)

-continued

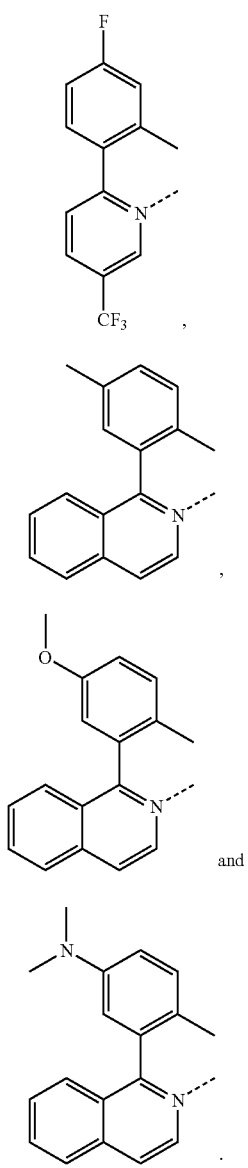

In case of the metal complex $(L^a)_2IrL'$ three isomers can exist.

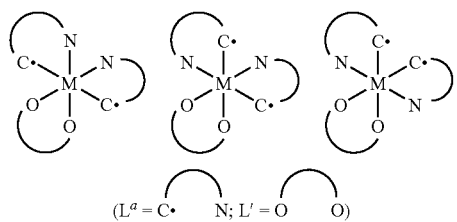

$(L^a = C\cdot \quad N;\ L' = O \quad O)$

In some cases mixtures of isomers are obtained. Often the mixture can be used without isolating the individual isomers. The isomers can be separated by conventional methods, as described in A. B. Tamayo et al., J. Am. Chem. Soc. 125 (2003) 7377-7387.

The at present most preferred ligands L are listed below:

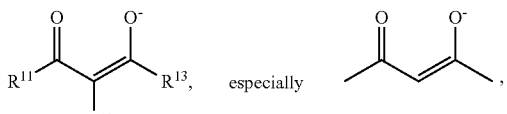

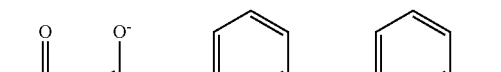

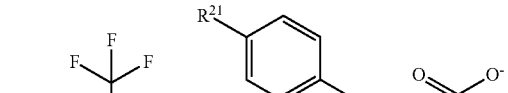

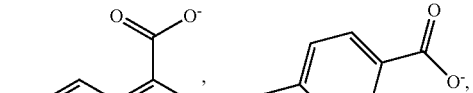

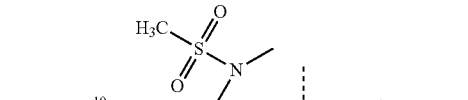

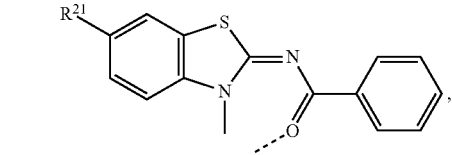

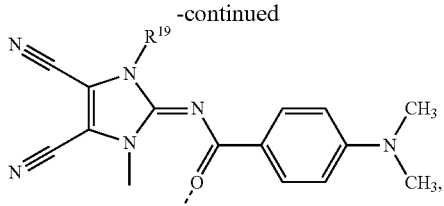
(X-1)

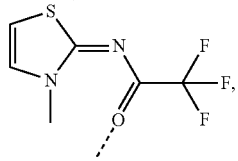
(X-4)

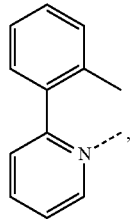
(X-6)

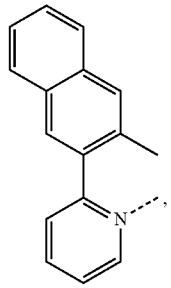
(X-29)

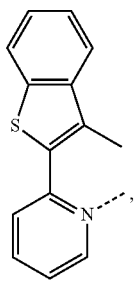
(X-48)

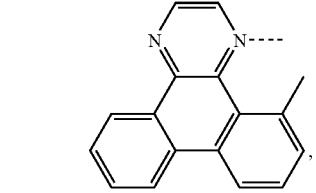

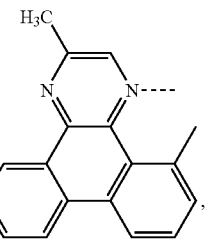
(X-49)

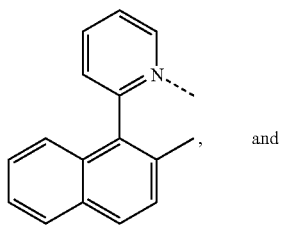
(X-50) and

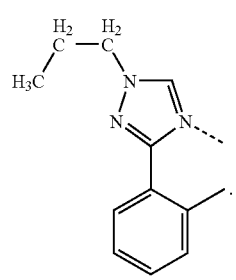
(X-51)

In a preferred embodiment the present invention is directed to compounds of formula Va, or Vb, wherein $M^2$ is Rh, or Re, especially Ir, $R^2$ and $R^3$ are independently of each other H, $C_1$-$C_8$ perfluoroalkyl, especially $CF_3$, or CN, $R^6$ is H, —$NR^{25}R^{26}$, or $C_1$-$C_{18}$alkoxy, wherein $R^{25}$ and $R^{26}$ are independently of each other $C_1$-$C_{18}$alkyl, or phenyl, which may be substituted by one, or more groups $C_1$-$C_{18}$alkoxy, or $C_1$-$C_{18}$alkyl, and L is a bidentate ligand.

In another preferred embodiment the present invention is directed to compounds of formula VIIa, or VIIb, wherein $M^4$ is Pd, especially Pt, $R^2$ and $R^3$ are independently of each other H, $C_1$-$C_8$ perfluoroalkyl, especially $CF_3$, or CN, $R^6$ is H, —$NR^{25}R^{26}$, or $C_1$-$C_{18}$alkoxy, wherein $R^{25}$ and $R^{26}$ are independently of each other $C_1$-$C_{18}$alkyl, or phenyl, which may be substituted by one, or more groups $C_1$-$C_{18}$alkoxy, or $C_1$-$C_{18}$alkyl, and L is a bidentate ligand.

Preferences for the bidentate ligand L are given above, wherein the following ligands L are advantageously used:

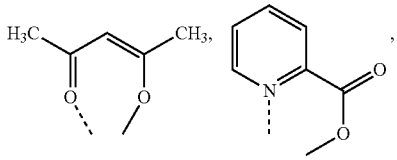

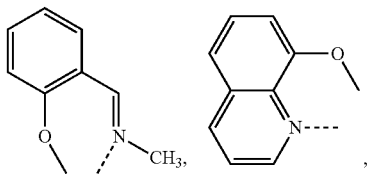, 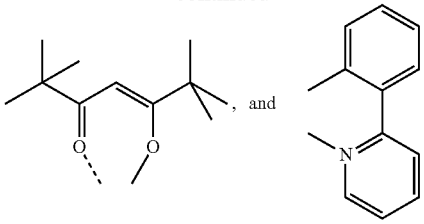

A compound of formulae shown below:

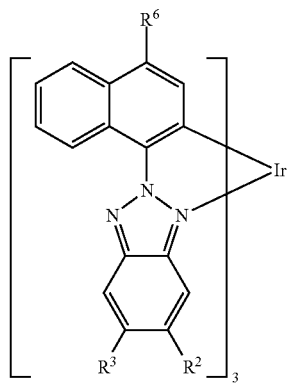

wherein

| Cpd. | R² | R³ | R⁶ |
|---|---|---|---|
| A-1 | H | H | H |
| A-2 | H | H | OCH₃ |
| A-3 | H | H | OCH₂CH₃ |
| A-4 | H | H | O-n-butyl |
| A-5 | H | H | O-iso-butyl |
| A-6 | H | H | O-2-butyl |
| A-7 | H | H | O-2-ethylhexyl |
| A-8 | H | H | N(CH₃)₂ |
| A-9 | H | H | NPh₂ |
| A-10 | H | CF₃ | H |
| A-11 | CF₃ | H | H |
| A-12 | H | CF₃ | OCH₃ |
| A-13 | CF₃ | H | OCH₃ |
| A-14 | H | CF₃ | OCH₂CH₃ |
| A-15 | CF₃ | H | OCH₂CH₃ |
| A-16 | H | CF₃ | O-n-butyl |
| A-17 | CF₃ | H | O-n-butyl |
| A-18 | H | CF₃ | O-iso-butyl |
| A-19 | CF₃ | H | O-iso-butyl |
| A-20 | H | CF₃ | O-2-butyl |
| A-21 | CF₃ | H | O-2-butyl |
| A-22 | H | CF₃ | O-2-ethylhexyl |
| A-23 | CF₃ | H | O-2-ethylhexyl |
| A-24 | H | CF₃ | N(CH₃)₂ |
| A-25 | CF₃ | H | N(CH₃)₂ |
| A-26 | H | CF₃ | NPh₂ |
| A-27 | CF₃ | H | NPh₂ |
| A-28 | H | CN | H |
| A-29 | CN | H | H |
| A-30 | H | CN | OCH₃ |
| A-31 | CN | H | OCH₂CH₃ |
| A-32 | H | CN | OCH₂CH₃ |
| A-33 | CN | H | O-n-butyl |
| A-34 | H | CN | O-n-butyl |
| A-35 | CN | H | O-iso-butyl |
| A-36 | H | CN | O-iso-butyl |
| A-37 | CN | H | O-2-butyl |
| A-38 | H | CN | O-2-butyl |
| A-39 | CN | H | O-2-ethylhexyl |
| A-40 | H | CN | O-2-ethylhexyl |
| A-41 | CN | H | N(CH₃)₂ |
| A-42 | H | CN | N(CH₃)₂ |
| A-43 | CN | H | NPh₂ |

| | | -continued | | |
|---|---|---|---|---|
| A-44 | H | CN | | NPh₂ |

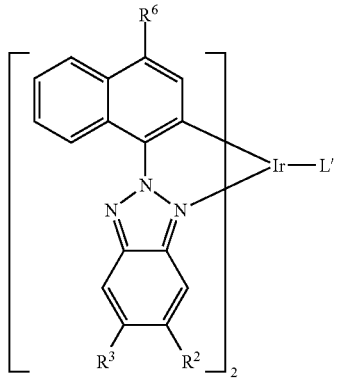

wherein

| Cpd. | L' | R² | R³ | R⁶ |
|---|---|---|---|---|
| B-1 | A¹⁾ | H | H | H |
| B-2 | A¹⁾ | H | H | OCH₃ |
| B-3 | A¹⁾ | H | H | OCH₂CH₃ |
| B-4 | A¹⁾ | H | H | O-n-butyl |
| B-5 | A¹⁾ | H | H | O-iso-butyl |
| B-6 | A¹⁾ | H | H | O-2-butyl |
| B-7 | A¹⁾ | H | H | O-2-ethylhexyl |
| B-8 | A¹⁾ | H | H | N(CH₃)₂ |
| B-9 | A¹⁾ | H | H | NPh₂ |
| B-10 | A¹⁾ | H | CF₃ | H |
| B-11 | A¹⁾ | CF₃ | H | H |
| B-12 | A¹⁾ | H | CF₃ | OCH₃ |
| B-13 | A¹⁾ | CF₃ | H | OCH₃ |
| B-14 | A¹⁾ | H | CF₃ | OCH₂CH₃ |
| B-15 | A¹⁾ | CF₃ | H | OCH₂CH₃ |
| B-16 | A¹⁾ | H | CF₃ | O-n-butyl |
| B-17 | A¹⁾ | CF₃ | H | O-n-butyl |
| B-18 | A¹⁾ | H | CF₃ | O-iso-butyl |
| B-19 | A¹⁾ | CF₃ | H | O-iso-butyl |
| B-20 | A¹⁾ | H | CF₃ | O-2-butyl |
| B-21 | A¹⁾ | CF₃ | H | O-2-butyl |
| B-22 | A¹⁾ | H | CF₃ | O-2-ethylhexyl |
| B-23 | A¹⁾ | CF₃ | H | O-2-ethylhexyl |
| B-24 | A¹⁾ | H | CF₃ | N(CH₃)₂ |
| B-25 | A¹⁾ | CF₃ | H | N(CH₃)₂ |
| B-26 | A¹⁾ | H | CF₃ | NPh₂ |
| B-27 | A¹⁾ | CF₃ | H | NPh₂ |
| B-28 | A¹⁾ | H | CN | H |
| B-29 | A¹⁾ | CN | H | H |
| B-30 | A¹⁾ | CN | H | OCH₃ |
| B-31 | A¹⁾ | H | CN | OCH₃ |
| B-32 | A¹⁾ | CN | H | OCH₂CH₃ |
| B-33 | A¹⁾ | H | CN | OCH₂CH₃ |
| B-34 | A¹⁾ | CN | H | O-n-butyl |
| B-35 | A¹⁾ | H | CN | O-n-butyl |
| B-36 | A¹⁾ | CN | H | O-iso-butyl |
| B-37 | A¹⁾ | H | CN | O-iso-butyl |
| B-38 | A¹⁾ | CN | H | O-2-butyl |
| B-39 | A¹⁾ | H | CN | O-2-butyl |
| B-40 | A¹⁾ | CN | H | O-2-ethylhexyl |
| B-41 | A¹⁾ | H | CN | O-2-ethylhexyl |
| B-42 | A¹⁾ | CN | H | N(CH₃)₂ |
| B-43 | A¹⁾ | H | CN | N(CH₃)₂ |
| B-44 | A¹⁾ | CN | H | NPh₂ |
| B-45 | A¹⁾ | H | CN | NPh₂ |
| B-46 | B¹⁾ | H | H | H |
| B-47 | B¹⁾ | H | H | OCH₃ |
| B-48 | B¹⁾ | H | H | OCH₂CH₃ |
| B-49 | B¹⁾ | H | H | O-n-butyl |
| B-50 | B¹⁾ | H | H | O-iso-butyl |
| B-51 | B¹⁾ | H | H | O-2-butyl |
| B-52 | B¹⁾ | H | H | O-2-ethylhexyl |
| B-53 | B¹⁾ | H | H | N(CH₃)₂ |
| B-54 | B¹⁾ | H | H | NPh₂ |
| B-55 | B¹⁾ | H | CF₃ | H |
| B-56 | B¹⁾ | CF₃ | H | H |

-continued

| | | | | |
|---|---|---|---|---|
| B-57 | B[1] | H | CF$_3$ | OCH$_3$ |
| B-58 | B[1] | CF$_3$ | H | OCH$_3$ |
| B-59 | B[1] | H | CF$_3$ | OCH$_2$CH$_3$ |
| B-60 | B[1] | CF$_3$ | H | OCH$_2$CH$_3$ |
| B-61 | B[1] | H | CF$_3$ | O-n-butyl |
| B-62 | B[1] | CF$_3$ | H | O-n-butyl |
| B-63 | B[1] | H | CF$_3$ | O-iso-butyl |
| B-64 | B[1] | CF$_3$ | H | O-iso-butyl |
| B-65 | B[1] | H | CF$_3$ | O-2-butyl |
| B-66 | B[1] | CF$_3$ | H | O-2-butyl |
| B-67 | B[1] | H | CF$_3$ | O-2-ethylhexyl |
| B-68 | B[1] | CF$_3$ | H | O-2-ethylhexyl |
| B-69 | B[1] | H | CF$_3$ | N(CH$_3$)$_2$ |
| B-70 | B[1] | CF$_3$ | H | N(CH$_3$)$_2$ |
| B-71 | B[1] | H | CF$_3$ | NPh$_2$ |
| B-72 | B[1] | CF$_3$ | H | NPh$_2$ |
| B-73 | B[1] | H | CN | H |
| B-74 | B[1] | CN | H | H |
| B-75 | B[1] | CN | H | OCH$_3$ |
| B-76 | B[1] | H | CN | OCH$_3$ |
| B-77 | B[1] | CN | H | OCH$_2$CH$_3$ |
| B-78 | B[1] | H | CN | OCH$_2$CH$_3$ |
| B-79 | B[1] | CN | H | O-n-butyl |
| B-80 | B[1] | H | CN | O-n-butyl |
| B-81 | B[1] | CN | H | O-iso-butyl |
| B-82 | B[1] | H | CN | O-iso-butyl |
| B-83 | B[1] | CN | H | O-2-butyl |
| B-84 | B[1] | H | CN | O-2-butyl |
| B-85 | B[1] | CN | H | O-2-ethylhexyl |
| B-86 | B[1] | H | CN | O-2-ethylhexyl |
| B-87 | B[1] | CN | H | N(CH$_3$)$_2$ |
| B-88 | B[1] | H | CN | N(CH$_3$)$_2$ |
| B-89 | B[1] | CN | H | NPh$_2$ |
| B-99 | B[1] | H | CN | NPh$_2$ |
| B-100 | C[1] | H | H | H |
| B-101 | C[1] | H | H | OCH$_3$ |
| B-102 | C[1] | H | H | OCH$_2$CH$_3$ |
| B-103 | C[1] | H | H | O-n-butyl |
| B-104 | C[1] | H | H | O-iso-butyl |
| B-105 | C[1] | H | H | O-2-butyl |
| B-106 | C[1] | H | H | O-2-ethylhexyl |
| B-107 | C[1] | H | H | N(CH$_3$)$_2$ |
| B-108 | C[1] | H | H | NPh$_2$ |
| B-109 | C[1] | H | CF$_3$ | H |
| B-110 | C[1] | CF$_3$ | H | H |
| B-111 | C[1] | H | CF$_3$ | OCH$_3$ |
| B-112 | C[1] | CF$_3$ | H | OCH$_3$ |
| B-113 | C[1] | H | CF$_3$ | OCH$_2$CH$_3$ |
| B-114 | C[1] | CF$_3$ | H | OCH$_2$CH$_3$ |
| B-115 | C[1] | H | CF$_3$ | O-n-butyl |
| B-116 | C[1] | CF$_3$ | H | O-n-butyl |
| B-117 | C[1] | H | CF$_3$ | O-iso-butyl |
| B-118 | C[1] | CF$_3$ | H | O-iso-butyl |
| B-119 | C[1] | H | CF$_3$ | O-2-butyl |
| B-120 | C[1] | CF$_3$ | H | O-2-butyl |
| B-121 | C[1] | H | CF$_3$ | O-2-ethylhexyl |
| B-122 | C[1] | CF$_3$ | H | O-2-ethylhexyl |
| B-123 | C[1] | H | CF$_3$ | N(CH$_3$)$_2$ |
| B-124 | C[1] | CF$_3$ | H | N(CH$_3$)$_2$ |
| B-125 | C[1] | H | CF$_3$ | NPh$_2$ |
| B-126 | C[1] | CF$_3$ | H | NPh$_2$ |
| B-127 | C[1] | H | CN | H |
| B-128 | C[1] | CN | H | H |
| B-129 | C[1] | CN | H | OCH$_3$ |
| B-130 | C[1] | H | CN | OCH$_3$ |
| B-131 | C[1] | CN | H | OCH$_2$CH$_3$ |
| B-132 | C[1] | H | CN | OCH$_2$CH$_3$ |
| B-133 | C[1] | CN | H | O-n-butyl |
| B-134 | C[1] | H | CN | O-n-butyl |
| B-135 | C[1] | CN | H | O-iso-butyl |
| B-136 | C[1] | H | CN | O-iso-butyl |
| B-137 | C[1] | CN | H | O-2-butyl |
| B-138 | C[1] | H | CN | O-2-butyl |
| B-139 | C[1] | CN | H | O-2-ethylhexyl |
| B-140 | C[1] | H | CN | O-2-ethylhexyl |
| B-141 | C[1] | CN | H | N(CH$_3$)$_2$ |
| B-142 | C[1] | H | CN | N(CH$_3$)$_2$ |
| B-143 | C[1] | H | CN | NPh$_2$ |
| B-144 | C[1] | CN | H | NPh$_2$ |

-continued

| | | | | |
|---|---|---|---|---|
| B-145 | D[1] | H | H | H |
| B-146 | D[1] | H | H | OCH$_3$ |
| B-147 | D[1] | H | H | OCH$_2$CH$_3$ |
| B-148 | D[1] | H | H | O-n-butyl |
| B-149 | D[1] | H | H | O-iso-butyl |
| B-150 | D[1] | H | H | O-2-butyl |
| B-151 | D[1] | H | H | O-2-ethylhexyl |
| B-152 | D[1] | H | H | N(CH$_3$)$_2$ |
| B-153 | D[1] | H | H | NPh$_2$ |
| B-154 | D[1] | H | CF$_3$ | H |
| B-155 | D[1] | CF$_3$ | H | H |
| B-156 | D[1] | H | CF$_3$ | OCH$_3$ |
| B-157 | D[1] | CF$_3$ | H | OCH$_3$ |
| B-158 | D[1] | H | CF$_3$ | OCH$_2$CH$_3$ |
| B-159 | D[1] | CF$_3$ | H | OCH$_2$CH$_3$ |
| B-160 | D[1] | H | CF$_3$ | O-n-butyl |
| B-161 | D[1] | CF$_3$ | H | O-n-butyl |
| B-162 | D[1] | H | CF$_3$ | O-iso-butyl |
| B-163 | D[1] | CF$_3$ | H | O-iso-butyl |
| B-164 | D[1] | H | CF$_3$ | O-2-butyl |
| B-165 | D[1] | CF$_3$ | H | O-2-butyl |
| B-166 | D[1] | H | CF$_3$ | O-2-ethylhexyl |
| B-167 | D[1] | CF$_3$ | H | O-2-ethylhexyl |
| B-168 | D[1] | H | CF$_3$ | N(CH$_3$)$_2$ |
| B-169 | D[1] | CF$_3$ | H | N(CH$_3$)$_2$ |
| B-170 | D[1] | H | CF$_3$ | NPh$_2$ |
| B-171 | D[1] | CF$_3$ | H | NPh$_2$ |
| B-172 | D[1] | H | CN | H |
| B-173 | D[1] | CN | H | H |
| B-174 | D[1] | CN | H | OCH$_3$ |
| B-175 | D[1] | H | CN | OCH$_3$ |
| B-176 | D[1] | CN | H | OCH$_2$CH$_3$ |
| B-177 | D[1] | H | CN | OCH$_2$CH$_3$ |
| B-178 | D[1] | CN | H | O-n-butyl |
| B-179 | D[1] | H | CN | O-n-butyl |
| B-180 | D[1] | CN | H | O-iso-butyl |
| B-181 | D[1] | H | CN | O-iso-butyl |
| B-182 | D[1] | CN | H | O-2-butyl |
| B-183 | D[1] | H | CN | O-2-butyl |
| B-184 | D[1] | CN | H | O-2-ethylhexyl |
| B-185 | D[1] | H | CN | O-2-ethylhexyl |
| B-186 | D[1] | CN | H | N(CH$_3$)$_2$ |
| B-187 | D[1] | H | CN | N(CH$_3$)$_2$ |
| B-188 | D[1] | CN | H | NPh$_2$ |
| B-189 | D[1] | H | CN | NPh$_2$ |
| B-190 | E[1] | H | H | H |
| B-191 | E[1] | H | H | OCH$_3$ |
| B-192 | E[1] | H | H | OCH$_2$CH$_3$ |
| B-193 | E[1] | H | H | O-n-butyl |
| B-194 | E[1] | H | H | O-iso-butyl |
| B-195 | E[1] | H | H | O-2-butyl |
| B-196 | E[1] | H | H | O-2-ethylhexyl |
| B-197 | E[1] | H | H | N(CH$_3$)$_2$ |
| B-198 | E[1] | H | H | NPh$_2$ |
| B-199 | E[1] | H | CF$_3$ | H |
| B-200 | E[1] | CF$_3$ | H | H |
| B-201 | E[1] | H | CF$_3$ | OCH$_3$ |
| B-202 | E[1] | CF$_3$ | H | OCH$_3$ |
| B-203 | E[1] | H | CF$_3$ | OCH$_2$CH$_3$ |
| B-204 | E[1] | CF$_3$ | H | OCH$_2$CH$_3$ |
| B-205 | E[1] | H | CF$_3$ | O-n-butyl |
| B-206 | E[1] | CF$_3$ | H | O-n-butyl |
| B-207 | E[1] | H | CF$_3$ | O-iso-butyl |
| B-208 | E[1] | CF$_3$ | H | O-iso-butyl |
| B-209 | E[1] | H | CF$_3$ | O-2-butyl |
| B-210 | E[1] | CF$_3$ | H | O-2-butyl |
| B-211 | E[1] | H | CF$_3$ | O-2-ethylhexyl |
| B-212 | E[1] | CF$_3$ | H | O-2-ethylhexyl |
| B-213 | E[1] | H | CF$_3$ | N(CH$_3$)$_2$ |
| B-214 | E[1] | CF$_3$ | H | N(CH$_3$)$_2$ |
| B-215 | E[1] | H | CF$_3$ | NPh$_2$ |
| B-216 | E[1] | CF$_3$ | H | NPh$_2$ |
| B-217 | E[1] | H | CN | H |
| B-218 | E[1] | CN | H | H |
| B-219 | E[1] | CN | H | OCH$_3$ |
| B-220 | E[1] | H | CN | OCH$_3$ |
| B-221 | E[1] | CN | H | OCH$_2$CH$_3$ |
| B-222 | E[1] | H | CN | OCH$_2$CH$_3$ |
| B-223 | E[1] | CN | H | O-n-butyl |

-continued

| | | | | |
|---|---|---|---|---|
| B-224 | E[1]) | H | CN | O-n-butyl |
| B-225 | E[1]) | CN | H | O-iso-butyl |
| B-226 | E[1]) | H | CN | O-iso-butyl |
| B-227 | E[1]) | CN | H | O-2-butyl |
| B-228 | E[1]) | H | CN | O-2-butyl |
| B-229 | E[1]) | CN | H | O-2-ethylhexyl |
| B-230 | E[1]) | H | CN | O-2-ethylhexyl |
| B-231 | E[1]) | CN | H | N(CH$_3$)$_2$ |
| B-232 | E[1]) | H | CN | N(CH$_3$)$_2$ |
| B-233 | E[1]) | CN | H | NPh$_2$ |
| B-234 | E[1]) | H | CN | NPh$_2$ |

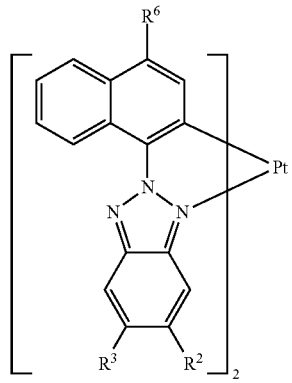

wherein

| Cpd. | R$^2$ | R$^3$ | R$^6$ |
|---|---|---|---|
| C-1 | H | H | H |
| C-2 | H | H | OCH$_3$ |
| C-3 | H | H | OCH$_2$CH$_3$ |
| C-4 | H | H | O-n-butyl |
| C-5 | H | H | O-iso-butyl |
| C-6 | H | H | O-2-butyl |
| C-7 | H | H | O-2-ethylhexyl |
| C-8 | H | H | N(CH$_3$)$_2$ |
| C-9 | H | H | NPh$_2$ |
| C-10 | H | CF$_3$ | H |
| C-11 | CF$_3$ | H | H |
| C-12 | H | CF$_3$ | OCH$_3$ |
| C-13 | CF$_3$ | H | OCH$_3$ |
| C-14 | H | CF$_3$ | OCH$_2$CH$_3$ |
| C-15 | CF$_3$ | H | OCH$_2$CH$_3$ |
| C-16 | H | CF$_3$ | O-n-butyl |
| C-17 | CF$_3$ | H | O-n-butyl |
| C-18 | H | CF$_3$ | O-iso-butyl |
| C-19 | CF$_3$ | H | O-iso-butyl |
| C-20 | H | CF$_3$ | O-2-butyl |
| C-21 | CF$_3$ | H | O-2-butyl |
| C-22 | H | CF$_3$ | O-2-ethylhexyl |
| C-23 | CF$_3$ | H | O-2-ethylhexyl |
| C-24 | H | CF$_3$ | N(CH$_3$)$_2$ |
| C-25 | CF$_3$ | H | N(CH$_3$)$_2$ |
| C-26 | H | CF$_3$ | NPh$_2$ |
| C-27 | CF$_3$ | H | NPh$_2$ |
| C-28 | H | CN | H |
| C-29 | CN | H | H |
| C-30 | H | CN | OCH$_3$ |
| C-31 | CN | H | OCH$_2$CH$_3$ |
| C-32 | H | CN | OCH$_2$CH$_3$ |
| C-33 | CN | H | O-n-butyl |
| C-34 | H | CN | O-n-butyl |
| C-35 | CN | H | O-iso-butyl |
| C-36 | H | CN | O-iso-butyl |
| C-37 | CN | H | O-2-butyl |
| C-38 | H | CN | O-2-butyl |
| C-39 | CN | H | O-2-ethylhexyl |
| C-40 | H | CN | O-2-ethylhexyl |
| C-41 | CN | H | N(CH$_3$)$_2$ |
| C-42 | H | CN | N(CH$_3$)$_2$ |
| C-43 | CN | H | NPh$_2$ |
| C-44 | H | CN | NPh$_2$ |

-continued

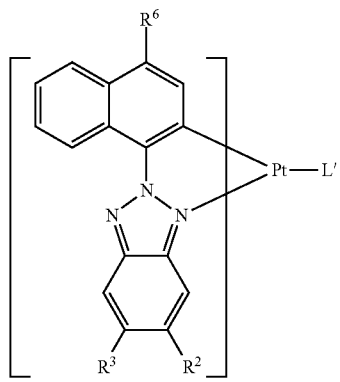

wherein

| Cpd. | L' | R² | R³ | R⁶ |
|---|---|---|---|---|
| D-1 | A[1)] | H | H | H |
| D-2 | A[1)] | H | H | OCH₃ |
| D-3 | A[1)] | H | H | OCH₂CH₃ |
| D-4 | A[1)] | H | H | O-n-butyl |
| D-5 | A[1)] | H | H | O-iso-butyl |
| D-6 | A[1)] | H | H | O-2-butyl |
| D-7 | A[1)] | H | H | O-2-ethylhexyl |
| D-8 | A[1)] | H | H | N(CH₃)₂ |
| D-9 | A[1)] | H | H | NPh₂ |
| D-10 | A[1)] | H | CF₃ | H |
| D-11 | A[1)] | CF₃ | H | H |
| D-12 | A[1)] | H | CF₃ | OCH₃ |
| D-13 | A[1)] | CF₃ | H | OCH₃ |
| D-14 | A[1)] | H | CF₃ | OCH₂CH₃ |
| D-15 | A[1)] | CF₃ | H | OCH₂CH₃ |
| D-16 | A[1)] | H | CF₃ | O-n-butyl |
| D-17 | A[1)] | CF₃ | H | O-n-butyl |
| D-18 | A[1)] | H | CF₃ | O-iso-butyl |
| D-19 | A[1)] | CF₃ | H | O-iso-butyl |
| D-20 | A[1)] | H | CF₃ | O-2-butyl |
| D-21 | A[1)] | CF₃ | H | O-2-butyl |
| D-22 | A[1)] | H | CF₃ | O-2-ethylhexyl |
| D-23 | A[1)] | CF₃ | H | O-2-ethylhexyl |
| D-24 | A[1)] | H | CF₃ | N(CH₃)₂ |
| D-25 | A[1)] | CF₃ | H | N(CH₃)₂ |
| D-26 | A[1)] | H | CF₃ | NPh₂ |
| D-27 | A[1)] | CF₃ | H | NPh₂ |
| D-28 | A[1)] | H | CN | H |
| D-29 | A[1)] | CN | H | H |
| D-30 | A[1)] | CN | H | OCH₃ |
| D-31 | A[1)] | H | CN | OCH₃ |
| D-32 | A[1)] | CN | H | OCH₂CH₃ |
| D-33 | A[1)] | H | CN | OCH₂CH₃ |
| D-34 | A[1)] | CN | H | O-n-butyl |
| D-35 | A[1)] | H | CN | O-n-butyl |
| D-36 | A[1)] | CN | H | O-iso-butyl |
| D-37 | A[1)] | H | CN | O-iso-butyl |
| D-38 | A[1)] | CN | H | O-2-butyl |
| D-39 | A[1)] | H | CN | O-2-butyl |
| D-40 | A[1)] | CN | H | O-2-ethylhexyl |
| D-41 | A[1)] | H | CN | O-2-ethylhexyl |
| D-42 | A[1)] | CN | H | N(CH₃)₂ |
| D-43 | A[1)] | H | CN | N(CH₃)₂ |
| D-44 | A[1)] | CN | H | NPh₂ |
| D-45 | A[1)] | H | CN | NPh₂ |
| D-46 | B[1)] | H | H | H |
| D-47 | B[1)] | H | H | OCH₃ |
| D-48 | B[1)] | H | H | OCH₂CH₃ |
| D-49 | B[1)] | H | H | O-n-butyl |
| D-50 | B[1)] | H | H | O-iso-butyl |
| D-51 | B[1)] | H | H | O-2-butyl |
| D-52 | B[1)] | H | H | O-2-ethylhexyl |
| D-53 | B[1)] | H | H | N(CH₃)₂ |
| D-54 | B[1)] | H | H | NPh₂ |
| D-55 | B[1)] | H | CF₃ | H |
| D-56 | B[1)] | CF₃ | H | H |
| D-57 | B[1)] | H | CF₃ | OCH₃ |
| D-58 | B[1)] | CF₃ | H | OCH₃ |

-continued

| | | | | |
|---|---|---|---|---|
| D-59 | B[1)] | H | CF$_3$ | OCH$_2$CH$_3$ |
| D-60 | B[1)] | CF$_3$ | H | OCH$_2$CH$_3$ |
| D-61 | B[1)] | H | CF$_3$ | O-n-butyl |
| D-62 | B[1)] | CF$_3$ | H | O-n-butyl |
| D-63 | B[1)] | H | CF$_3$ | O-iso-butyl |
| D-64 | B[1)] | CF$_3$ | H | O-iso-butyl |
| D-65 | B[1)] | H | CF$_3$ | O-2-butyl |
| D-66 | B[1)] | CF$_3$ | H | O-2-butyl |
| D-67 | B[1)] | H | CF$_3$ | O-2-ethylhexyl |
| D-68 | B[1)] | CF$_3$ | H | O-2-ethylhexyl |
| D-69 | B[1)] | H | CF$_3$ | N(CH$_3$)$_2$ |
| D-70 | B[1)] | CF$_3$ | H | N(CH$_3$)$_2$ |
| D-71 | B[1)] | H | CF$_3$ | NPh$_2$ |
| D-72 | B[1)] | CF$_3$ | H | NPh$_2$ |
| D-73 | B[1)] | H | CN | H |
| D-74 | B[1)] | CN | H | H |
| D-75 | B[1)] | CN | H | OCH$_3$ |
| D-76 | B[1)] | H | CN | OCH$_3$ |
| D-77 | B[1)] | CN | H | OCH$_2$CH$_3$ |
| D-78 | B[1)] | H | CN | OCH$_2$CH$_3$ |
| D-79 | B[1)] | CN | H | O-n-butyl |
| D-80 | B[1)] | H | CN | O-n-butyl |
| D-81 | B[1)] | CN | H | O-iso-butyl |
| D-82 | B[1)] | H | CN | O-iso-butyl |
| D-83 | B[1)] | CN | H | O-2-butyl |
| D-84 | B[1)] | H | CN | O-2-butyl |
| D-85 | B[1)] | CN | H | O-2-ethylhexyl |
| D-86 | B[1)] | H | CN | O-2-ethylhexyl |
| D-87 | B[1)] | CN | H | N(CH$_3$)$_2$ |
| D-88 | B[1)] | H | CN | N(CH$_3$)$_2$ |
| D-89 | B[1)] | CN | H | NPh$_2$ |
| D-99 | B[1)] | H | CN | NPh$_2$ |
| D-100 | C[1)] | H | H | H |
| D-101 | C[1)] | H | H | OCH$_3$ |
| D-102 | C[1)] | H | H | OCH$_2$CH$_3$ |
| D-103 | C[1)] | H | H | O-n-butyl |
| D-104 | C[1)] | H | H | O-iso-butyl |
| D-105 | C[1)] | H | H | O-2-butyl |
| D-106 | C[1)] | H | H | O-2-ethylhexyl |
| D-107 | C[1)] | H | H | N(CH$_3$)$_2$ |
| D-108 | C[1)] | H | H | NPh$_2$ |
| D-109 | C[1)] | H | CF$_3$ | H |
| D-110 | C[1)] | CF$_3$ | H | H |
| D-111 | C[1)] | H | CF$_3$ | OCH$_3$ |
| D-112 | C[1)] | CF$_3$ | H | OCH$_3$ |
| D-113 | C[1)] | H | CF$_3$ | OCH$_2$CH$_3$ |
| D-114 | C[1)] | CF$_3$ | H | OCH$_2$CH$_3$ |
| D-115 | C[1)] | H | CF$_3$ | O-n-butyl |
| D-116 | C[1)] | CF$_3$ | H | O-n-butyl |
| D-117 | C[1)] | H | CF$_3$ | O-iso-butyl |
| D-118 | C[1)] | CF$_3$ | H | O-iso-butyl |
| D-119 | C[1)] | H | CF$_3$ | O-2-butyl |
| D-120 | C[1)] | CF$_3$ | H | O-2-butyl |
| D-121 | C[1)] | H | CF$_3$ | O-2-ethylhexyl |
| D-122 | C[1)] | CF$_3$ | H | O-2-ethylhexyl |
| D-123 | C[1)] | H | CF$_3$ | N(CH$_3$)$_2$ |
| D-124 | C[1)] | CF$_3$ | H | N(CH$_3$)$_2$ |
| D-125 | C[1)] | H | CF$_3$ | NPh$_2$ |
| D-126 | C[1)] | CF$_3$ | H | NPh$_2$ |
| D-127 | C[1)] | H | CN | H |
| D-128 | C[1)] | CN | H | H |
| D-129 | C[1)] | CN | H | OCH$_3$ |
| D-130 | C[1)] | H | CN | OCH$_3$ |
| D-131 | C[1)] | CN | H | OCH$_2$CH$_3$ |
| D-132 | C[1)] | H | CN | OCH$_2$CH$_3$ |
| D-133 | C[1)] | CN | H | O-n-butyl |
| D-134 | C[1)] | H | CN | O-n-butyl |
| D-135 | C[1)] | CN | H | O-iso-butyl |
| D-136 | C[1)] | H | CN | O-iso-butyl |
| D-137 | C[1)] | CN | H | O-2-butyl |
| D-138 | C[1)] | H | CN | O-2-butyl |
| D-139 | C[1)] | CN | H | O-2-ethylhexyl |
| D-140 | C[1)] | H | CN | O-2-ethylhexyl |
| D-141 | C[1)] | CN | H | N(CH$_3$)$_2$ |
| D-142 | C[1)] | H | CN | N(CH$_3$)$_2$ |
| D-143 | C[1)] | H | CN | NPh$_2$ |
| D-144 | C[1)] | CN | H | NPh$_2$ |
| D-145 | D[1)] | H | H | H |
| D-146 | D[1)] | H | H | OCH$_3$ |

-continued

| | | | | |
|---|---|---|---|---|
| D-147 | D[1] | H | H | OCH$_2$CH$_3$ |
| D-148 | D[1] | H | H | O-n-butyl |
| D-149 | D[1] | H | H | O-iso-butyl |
| D-150 | D[1] | H | H | O-2-butyl |
| D-151 | D[1] | H | H | O-2-ethylhexyl |
| D-152 | D[1] | H | H | N(CH$_3$)$_2$ |
| D-153 | D[1] | H | H | NPh$_2$ |
| D-154 | D[1] | H | CF$_3$ | H |
| D-155 | D[1] | CF$_3$ | H | H |
| D-156 | D[1] | H | CF$_3$ | OCH$_3$ |
| D-157 | D[1] | CF$_3$ | H | OCH$_3$ |
| D-158 | D[1] | H | CF$_3$ | OCH$_2$CH$_3$ |
| D-159 | D[1] | CF$_3$ | H | OCH$_2$CH$_3$ |
| D-160 | D[1] | H | CF$_3$ | O-n-butyl |
| D-161 | D[1] | CF$_3$ | H | O-n-butyl |
| D-162 | D[1] | H | CF$_3$ | O-iso-butyl |
| D-163 | D[1] | CF$_3$ | H | O-iso-butyl |
| D-164 | D[1] | H | CF$_3$ | O-2-butyl |
| D-165 | D[1] | CF$_3$ | H | O-2-butyl |
| D-166 | D[1] | H | CF$_3$ | O-2-ethylhexyl |
| D-167 | D[1] | CF$_3$ | H | O-2-ethylhexyl |
| D-168 | D[1] | H | CF$_3$ | N(CH$_3$)$_2$ |
| D-169 | D[1] | CF$_3$ | H | N(CH$_3$)$_2$ |
| D-170 | D[1] | H | CF$_3$ | NPh$_2$ |
| D-171 | D[1] | CF$_3$ | H | NPh$_2$ |
| D-172 | D[1] | H | CN | H |
| D-173 | D[1] | CN | H | H |
| D-174 | D[1] | CN | H | OCH$_3$ |
| D-175 | D[1] | H | CN | OCH$_3$ |
| D-176 | D[1] | CN | H | OCH$_2$CH$_3$ |
| D-177 | D[1] | H | CN | OCH$_2$CH$_3$ |
| D-178 | D[1] | CN | H | O-n-butyl |
| D-179 | D[1] | H | CN | O-n-butyl |
| D-180 | D[1] | CN | H | O-iso-butyl |
| D-181 | D[1] | H | CN | O-iso-butyl |
| D-182 | D[1] | CN | H | O-2-butyl |
| D-183 | D[1] | H | CN | O-2-butyl |
| D-184 | D[1] | CN | H | O-2-ethylhexyl |
| D-185 | D[1] | H | CN | O-2-ethylhexyl |
| D-186 | D[1] | CN | H | N(CH$_3$)$_2$ |
| D-187 | D[1] | H | CN | N(CH$_3$)$_2$ |
| D-188 | D[1] | CN | H | NPh$_2$ |
| D-189 | D[1] | H | CN | NPh$_2$ |
| D-190 | F[1] | H | H | H |
| D-191 | F[1] | H | H | OCH$_3$ |
| D-192 | F[1] | H | H | OCH$_2$CH$_3$ |
| D-193 | F[1] | H | H | O-n-butyl |
| D-194 | F[1] | H | H | O-iso-butyl |
| D-195 | F[1] | H | H | O-2-butyl |
| D-196 | F[1] | H | H | O-2-ethylhexyl |
| D-197 | F[1] | H | H | N(CH$_3$)$_2$ |
| D-198 | F[1] | H | H | NPh$_2$ |
| D-199 | F[1] | H | CF$_3$ | H |
| D-200 | F[1] | CF$_3$ | H | H |
| D-201 | F[1] | H | CF$_3$ | OCH$_3$ |
| D-202 | F[1] | CF$_3$ | H | OCH$_3$ |
| D-203 | F[1] | H | CF$_3$ | OCH$_2$CH$_3$ |
| D-204 | F[1] | CF$_3$ | H | OCH$_2$CH$_3$ |
| D-205 | F[1] | H | CF$_3$ | O-n-butyl |
| D-206 | F[1] | CF$_3$ | H | O-n-butyl |
| D-207 | F[1] | H | CF$_3$ | O-iso-butyl |
| D-208 | F[1] | CF$_3$ | H | O-iso-butyl |
| D-209 | F[1] | H | CF$_3$ | O-2-butyl |
| D-210 | F[1] | CF$_3$ | H | O-2-butyl |
| D-211 | F[1] | H | CF$_3$ | O-2-ethylhexyl |
| D-212 | F[1] | CF$_3$ | H | O-2-ethylhexyl |
| D-213 | F[1] | H | CF$_3$ | N(CH$_3$)$_2$ |
| D-214 | F[1] | CF$_3$ | H | N(CH$_3$)$_2$ |
| D-215 | F[1] | H | CF$_3$ | NPh$_2$ |
| D-216 | F[1] | CF$_3$ | H | NPh$_2$ |
| D-217 | F[1] | H | CN | H |
| D-218 | F[1] | CN | H | H |
| D-219 | F[1] | CN | H | OCH$_3$ |
| D-220 | F[1] | H | CN | OCH$_3$ |
| D-221 | F[1] | CN | H | OCH$_2$CH$_3$ |
| D-222 | F[1] | H | CN | OCH$_2$CH$_3$ |
| D-223 | F[1] | CN | H | O-n-butyl |
| D-224 | F[1] | H | CN | O-n-butyl |
| D-225 | F[1] | CN | H | O-iso-butyl |

-continued

| | | | | |
|---|---|---|---|---|
| D-226 | F[1] | H | CN | O-iso-butyl |
| D-227 | F[1] | CN | H | O-2-butyl |
| D-228 | F[1] | H | CN | O-2-butyl |
| D-229 | F[1] | CN | H | O-2-ethylhexyl |
| D-230 | F[1] | H | CN | O-2-ethylhexyl |
| D-231 | F[1] | CN | H | N(CH$_3$)$_2$ |
| D-232 | F[1] | H | CN | N(CH$_3$)$_2$ |
| D-233 | F[1] | CN | H | NPh$_2$ |
| D-234 | F[1] | H | CN | NPh$_2$ |
| D-235 | E[1] | H | H | H |
| D-236 | E[1] | H | H | OCH$_3$ |
| D-237 | E[1] | H | H | OCH$_2$CH$_3$ |
| D-238 | E[1] | H | H | O-n-butyl |
| D-239 | E[1] | H | H | O-iso-butyl |
| D-240 | E[1] | H | H | O-2-butyl |
| D-241 | E[1] | H | H | O-2-ethylhexyl |
| D-242 | E[1] | H | H | N(CH$_3$)$_2$ |
| D-243 | E[1] | H | H | NPh$_2$ |
| D-244 | E[1] | H | CF$_3$ | H |
| D-245 | E[1] | CF$_3$ | H | H |
| D-246 | E[1] | H | CF$_3$ | OCH$_3$ |
| D-247 | E[1] | CF$_3$ | H | OCH$_3$ |
| D-248 | E[1] | H | CF$_3$ | OCH$_2$CH$_3$ |
| D-249 | E[1] | CF$_3$ | H | OCH$_2$CH$_3$ |
| D-250 | E[1] | H | CF$_3$ | O-n-butyl |
| D-251 | E[1] | CF$_3$ | H | O-n-butyl |
| D-252 | E[1] | H | CF$_3$ | O-iso-butyl |
| D-253 | E[1] | CF$_3$ | H | O-iso-butyl |
| D-254 | E[1] | H | CF$_3$ | O-2-butyl |
| D-255 | E[1] | CF$_3$ | H | O-2-butyl |
| D-256 | E[1] | H | CF$_3$ | O-2-ethylhexyl |
| D-257 | E[1] | CF$_3$ | H | O-2-ethylhexyl |
| D-258 | E[1] | H | CF$_3$ | N(CH$_3$)$_2$ |
| D-259 | E[1] | CF$_3$ | H | N(CH$_3$)$_2$ |
| D-260 | E[1] | H | CF$_3$ | NPh$_2$ |
| D-261 | E[1] | CF$_3$ | H | NPh$_2$ |
| D-262 | E[1] | H | CN | H |
| D-263 | E[1] | CN | H | H |
| D-264 | E[1] | CN | H | OCH$_3$ |
| D-265 | E[1] | H | CN | OCH$_3$ |
| D-266 | E[1] | CN | H | OCH$_2$CH$_3$ |
| D-267 | E[1] | H | CN | OCH$_2$CH$_3$ |
| D-268 | E[1] | CN | H | O-n-butyl |
| D-269 | E[1] | H | CN | O-n-butyl |
| D-270 | E[1] | CN | H | O-iso-butyl |
| D-271 | E[1] | H | CN | O-iso-butyl |
| D-272 | E[1] | CN | H | O-2-butyl |
| D-273 | E[1] | H | CN | O-2-butyl |
| D-274 | E[1] | CN | H | O-2-ethylhexyl |
| D-275 | E[1] | H | CN | O-2-ethylhexyl |
| D-276 | E[1] | CN | H | N(CH$_3$)$_2$ |
| D-277 | E[1] | H | CN | N(CH$_3$)$_2$ |
| D-278 | E[1] | CN | H | NPh$_2$ |
| D-279 | E[1] | H | CN | NPh$_2$ |
| B-235 | A[1] | CH$_3$ | H | H |
| B-236 | A[1] | H | CH$_3$ | H |
| B-237 | E[1] | CH$_3$ | H | H |
| B-238 | E[1] | H | CH$_3$ | H |
| B-239 | E[1] | H | H | OCH$_3$ |
| B-240 | A[1] | H | H | 2-propoxy |
| B-241 | E[1] | H | H | 2-propoxy |
| B-242 | D[1] | H | H | 2-propoxy |
| B-243 | F[1] | CF$_3$ | H | H |
| B-244 | F[1] | H | CF$_3$ | H |
| B-245 | F[1] | H | H | H |
| B-246 | F[1] | H | H | OCH$_3$ |

[1]A = 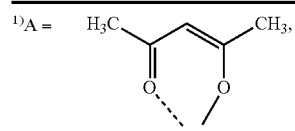

-continued
B = 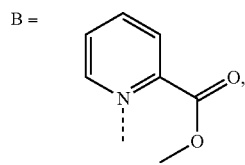
C = 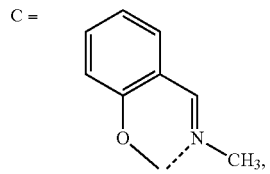
D = 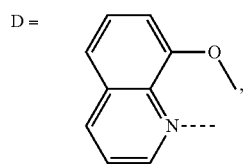
E = 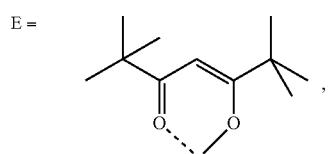
F = 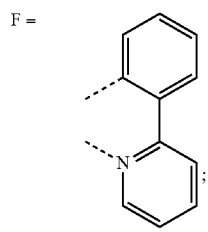
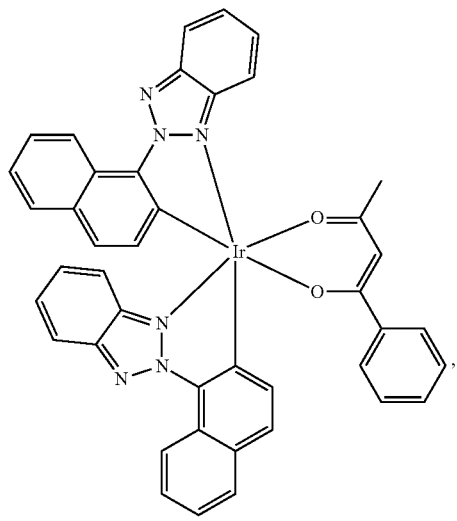
(B-247)

-continued
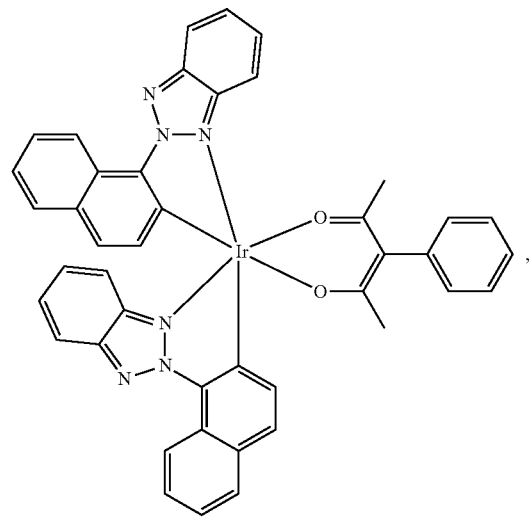
(B-248)
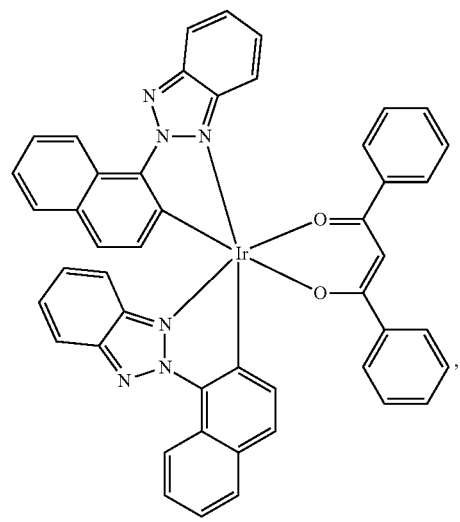
(B-249)

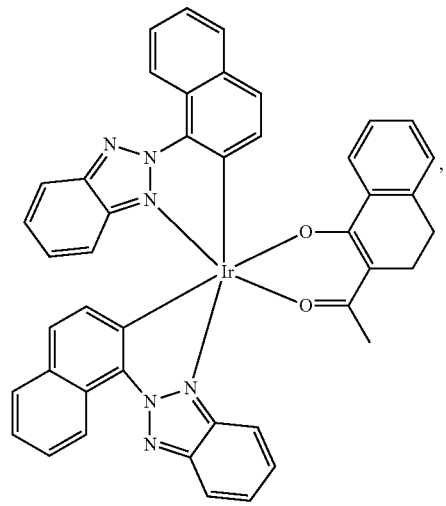
(B-250)
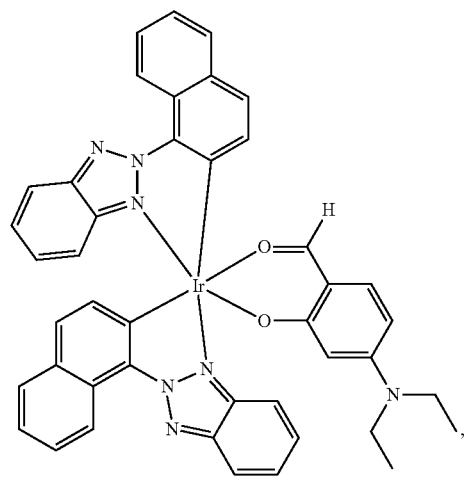
(B-254)
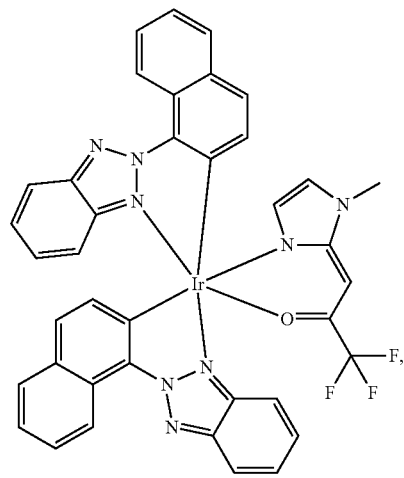
(B-255)

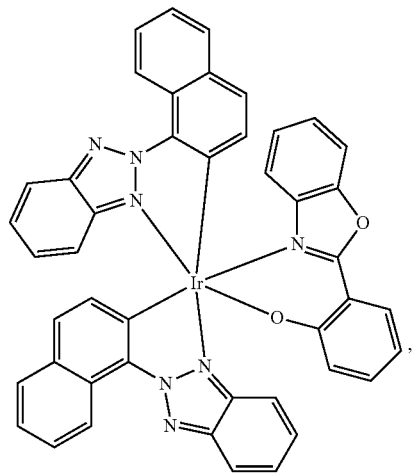
(B-256)
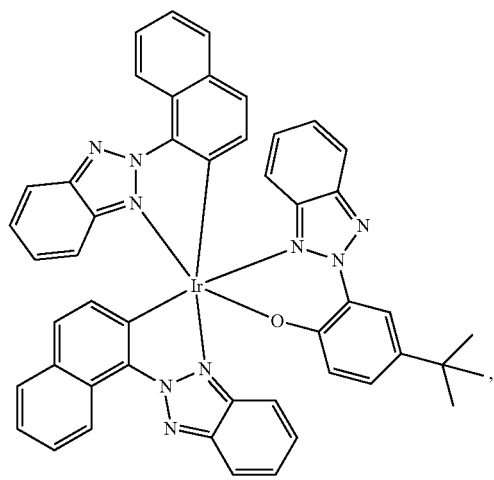
(B-257)
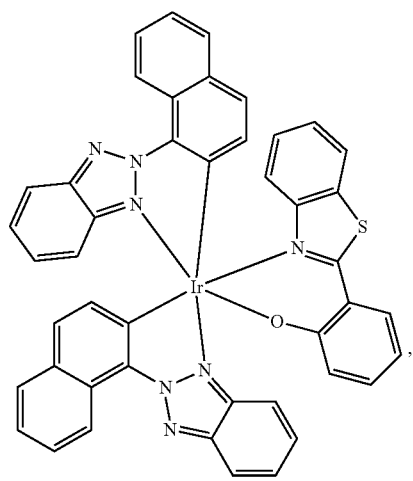
(B-258)

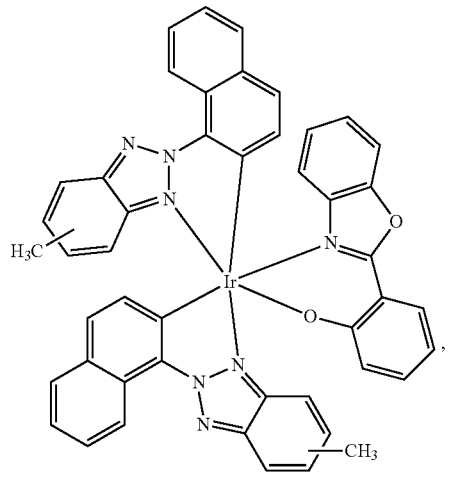
(B-259)
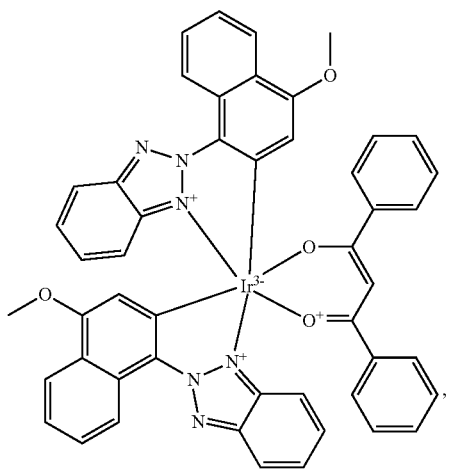
(B-260)
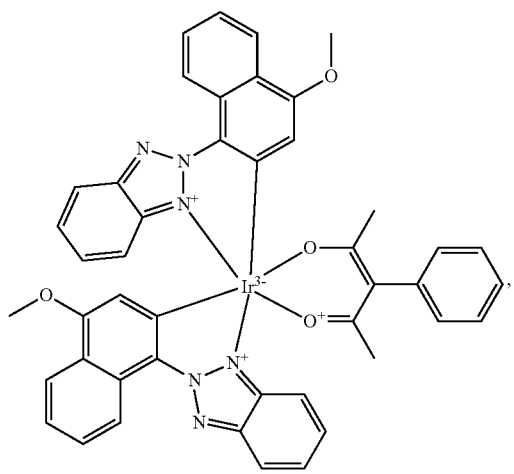
(B-261)

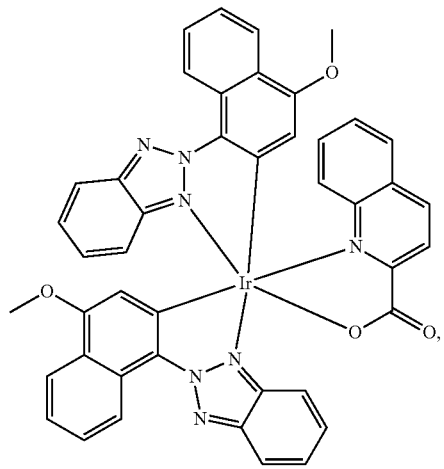
(B-262)
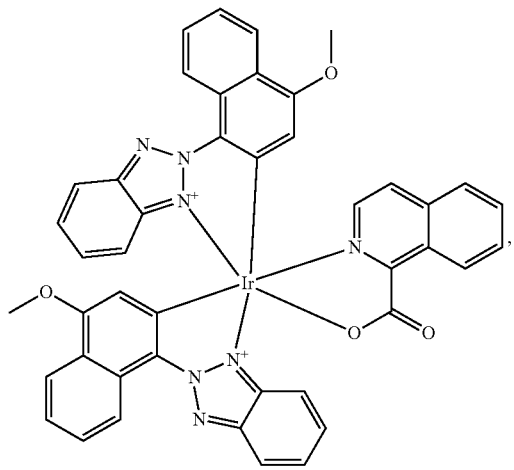
(B-263)
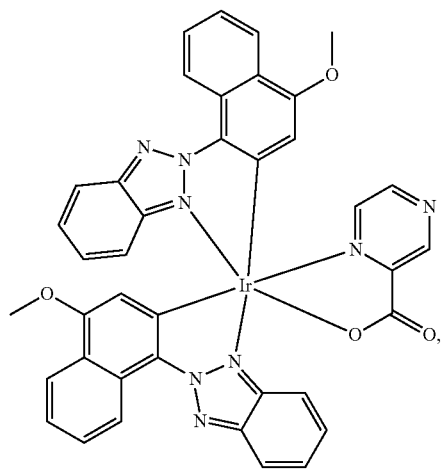
(B-264)

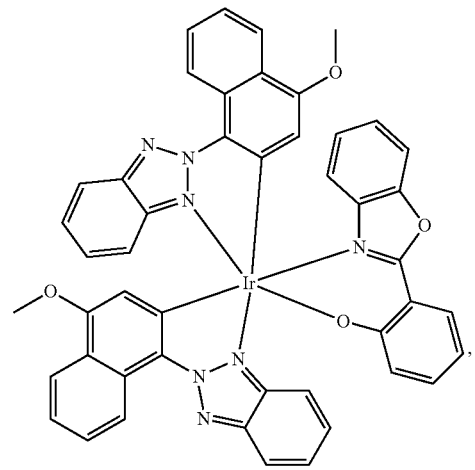
(B-265)
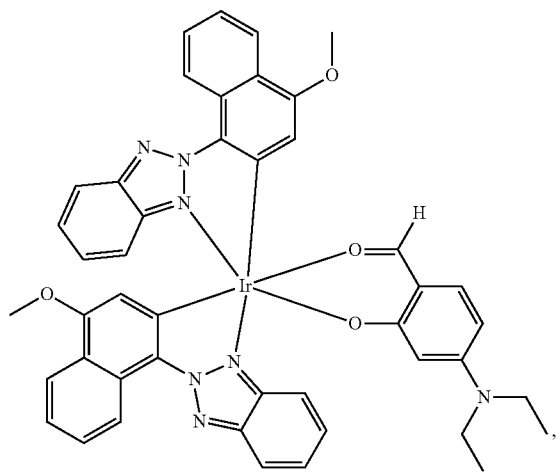
(B-266)
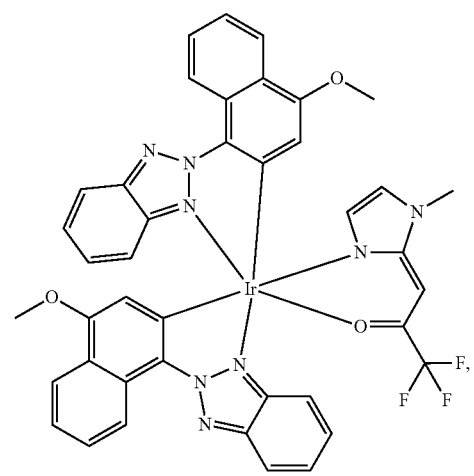
(B-267)

-continued
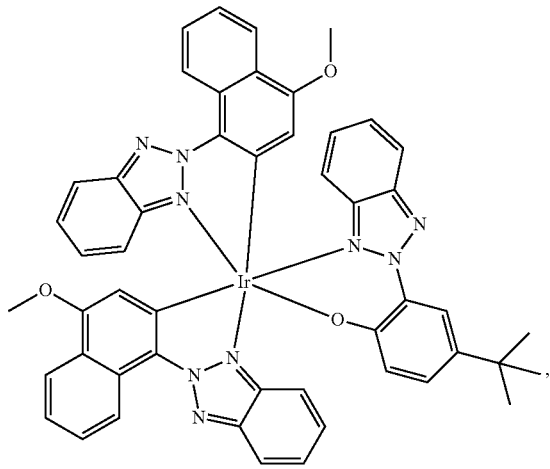
(B-268)
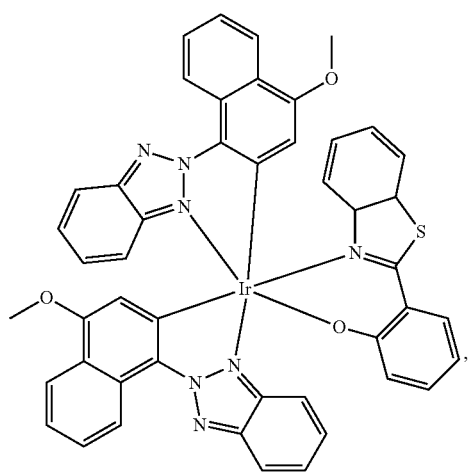
(B-269)
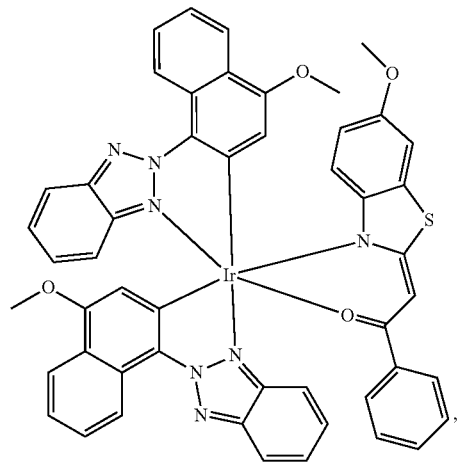
(B-270)

-continued
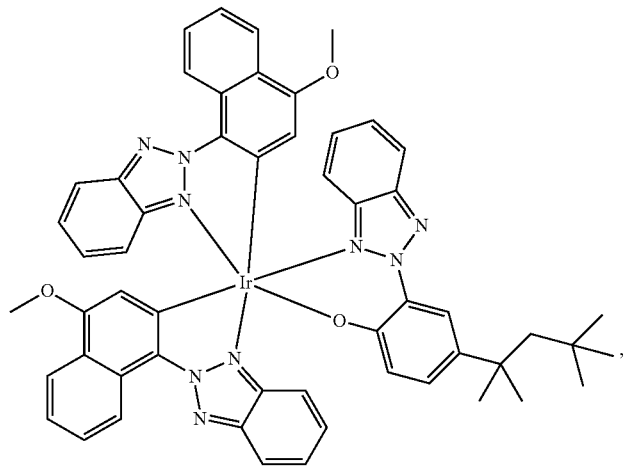
(B-271)
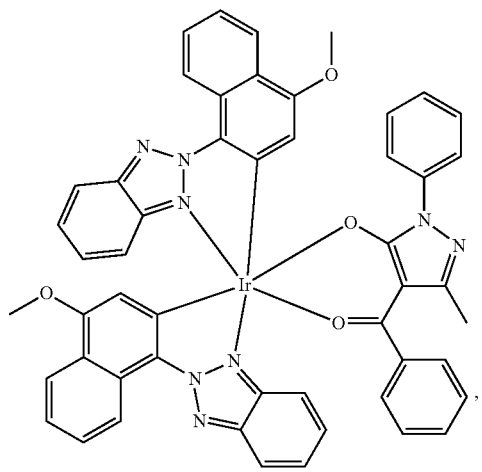
(B-272)
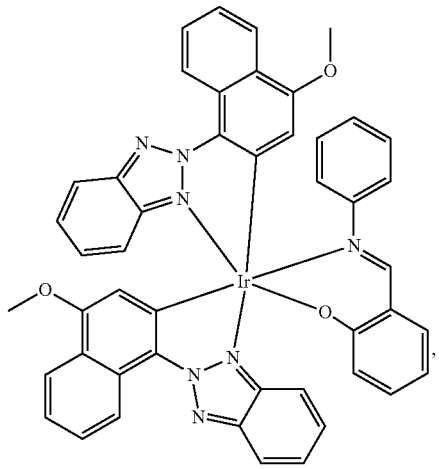
(B-273)

-continued
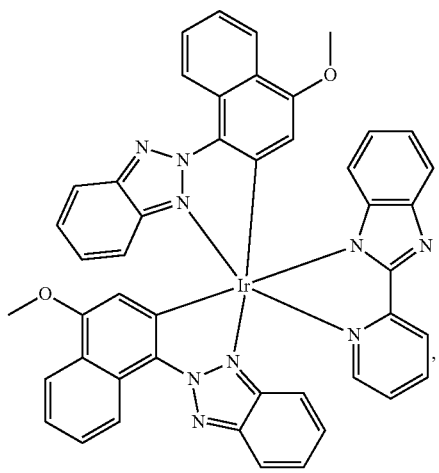
(B-274)
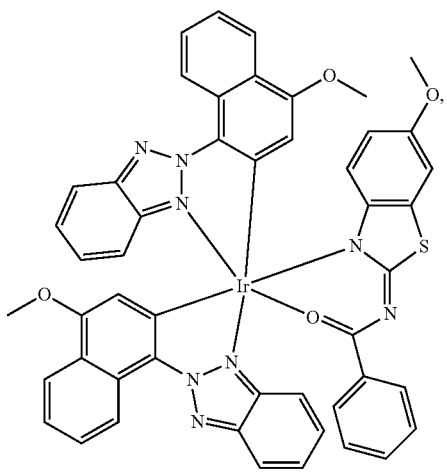
(B-275)
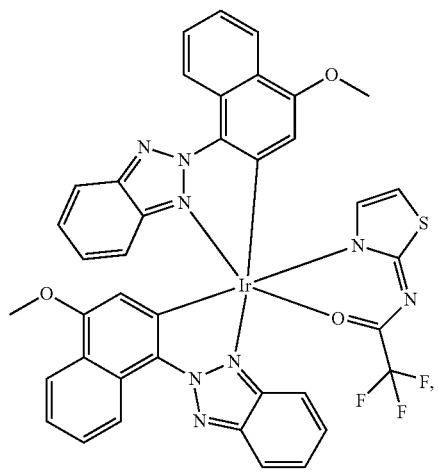
(B-276)

-continued
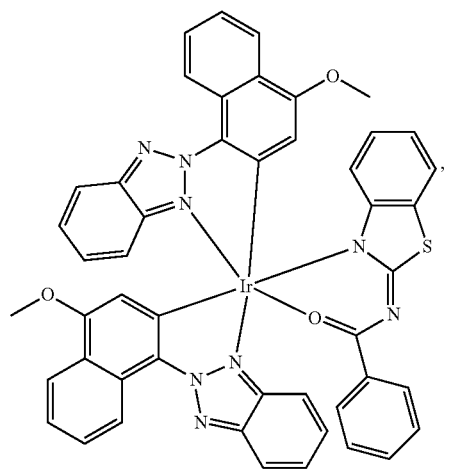
(B-277)
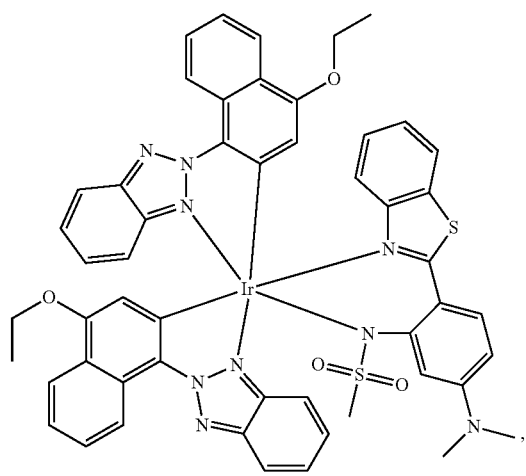
(B-278)
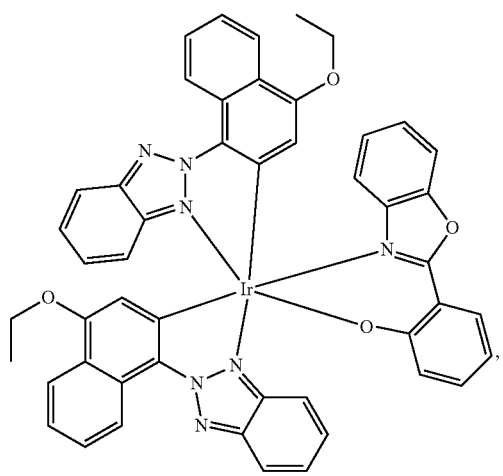
(B-279)

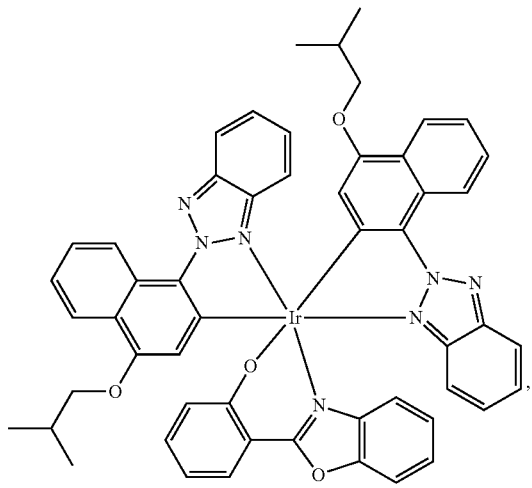
(B-280)
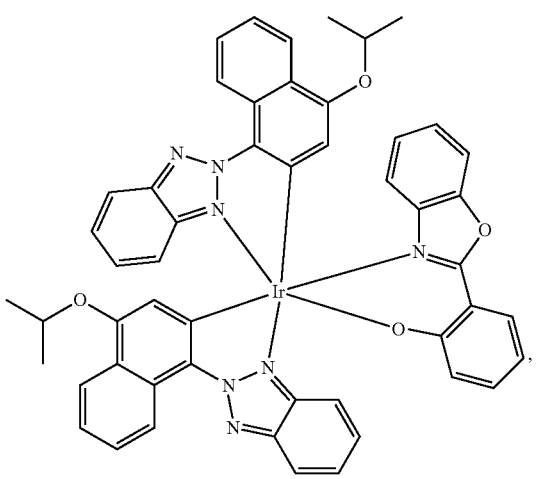
(B-281)
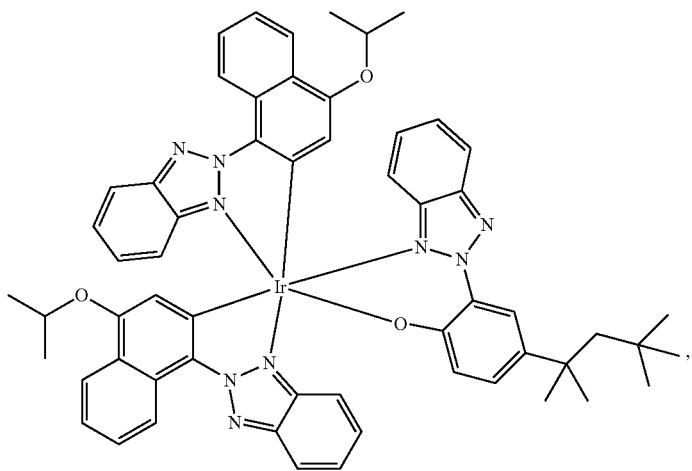
(B-282)

-continued
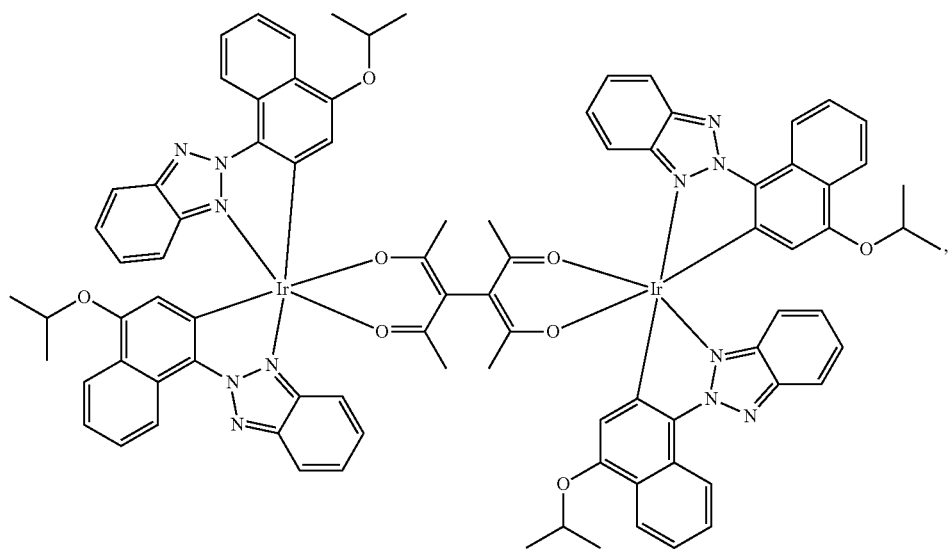
(B-283)
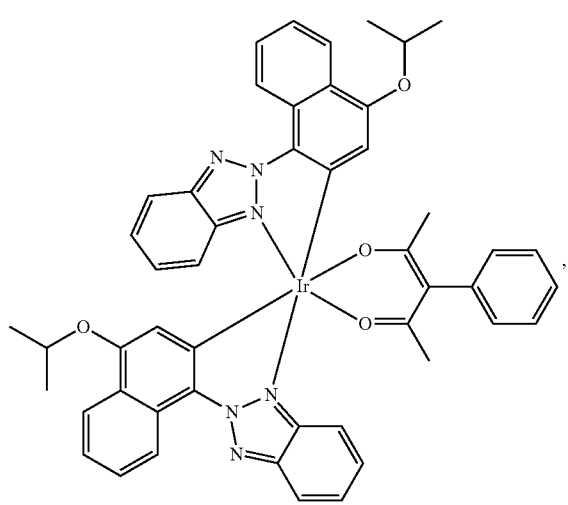
(B-284)

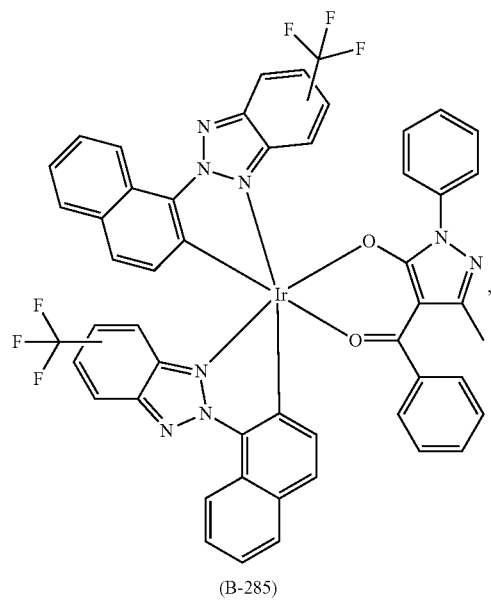
(B-285)
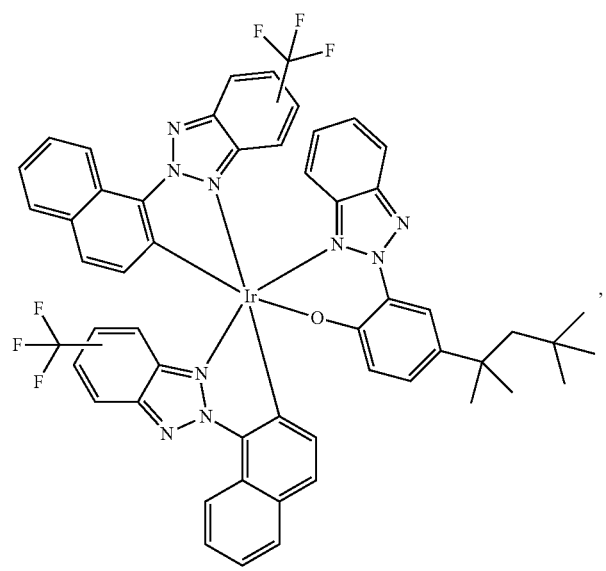
(B-286)

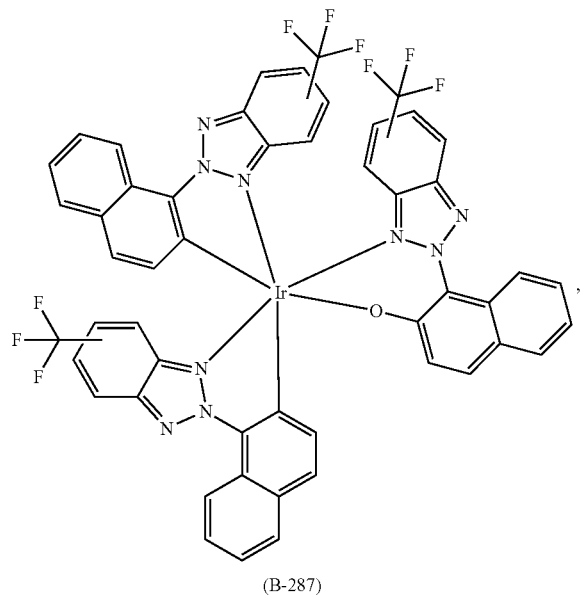
(B-287)
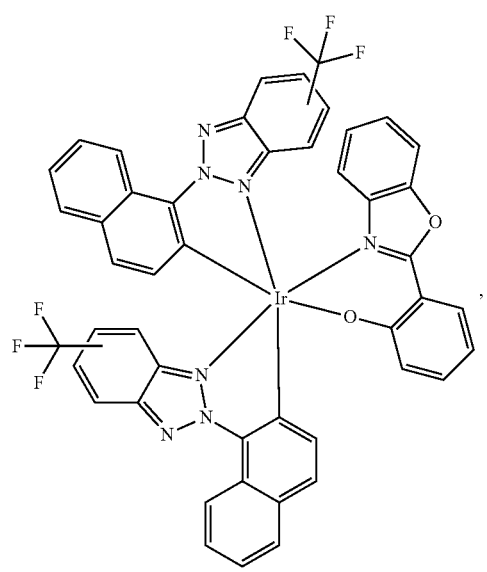
(B-288)

-continued
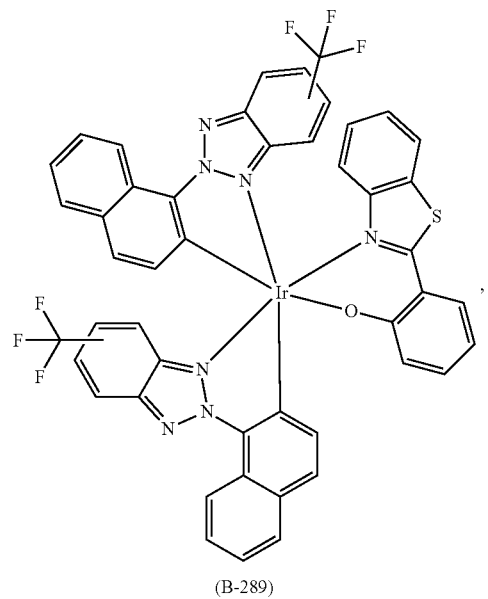
(B-289)
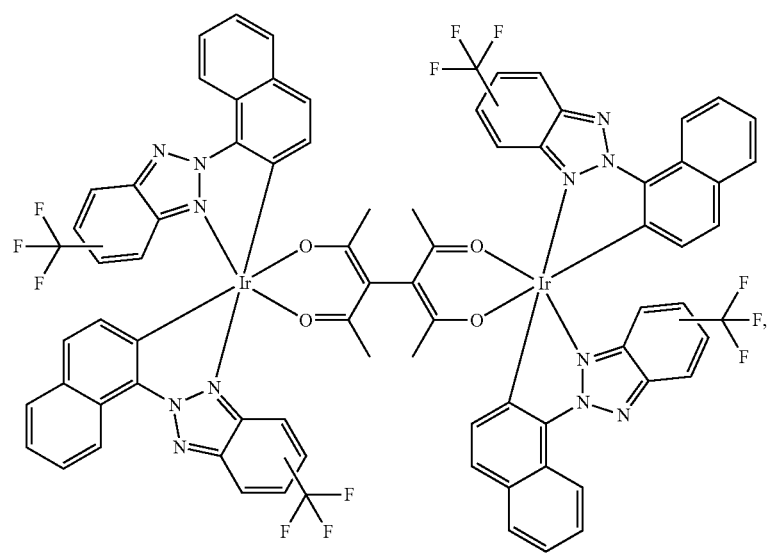
(B-290)

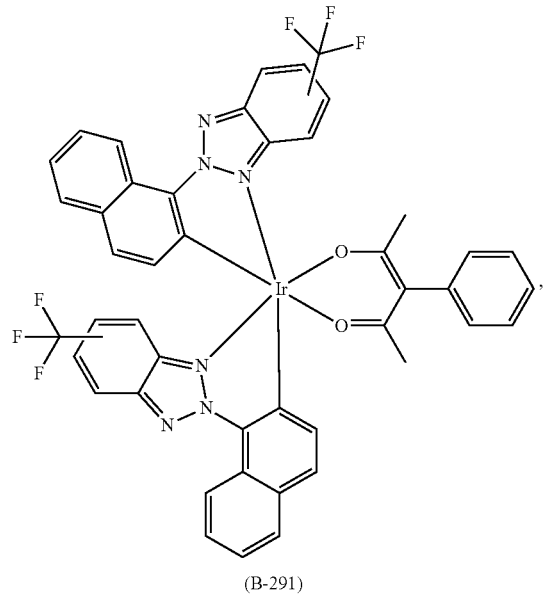
(B-291)
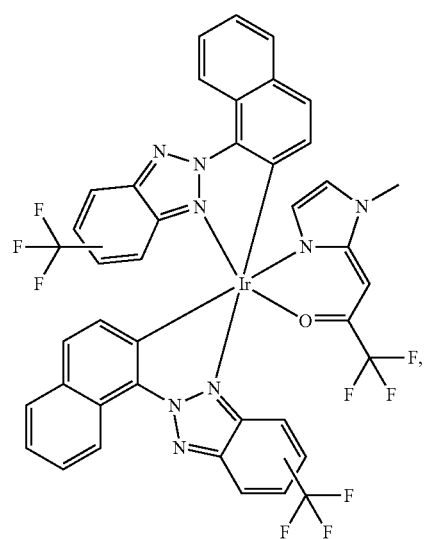
(B-292)

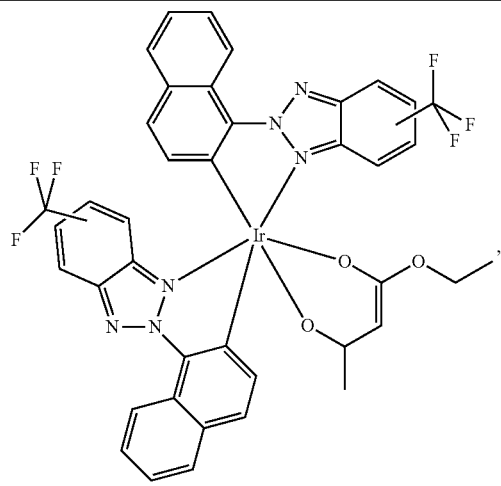
(B-293)
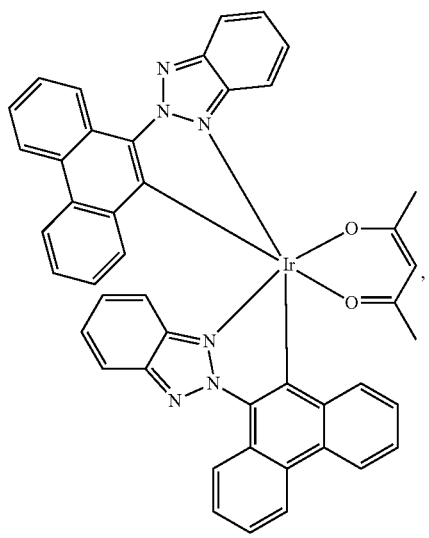
(E-1)
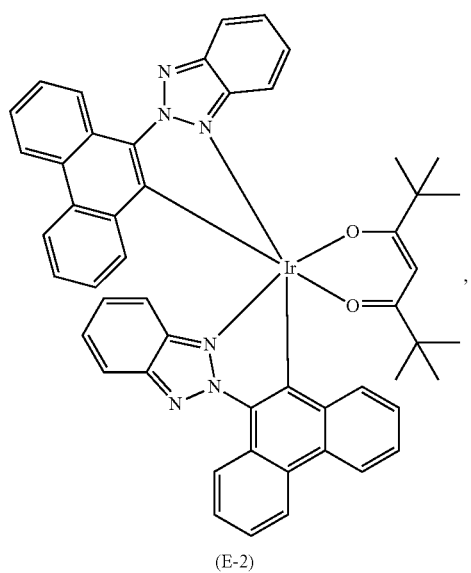
(E-2)

-continued
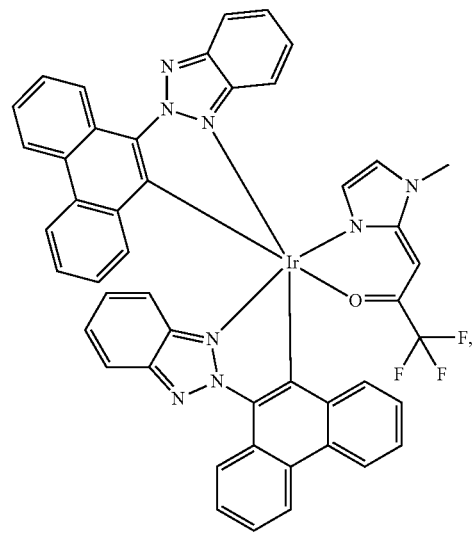
(E-3)
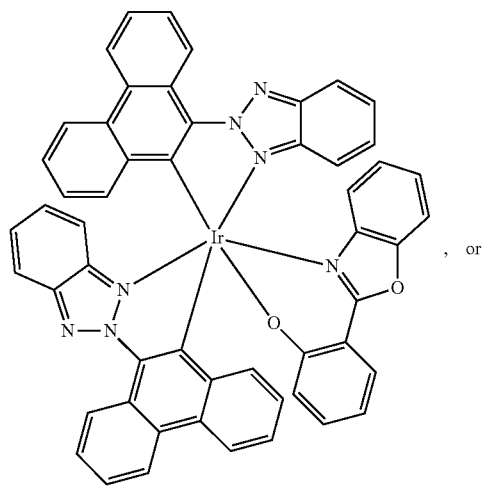
, or
(E-4)
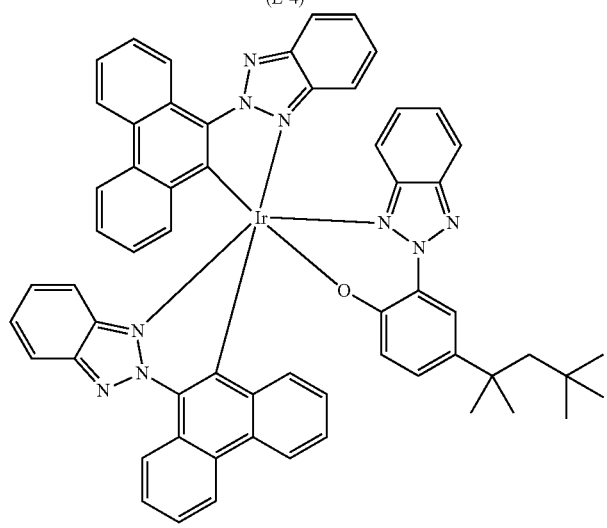
(E-5)

Examples of specific compounds of formula Va are compounds B-1 to B-89, B-99 to B-250, and B-254 to B-293. Special emphasis among them is given to compounds B-1, B-2, B-3, B-4, B-10, B-11, B-12, B-13, B-14, B-15, B-16, B-17, B-190, B-191, B-192, B-193, B-199, B-200, B-201, B-202, B-203 and B-204. Examples of specific compounds of formula Vb are compounds A-1 to A 44. Special emphasis among them is given to compounds A-1, A-2, A-3, A-4, A-10, A-11, A-12 and A-13. Examples of specific compounds of formula VIa are compounds E-1 to E 5.

Examples of specific compounds of formula VIIa are compounds D-1 to D-89 and D-99 to D-279. Special emphasis among them is given to compounds D-1, D-2, D-3, D-4, D-10, D11, D-12, D-13, D-235, D-236, D-244, D-245, D-246 and D-247. Examples of specific compounds of formula VIIb are compounds C-1 to C-44. Special emphasis among them is given to compounds C-1, C-2, C-10, C-11, C-12 and C-13.

The metal complexes of the present invention can be prepared according to usual methods known in the prior art. A convenient one-step method for preparing iridium metal complexes of formula $Ir(L_a)_3$

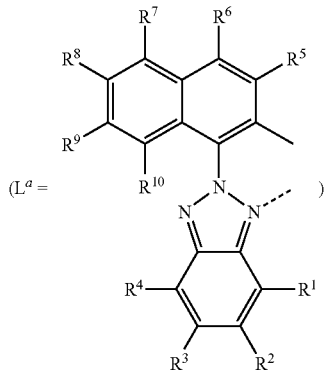

comprises reacting commercially available iridium trichloride hydrate with an excess of $L^aH$ in the presence of 3 equivalents silver trifluoroacetate and optionally in the presence of a solvent (such as halogen based solvents, alcohol based solvents, ether based solvents, ester based solvents, ketone based solvents, nitrile based solvents, and water). The tris-cyclometalated iridium complexes are isolated and purified by conventional methods. In some cases mixtures of isomers are obtained. Often the mixture can be used without isolating the individual isomers.

The iridium metal complexes of formula $Ir(L_a)_2L$ can, for example be prepared by first preparing an intermediate iridium dimer of formula

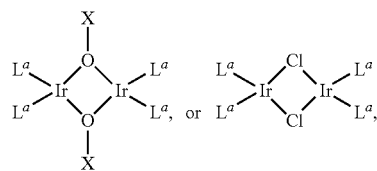

wherein X is H, methyl, or ethyl, and $L^a$ is as defined above, and then addition of HL. The iridium dimers can generally be prepared by first reacting iridium trichloride hydrate with $HL^a$ and adding NaX and by reacting iridium trichloride hydrate with $HL^a$ in a suitable solvent, such as 2-ethoxyethanol. The compounds of formula

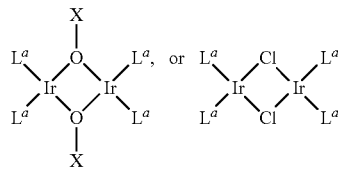

are new and form a further aspect of the present invention. Compounds of formula VIIa and VIIb can be synthesized, for example, as outlined in FIGS. 7 and 8 of U.S. Pat. No. 7,166,368.

Halogen is fluorine, chlorine, bromine and iodine.

$C_1$-$C_{24}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

$C_1$-$C_{24}$ perfluoroalkyl is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_4$-$C_{18}$cycloalkyl, especially $C_5$-$C_{12}$cycloalkyl, is preferably $C_5$-$C_{12}$cycloalkyl or said cycloalkyl substituted by one to three $C_1$-$C_4$alkyl groups, such as, for example, cyclopentyl, methyl-cyclopentyl, dimethylcyclopentyl, cyclohexyl, methylcyclohexyl, dimethylcyclohexyl, trimethyl-cyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred.

Examples of $C_4$-$C_{18}$cycloalkyl, which is interrupted by S, O, or $NR^{25}$, are piperidyl, piperazinyl and morpholinyl.

$C_2$-$C_{24}$alkenyl is for example vinyl, allyl, butenyl, pentenyl, hexenyl, heptenyl, or octenyl.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl. or 3-methyl-5-(1',1',3',3'-tetramethyl-butyl)-benzyl.

Heteroaryl is typically $C_2$-$C_{26}$heteroaryl, i.e. a ring with five to seven ring atoms or a condensed rig system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentyl thio, hexylthio, heptylthio, octylthio, decylthio, tetradecylthio, hexadecylthio or octadecylthio. $C_1$-$C_{24}$alkylselenium and $C_1$-$C_{24}$alkyltellurium are $C_1$-$C_{24}$alkylSe— and $C_1$-$C_{24}$alkylTe—, respectively.

Examples of a five or six membered ring formed by $R^9$ and $R^{10}$ and $R^{25}$ and $R^{26}$, respectively are heterocycloalkanes or heterocycloalkenes having from 3 to 5 carbon atoms which can have one additional hetero atom selected from nitrogen, oxygen and sulfur, for example

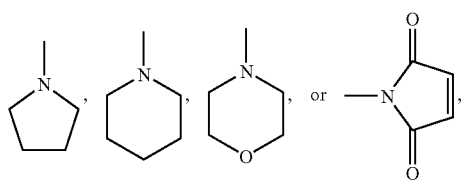

which can be part of a bicyclic system, for example

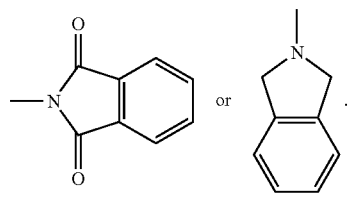

Possible substituents of the above-mentioned groups are $C_1$-$C_8$alkyl, a hydroxyl group, a mercapto group, $C_1$-$C_8$alkoxy, $C_1$-$C_8$alkylthio, halogen, especially fluorine, halo-$C_1$-$C_8$alkyl, especially fluoro-$C_1$-$C_8$alkyl, a cyano group, an aldehyde group, a ketone group, a carboxyl group, an ester group, a carbamoyl group, an amino group, a nitro group or a silyl group.

The term "haloalkyl" means groups given by partially or wholly substituting the above-mentioned alkyl group with halogen, such as trifluoromethyl etc. The "aldehyde group, ketone group, ester group, carbamoyl group and amino group" include those substituted by an $C_1$-$C_{24}$alkyl group, a $C_4$-$C_{18}$cycloalkyl group, an $C_6$-$C_{30}$aryl group, an $C_7$-$C_{24}$aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{105}R^{106}R^{107}$, wherein $R^{105}$, $R^{106}$ and $R^{107}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group.

If a substituent occurs more than one time in a group, it can be different in each occurrence.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex previously described.

In some embodiments, the active layer (c) may be substantially 100% of the metal complex because a host charge transporting material, such as $Alq_3$ is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material.

The device may include a support or substrate (not shown) adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e.g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent the anode. Both hole transporting small molecule compounds and polymers can be used. Commonly used hole transporting molecules, in addition to N,N'-diphenyl-N,N'-bis(3-methylphenyl)-[1,1'-biphenyl]-4,4'-diamine (TPD) and bis[4-(N,N-diethylamino)-2-methylphenyl] (4-methylphenyl)methane(MPMP), include: polyvinyl-carbazol, 1,1-bis[(di-4-tolylamino)phenyl] cyclohexane (TAPC); N,N'-bis(4-methylphenyl)-N,N'-bis(4-ethylphenyl)-[1,1,1-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-di-α-naphthyl-N,N'-diphenyl-4,4'-diphenyldiamine (α-NPD), and porphyrinic compounds, such as copper phthalocyanine.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, BAlq, $BAlq_2$(Appl. Phys. Lett. 89 (2006) 061111), CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, and printing. The active organic materials can be applied directly by vapor deposition processes, depending upon the nature of the materials.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-cheated oxinoid compounds (e.g., $Alq_3$ or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like; azole compounds (e.g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e.g., Li, Na, K, Rb, Cs), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer (s) may be present within organic electronic devices. For example, a layer (not shown) between the hole injecting layer (b) and the active layer (c) may facilitate positive charge transport, band-gap matching of the layers, function as a protective layer, or the like. Similarly, additional layers (not shown) between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group 1 metal and a layer of aluminum. The Group 1 metal may lie closer to the active layer (c), and the aluminum may help to protect the Group 1 metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer (d), the electron-hole recombination zone can lie within the $Alq_3$ layer. The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

In other embodiments, the phosphorus-containing metal complex compound can be used as a charge transport material in layer (b) or (d).

The compound does not need to be in a solid matrix diluent (e.g., host charge transport material) when used in layer (b) (e), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly (N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e.g., oxygen-sensitive indicators, phosphorescent indicators in bioassays, or the like).

The following examples illustrate certain features and advantages of the present invention. They are intended to be illustrative of the invention, but not limiting. All percentages are by weight, unless otherwise indicated.

EXAMPLES

Example 1

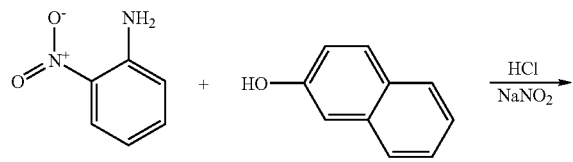

a) An orange suspension of 82.6 g (0.6 mol) of 2-nitroaniline and 600 ml of water is treated at room temperature under nitrogen with 153.6 g (1.56 mol) of 37%-hydrochlorid acid with simultaneous cooling to 0° C. A solution of 45.6 g (0.66 mol) of sodium nitrite in 240 ml of water is added to the orange suspension over 75 min at 0° C., and then further reacted for 3 h at the same temperature, giving a yellow solution. A solution of 11.7 g (0.12 mol) of sulfamic acid in 120 ml of water is added dropwise over 1 h at 0° C. The resulting yellow solution is transferred into a dropping funnel and added over 30 min at room temperature to a light brown solution of 90.8 g (0.63 mol) of 2-naphthol in 2'500 ml of ethanol, giving an orange suspension. Stirring is continued at room temperature during 19 h. The suspension is filtered, washed two times with 500 ml of ethanol, suspended in 1,000 ml of water, filtered, and washed two times with 500 ml of water, and two times with 500 ml of ethanol. The resulting orange solid is further dried under vacuum giving the title product as an orange-red powder (yield: 163.4 g (93%)). Melting point: 214.3-215.6° C.

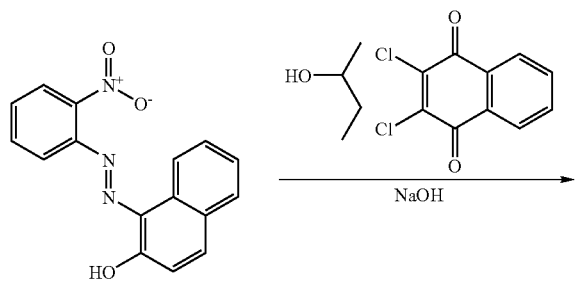

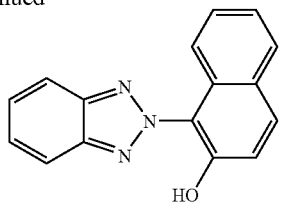

b) 88.0 g (0.3 mol) of the product of example 1a, 3.4 g (15 mmol) of 2,3-dichloro-1,4-naphthoquinone and 42 g (1.05 mol) of sodium hydroxide are dissolved under nitrogen in 170 ml of 2-butanol. The reddish black solution is heated up to reflux, and 100 ml of liquid are distilled off during 90 min. The reaction mixture is stirred for another 10 min at 96° C. 200 ml of 10%-aqueous hydrochloric acid are added first, followed by 300 ml of water. The organic phase is separated and 200 ml of ethyl acetate are added, and then washed with water (2×100 ml). Concentration of the organic phase leads to a dark solid which is dissolved in 400 ml of hot methanol. 500 ml of water are slowly added and the mixture stirred at room temperature during 30 min. The solid is filtered off and washed with 100 ml of water/methanol 1:1, dried under vacuum, giving the title product as a light grey powder (yield: 69.3 g (88.5%)). Melting point: 144.3-145.6° C.

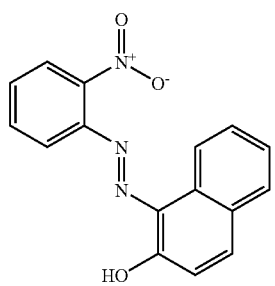

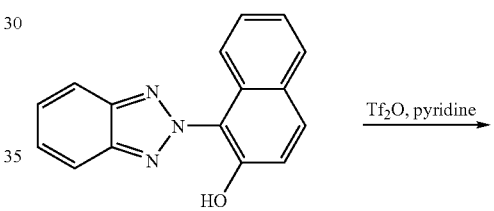

c) 39.2 g (0.15 mol) of the product of example 1b are dissolved under nitrogen in 300 ml of dichloromethane, and treated with 29.7 g (0.375 mol) of pyridine. 50.8 g (0.18 mol) of trifluoromethanesulfonic anhydride are slowly added during 15 min under cooling, and stirring continued for 30 min at room temperature. 100 ml of water are added, the organic phase separated and washed with 5%-aqueous hydrochloric acid. The organic phase is washed with water, followed by filtration over silica gel. The filtrate is concentrated and recrystallized from isopropanol/water 9:1. The resulting solid is filtered off, dried under vacuum, giving the title product as a light pink solid (yield: 49.1 g (83%)). Melting point: 147.0-148.3° C.

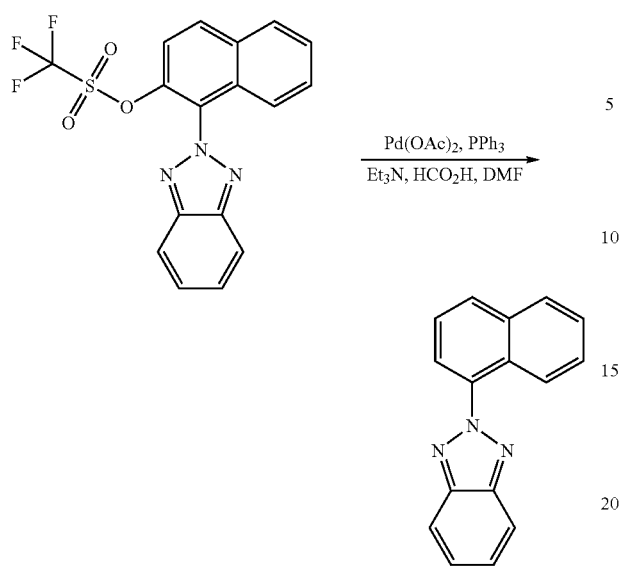

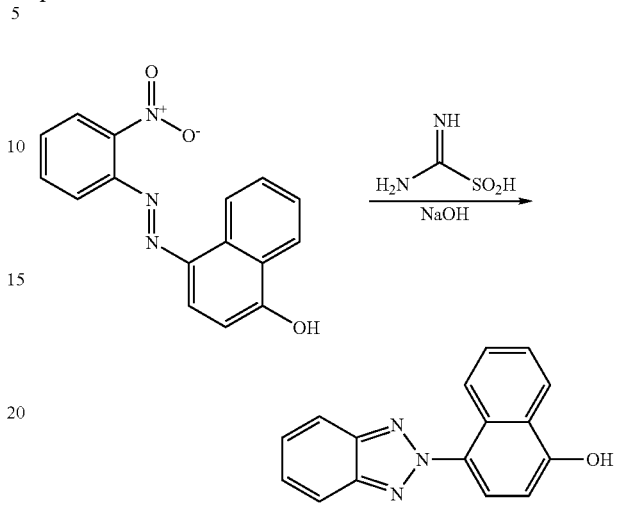

d) 130 g (0.33 mol) of the product of example 1c are dissolved under argon in 500 ml of N,N-dimethylformamide (DMF). The solution is treated with 1.5 g (6.6 mmol) of palladium(II) acetate, 3.5 g (13.2 mmol) of triphenylphosphine, and 100.2 g (0.99 mol) of triethylamine. 30.4 g (0.66 mol) of formic acid are added at 20° C. and the mixture slowly heated up to 85° C. during 30 min. After heating for another 30 min at the same temperature, the black reaction mixture is cooled down to room temperature and treated with 2,000 ml of ethyl acetate and 2,000 ml of water. 1,500 ml of toluene are added and the resulting mixture filtered over silica gel. The organic phase is separated and washed two times with 1,000 ml of water, dried over sodium sulfate, and concentrated under vacuum. The grey solid is dissolved in 1500 ml of hot tert-butylmethylether, filtered and cooled down over an ice-bath. The solid is filtered off, washed with cold tert-butylmethylether and dried under vacuum, giving the title product as a light beige solid (yield: 47.3 g (59%)). Melting point: 143.5-144.3° C.

Example 2

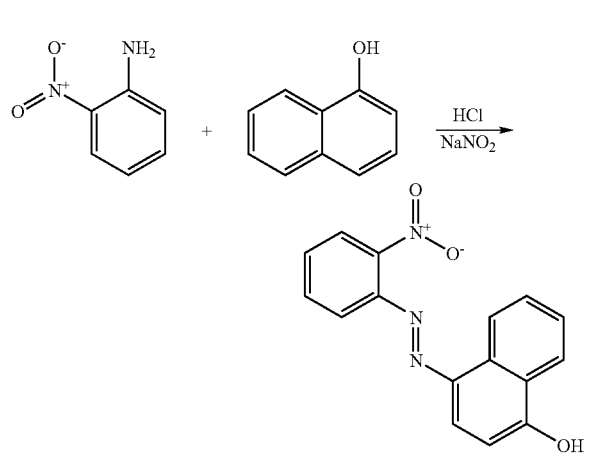

a) The title compound is prepared according to the procedure of example 1a, with 207.2 g (1.5 mol) of 2-nitroaniline, 227 g (1.58 mol) of 1-naphthol, 113.9 g (1.65 mol) of sodium nitrite, and 29.1 g (0.3 mol) of sulfamic acid, providing the title product as an orange solid (yield: 432.4 g (98%)). Melting point: 248.2-249.5° C.

b) 88 g (0.3 mol) of the product of example 2a and 55.2 g (1.38 mol) of sodium hydroxide are suspended at room temperature under nitrogen in 300 ml of ethanol and 600 ml of water and slowly heated up to 85° C. 90.8 g (0.84 mol) of formamidinesulfinic acid are suspended in water, and treated over an ice-bath with 33.6 g (0.84 mol) of sodium hydroxide, giving a colorless solution. The ice-cold, freshly prepared solution is added over 6 min to the preheated reaction mixture at 85° C., giving a yellow brown solution after complete addition. After 20 min heating the light beige solution is cooled down to room temperature and treated with 150 ml of 32%-hydrochloric acid. The resulting beige suspension is filtered, the solid dried under vacuum, followed by stirring in 2'500 ml of hexane. Filtration and drying gives the title product as a light beige powder (yield: 58.6 g (75%)). Melting point: 205.6-208.8° C.

c) 104.5 g (0.4 mol) of the product of example 2b is suspended at room temperature under nitrogen together with 52.8 g (0.8 mol) of powdered potassium hydroxide (purum, 85%) in 1,000 ml of N,N-dimethylformamide. 62.5 g (0.44 mol) of iodomethane are slowly added over 30 min. Stirring is continued for 25 min and the dark suspension poured into 2,000 ml under vigorous stirring. After 5 min, the resulting beige suspension is filtered, the solid washed with water (2×1,000 ml), suspended again in water, filtered, and washed Example 3

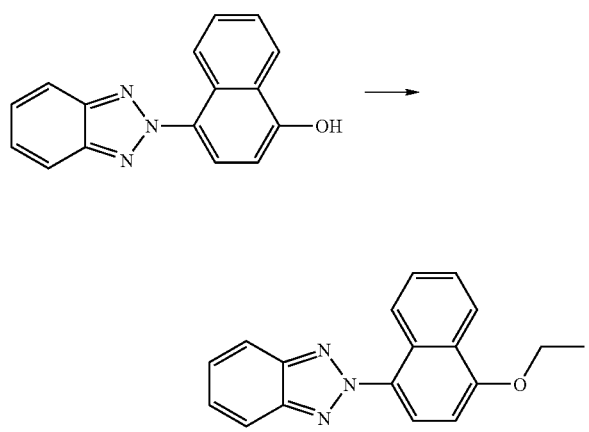

The title product is prepared according to the procedure of example 2c, with 5.22 g (0.02 mol) of the product of example 2b, 2.64 g (0.04 mol) of potassium hydroxide (purum, 85%), 50 ml of N,N-dimethylformamide, and 3.43 g (0.022 mol) of iodoethane. After suspending the crude product several times in water, and filtration, the beige solid is dissolved in 50 ml of isopropanol. Addition of 50 ml of hexane, cooling, filtration and drying gives the title product as a grey powder (yield: 5.6 g (97%)). Melting point: 124-125.3° C.

Example 4

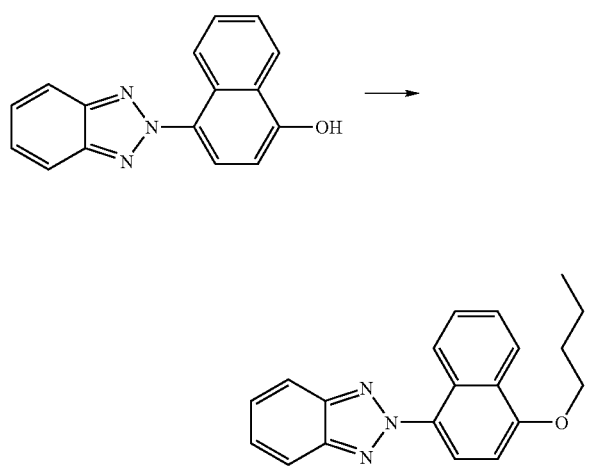

To 4.64 g (82.7 mmol) of potassium hydroxide (powder) in 65 ml of dimethylsulfoxide are added under nitrogen 5.40 g (20.7 mmol) of the product of example 2b. After 15 min 4.18 g (22.7 mmol) of 1-iodobutane are added. The reaction mixture is stirred for 3 h at room temperature. Water is added and the reaction mixture is extracted with diethyl ether. The organic phase is dried with magnesium sulphate and the solvent is removed. The product is filtered over silica gel with dichloromethane/hexane 2:1. Yield: 5.17 g.

Example 5

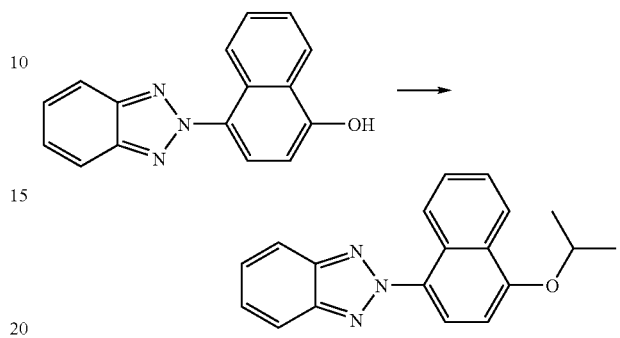

The title product is prepared according to the procedure of example 2c, with 39.2 g (0.15 mol) of the product of example 2b, 19.8 g (0.3 mol) of powdered potassium hydroxide (purum, 85%), 200 ml of N,N-dimethylformamide, and 28.1 g (0.165 mol) of 2-iodopropane. The reaction mixture is additionally heated during 2 h at 50° C. The resulting suspension is poured under strong stirring onto 500 ml of water, and after 5 min stirring extracted with ethyl acetate. The organic phase is washed three times with water, passed through a path of silica gel, and the silica gel rinsed with additional ethyl acetate. The eluent is concentrated under vacuum and the resulting solid recrystallized from hexane, giving the title product as a white solid (yield: 40.2 g (88%)). Melting point: 84.9-85.8° C.

Example 6

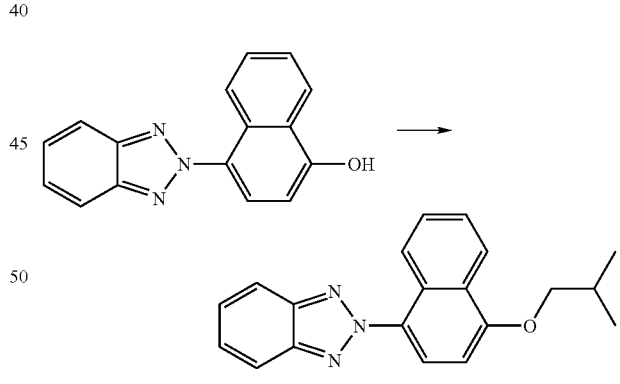

The title product is prepared according to the procedure of example 2c, with 5.2 g (0.02 mol) of the product of example 2b, 2.6 g (0.04 mol) of powdered potassium hydroxide (purum, 85%), 50 ml of N,N-dimethylformamide, and 4.1 g (0.022 mol) of 1-iodo-2-methylpropane. The resulting suspension is poured under strong stirring onto 300 ml of water, then treated with 32%-hydrochloric acid until a neutral pH is reached. The suspension is treated with ethyl acetate, and the organic phase washed three times with water. The organic phase is concentrated and the resulting solid dissolved in 100 ml of hot toluene. The solution is stirred at room temperature over night and the resulting solid filtered off, washed with with 500 ml water. Drying under vacuum gives the title product as light beige solid (yield: 106 g (96%)). Melting point: 131.5-133.0° C.

cold hexane giving the title product as a solid (yield: 4.3 g (67%)). Melting point: 119-119.9° C.

Example 7

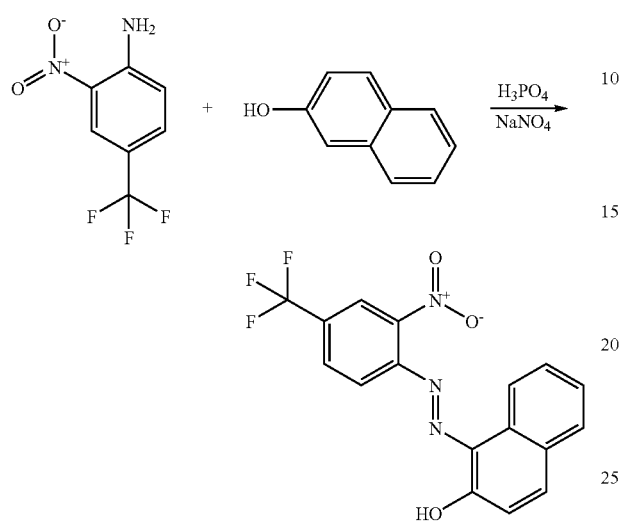

a) A yellow suspension of 103 g (0.5 mol) of 4-amino-3-nitrobenzotrifluoride is heated under nitrogen together with 900 ml of 85%-ortho-phosphoric acid to 50° C. and kept at this temperature for 75 min, and then cooled down to 0° C. A solution of 34.5 g (0.5 mol) of sodium nitrite in 80 ml of water is added over 25 min and stirred at 0° C. for 20 min. The resulting ice-cooled yellow suspension is transferred into a dropping funnel and slowly added under nitrogen to an ice-cooled yellow suspension of 75.7 g (0.525 mol) of 2-naphthol in 2'500 ml of methanol over 25 min. The orange suspension is filtered at room temperature and washed with methanol (3×500 ml), and suspended/filtered with water (4×1,000 ml). The remaining solid is dried under vacuum giving the title product as an orange powder (yield: 109 g (60%)). Melting point: 249.2-250.4° C.

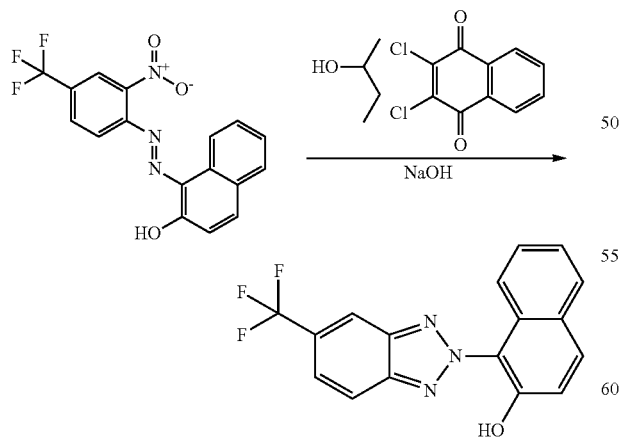

b) The title product is prepared according to the procedure of example 1b, with 36.1 g (0.1 mol) of the product of example 7a, 1.13 g (0.005 mol) of 2,3-dichloro-1,4-naphthoquinone, 16.0 g (0.4 mol) of sodium hydroxide in 750 ml 2-butanol. After addition of hydrochloric acid and water, the organic phase is separated, and washed with water (2×250 ml). The organic phase is concentrated and the resulting solid dissolved in 50 ml of ethyl acetate. 300 ml of hexane are added giving a fine suspension. The suspension is filtered over silica gel and the silica gel rinsed with additional hexane. The combined eluents are concentrated and dried under vacuum giving the title product as a solid (yield: 18.7 g (57%)). Melting point: 118.5-119.3° C.

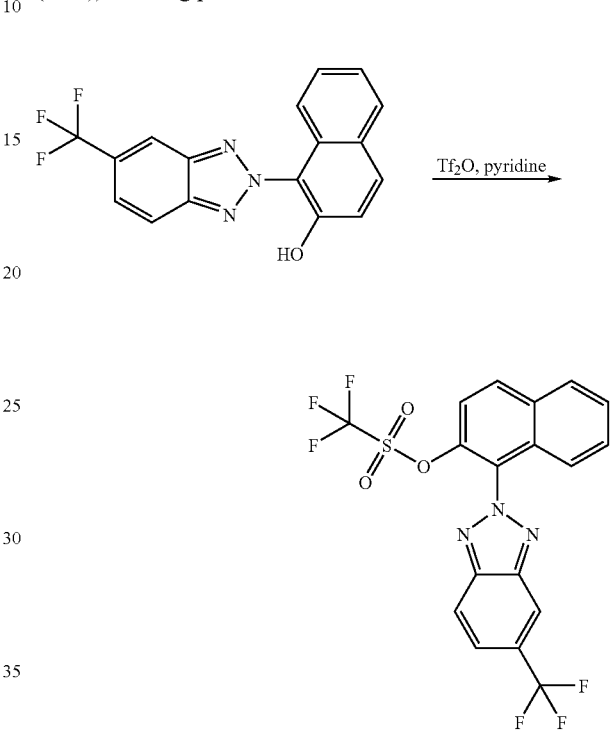

c) The title product is prepared according to the procedure of example 1c, with 58 g (0.176 mol) of the product of example 7b, 300 ml of dichloromethane, 34.8 g (0.44 mol) of pyridine and 59.5 g (0.211 mol) of trifluoromethanesulfonic anhydride. The reaction mixture is treated with 200 ml of water and diluted with 200 ml of dichloromethane. The organic phase is separated and washed with 100 ml of 5%-aqueous hydrochloric acid and water (2×150 ml), followed by filtration through silica gel. The filtrate is concentrated and dried under vacuum, giving the title compound as a brown solid (yield: 81 g (quant.)).

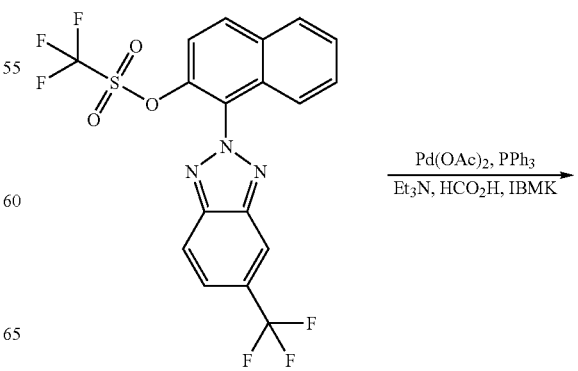

-continued

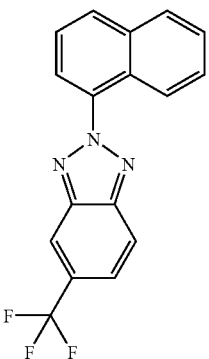

d) The title product is prepared according to the procedure of example 1d, with 78 g (0.169 mol) of the product of example 7c, 300 ml of isobutyl methyl ketone (IBMK) instead of N,N-dimethylformamide, 0.76 g (3.38 mmol) of palladium(II) acetate, 1.77 g (6.76 mmol) of triphenylphosphine, 51.3 g (0.507 mol) of triethylamine, and 15.6 g (0.338 mol) of formic acid. 10 g of activated charcoal are added after reaction and the mixture filtered, then diluted with 200 ml of ethyl acetate, and washed with water (3×200 ml). The organic phase is concentrated under vacuum giving a dark solid. The solid is dissolved in hot hexane, and heated during 15 min under reflux with 15 g of silica gel. The mixture is filtered and the filtrate cooled down to 0° C. After 1 h stirring at 0° C. the solid is filtered off and dried under vacuum, giving the title product as a light beige solid (yield: 28.6 g (54%)). Melting point: 106-107° C.

Example 8

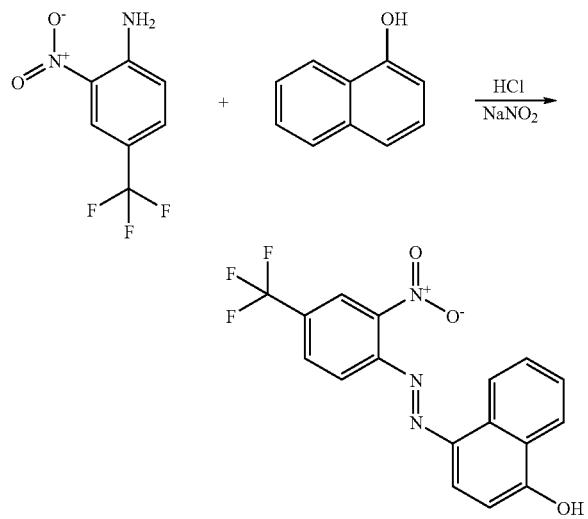

a) The title product is prepared according to the procedure of example 1a, with 42.0 g (0.2 mol) of 4-amino-3-nitrobenzotrifluoride in 200 ml of methanol and 51.2 g (0.52 mol) of 37%-hydrochlorid acid, with 15.2 g (0.22 mol) of sodium nitrite in 60 ml of water, with 1.9 g (0.02 mol) of sulfamic acid, and 30.3 g (0.21 mol) of 1-naphthol in 200 ml of ethanol. The crude reaction product is filtered and washed with a small amount of ethanol, then suspended with water (3×400 ml), filtered and the solid dried under vacuum, giving the title product as an orange powder (yield: 32.5 g (45%)). Melting point: 230-230.5° C.

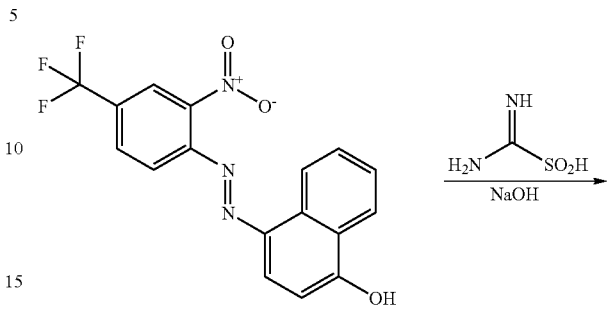

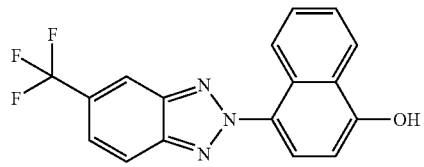

b) The title product is prepared according to the procedure of example 2b, with 18.0 g (0.05 mol) of the product of example 8a, 24.8 g (0.375 mol) of potassium hydroxide (85% content), 100 ml of ethanol, 150 ml of water, and 15.1 g (0.14 mol) of formamidinesulfinic acid. The crude reaction product is slightly acidified with diluted aqueous hydrochloric acid, and then put to a basic pH with aqueous sodium bicarbonate solution. The brownish product is extracted with ethyl acetate and the light brown organic phase concentrated under vacuum. The black solid is dissolved in dichloromethane and further purified by filtration over silica gel. The eluent is concentrated under vacuum giving the title product as a beige powder (yield: 9.2 g (56%)).

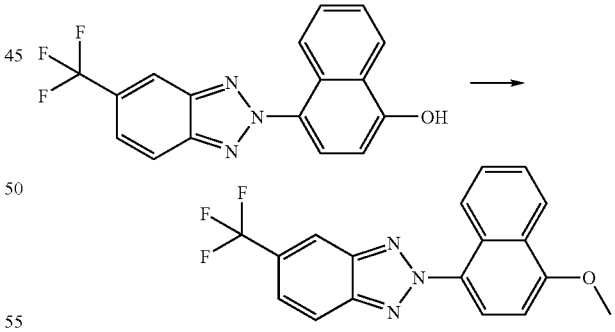

c) The title product is prepared according to the procedure of example 2c, with 8.2 g (0.025 mol) of the product of example 8b, 3.3 g (0.05 mol) of potassium hydroxide (85% content), 250 ml of N,N-dimethylformamide, and 3.9 g (27.5 mmol) of iodomethane. The crude reaction product is poured onto 200 ml of water, followed by extraction with ethyl acetate and washing with water. The organic phase is concentrated under vacuum. The resulting solid is dissolved in 20 ml of hot ethyl acetate, treated with 150 ml of hexane and 10 g of silica gel, and stirred during 15 min. Filtration and concentration gives the title product as a light brown powder (yield: 3.7 g (43%)). Melting point: 98.3-99.4° C.

Example 9

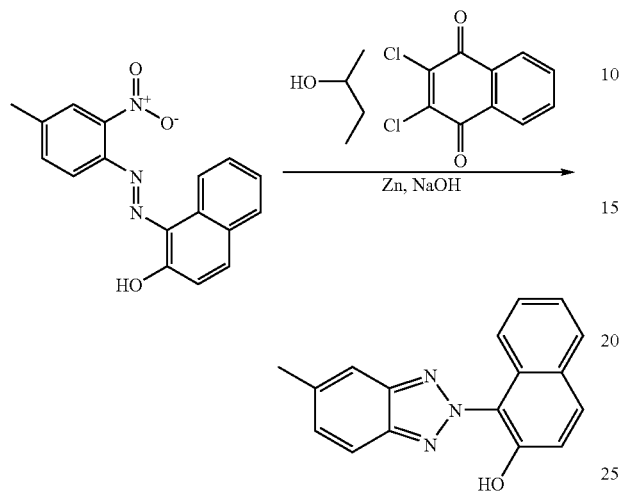

b) The title product is prepared according to the procedure of example 1b, with 61.4 g (0.2 mol) of Hansa-Scharlach RNC® (CAS 2425-85-6), 2.2 g (0.01 mol) of 2,3-dichloro-1,4-naphthoquinone, 28.0 g (0.7 mol) of sodium hydroxide in 1,000 ml of 2-butanol. After 150 min at 96° C. the reaction mixture is treated with 16.3 g (0.25 mol) of zinc and stirring continued for 90 min at 97° C. The hot reaction mixture is filtered, cooled down and acidified with diluted hydrochloric acid. The mixture is extracted with 1,000 ml of ethyl acetate and the organic phase washed with water (4×500 ml). The organic phase is concentrated under vacuum and the resulting solid further dried under vacuum at 70° C., giving the title product as dark colored solid (yield: 34.8 g (63%)). Melting point: 132.5-133.3° C.

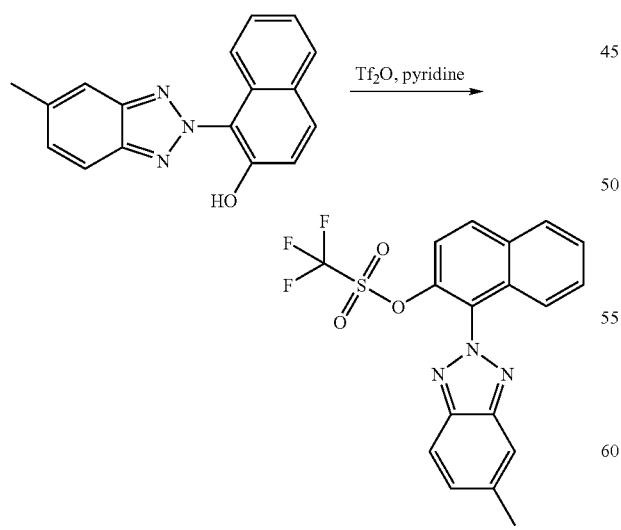

c) The title product is prepared according to the procedure of example 1c, with 33.9 g (0.123 mol) of the product of example 9b in 300 ml of dichloromethane, with 24.3 g (307.5 mmol) of pyridine and 41.6 g (147.6 mmol) of trifluoromethanesulfonic anhydride. The crude reaction mixture is poured onto 500 ml of water. The organic phase is separated, washed with water (2×300 ml), and concentrated under vacuum The title product is obtained as a dark solid (50 g (quant.)).

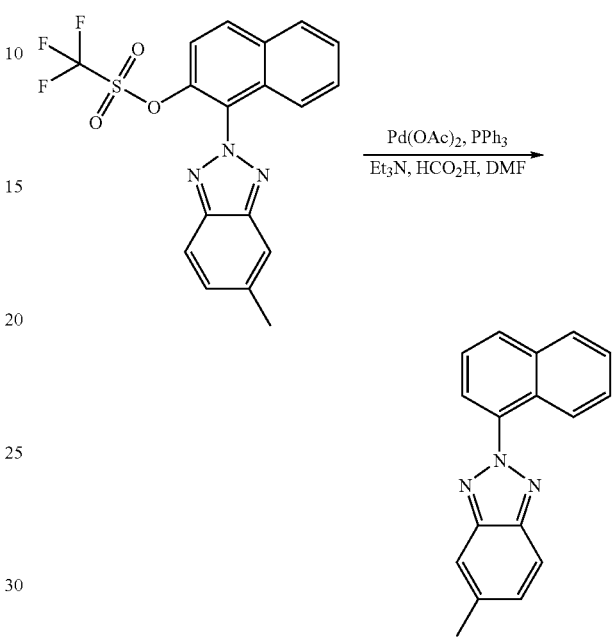

d) The title product is prepared according to the procedure of example 1d, with 50 g (0.122 mol) of the product of example 9c in 300 ml of N,N-dimethylformamide (DMF), 0.55 g (2.44 mmol) of palladium(II) acetate, 1.28 g (4.88 mmol) of triphenyl phosphine, 37 g (0.366 mol) of triethylamine, and 11.2 g (0.244 mol) of formic acid. The crude reaction product is cooled down, extracted with hexane (4×500 ml), the organic phase filtered over silica gel, and concentrated under vacuum, giving the title product as a beige powder (yield: 8.4 g (27%)). Melting point: 133.2-133.9° C.

Example 10

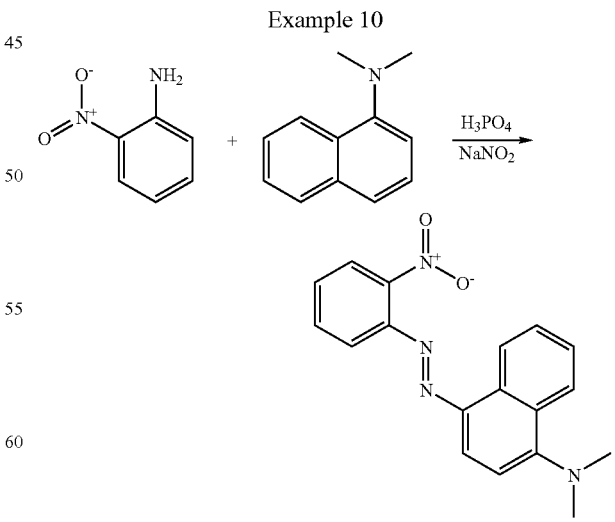

a) The title compound is prepared according to the procedure of example 7a, with 10.0 g (72.4 mmol) of 2-nitroaniline, 100 ml of 85%-ortho-phosphoric acid, with 5.00 g (72.4 mmol)) of sodium nitrite in water, and 13.0 g (76.0 mmol) of N,N-dimethyl-1-naphthylamine in 100 ml of methanol. The crude reaction mixture is poured into 300 ml of water, extracted with dichloromethane, dried, and concentrated under vacuum. Purification is done via flash chromatography (SiO$_2$, dichloromethane/hexane 2:1) giving the title product as a viscous oil (yield: 15.0 g (65%)).

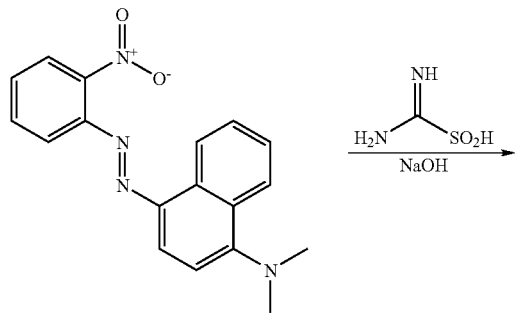

b) 17.47 g (0.687 mol) of sodium hydroxide are dissolved in 159 ml of water and treated with a solution of 11.0 g (34.3 mmol) of the product of example 10a in 159 ml of ethanol. The temperature is raised to 85° C. giving a clear solution. Stirring is stopped, the heating bath is removed, and 8.35 g (77.3 mmol) of formamidinesulfinic acid are added in two portions over 30 s. Stirring is slowly started again and the reaction mixture poured into ice-water after 1 h reaction time. The mixture is extracted with dichloromethane and the organic phase washed with water. The organic phase is concentrated under vacuum giving a slowly crystallizing product. Further purification is done via flash-chromatography over silica gel, giving the title compound as a solid (yield: 2.44 g (25%)).

Example 11

Alternative Method for the Preparation of Example 1

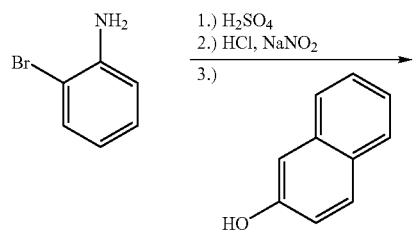

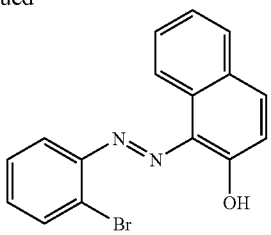

a) To 10.0 g (58.1 mmol) of 2-bromoaniline in 100 ml of ethanol are added 5.76 g (58.7 mmol) of sulphuric acid. The solvent is distilled off. The solid is dissolved in 150 ml water and 5.3 ml 32% HCl. The reaction mixture is cooled to 0° C. and an ice-cold solution of 4.01 g (58.1 mmol) of sodium nitrite in 25 ml water is slowly added. The reaction mixture is stirred at 0° C. for 2 h and added slowly to an ice-cold solution of 8.38 g (58.1 mmol) of 2-naphthol in 300 ml of ethanol. After 2 h stirring at room temperature 500 ml of dichloromethane and 200 ml of water are added and the water phase is separated. The organic phase is washed two times with water, dried with sodium sulphate, and concentrated under vacuum, giving the title product (yield: 18.3 g (94%)).

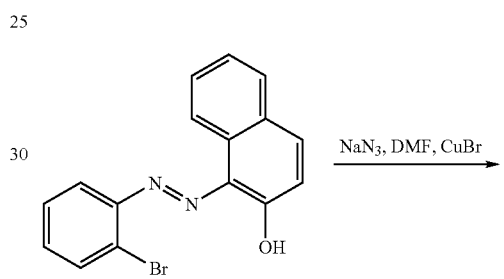

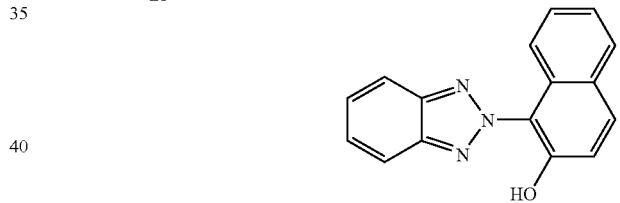

b) 1.00 g (2.97 mmol) of the product of example 11a, 0.19 g (2.97 mmol) of sodium azide and 5 mg of copper(I) bromide are suspended under nitrogen in 10 ml of N,N-dimethylformamide (DMF). The reaction mixture is stirred for 8 h at 80° C. Additional 0.19 g of sodium azide are added and the reaction mixture is heated for 2 h at 80° C. Water is added and the reaction mixture is extracted with dichloromethane. The organic phase is extracted with a 10%-sodium hydroxide solution. The water phase is acidified with 32%-hydrochloric acid and extracted with dichloromethane. The organic phase is washed with water, dried with magnesium sulphate, filtered, and concentrated under vacuum, giving the title product (yield: 530 mg (68%)). Reference is made to *Journal of Organic Chemistry* 1968, 33, 7, 2954.

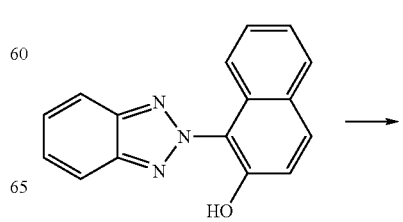

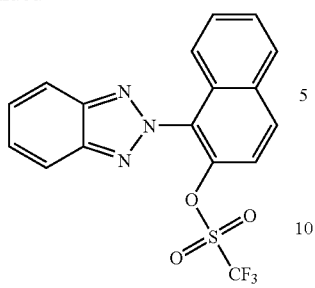

c) To 5.00 g (19.1 mmol) of the product of example 11b in 60 ml of dichloromethane and 3.78 g (47.4 mmol) of pyridine, 6.48 g (23.0 mmol) of trifluoromethanesulfonic anhydride are added dropwise under nitrogen. The reaction mixture is stirred for 1 h at 25° C., washed with water, dried with magnesium sulphate, and concentrated under vacuum, giving the title product as a white solid (yield: 7.36 g (98%)).

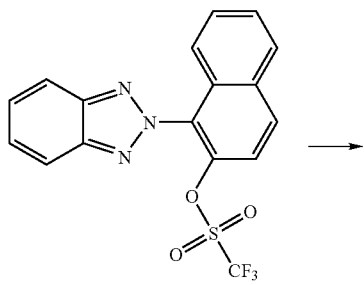

d) 7.30 g (18.5 mmol) of the product of example 11c, 5.63 g (55.7 mmol) of triethylamine, 80 mg (0.37 mmol) of palladium(II) acetate, 190 mg (0.74 mmol) of triphenylphosphine are dissolved under nitrogen in 29 ml of N,N-dimethylformamide (DMF). The reaction mixture is degassed and 1.71 g (37.1 mmol) of formic acid are added dropwise. The reaction mixture is stirred at 80° C. for 150 min. Water is added and the water phase is extracted with ethyl acetate. The organic phase is dried with magnesium sulphate and the solvent is distilled off. The product is crystallized two times from methanol. Yield: 1.80 g (40%).

Example 12

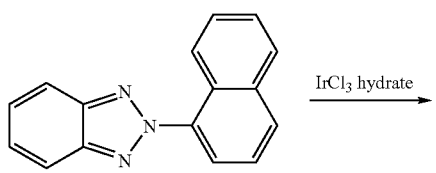

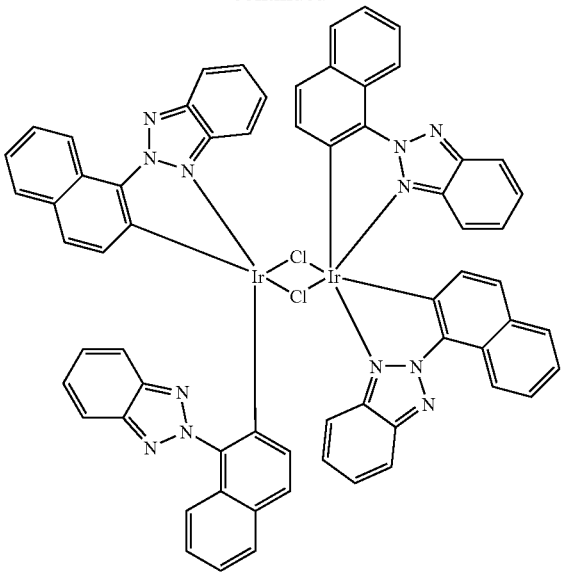

40.0 g (0.163 mol) of the product of example 1d and 29.9 g (81.5 mmol) of iridium(III)-chloride hydrate (52.46% iridium-content) are suspended at room temperature under argon in a mixture of 1,000 ml of 2-ethoxyethanol and 300 ml of water. The reaction mixture is heated up to 110° C. and kept at this temperature for 22 h. The dark red suspension is cooled down to room temperature, filtered, washed with absolute ethanol, and dried under vacuum. The title product is obtained as a brownish red powder (yield: 55.5 g (95%)).

Example 13

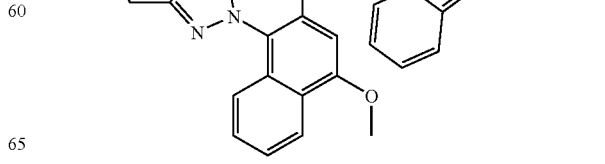

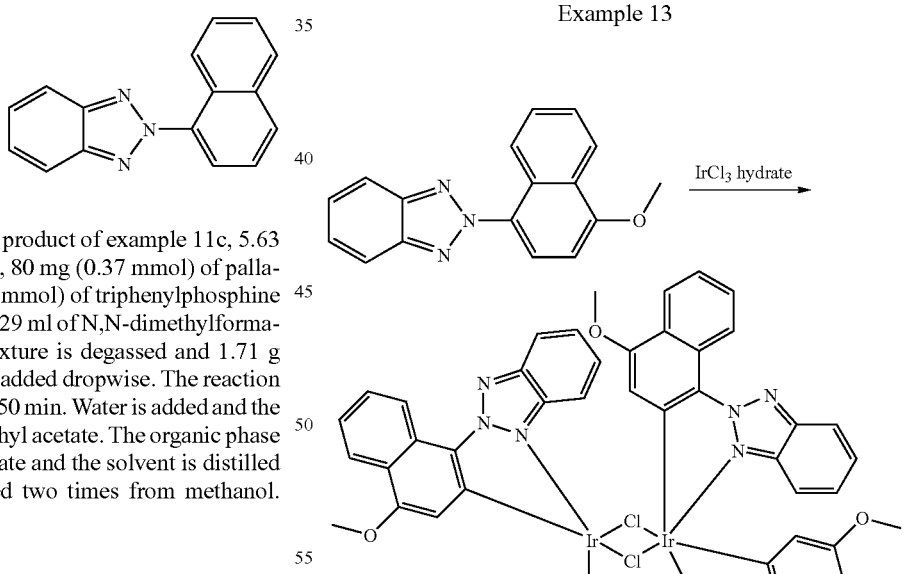

16.5 g (0.06 mol) of the product of example 2c and 10.5 g (28.6 mmol) of iridium(III)chloride hydrate (52.42% iridium-content) are suspended at room temperature under nitrogen in a mixture of 300 ml of 2-ethoxyethanol and 100 ml of water. The grey-black reaction mixture is heated up to 110° C. and kept at this temperature for 21 h. The dark red suspension is cooled down to room temperature, filtered, washed with absolute ethanol, and dried under vacuum. The title product is obtained as a brownish red powder (yield: 19.74 g (89%)).

Example 14

Please note, a ligand

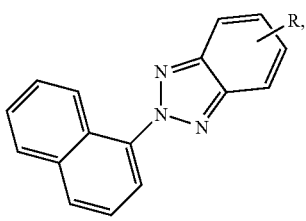

wherein R is, for example, $CF_3$, or $CH_3$, can coordinate in to different ways to iridium. The two possibilities

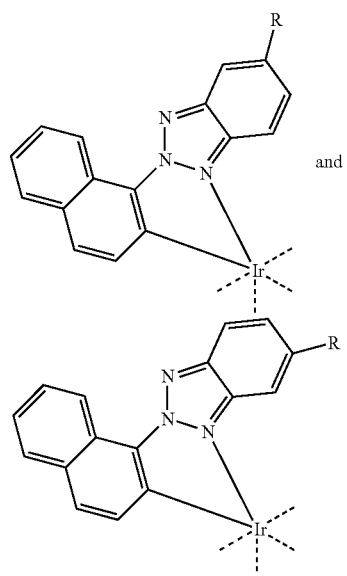

are represented by the following notation

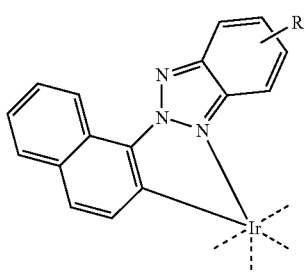

throughout the examples to simplify matters.

21 g (67 mmol) of the product of example 7d and 11.6 g (31.9 mmol) of iridium(III)chloride hydrate (52.84% iridium-content) are suspended at room temperature under nitrogen in a mixture of 250 ml of 2-ethoxyethanol and 75 ml of water. The grey-black reaction mixture is heated up to 110° C. and kept at this temperature for 22 h. The dark red suspension is cooled down to room temperature, filtered, washed with absolute ethanol, and dried under vacuum. The title product is obtained as a red powder (yield: 22.3 g (82%)).

Examples 15-21

The following diiridium complexes are prepared according to the procedure reported for example 12, giving the products of examples 15-21. The respective m/z-values of the product structures have been detected by HPLC-MS measurements.

| Example | Ligand | Diiridium complex |
|---|---|---|
| 15 | 3d | 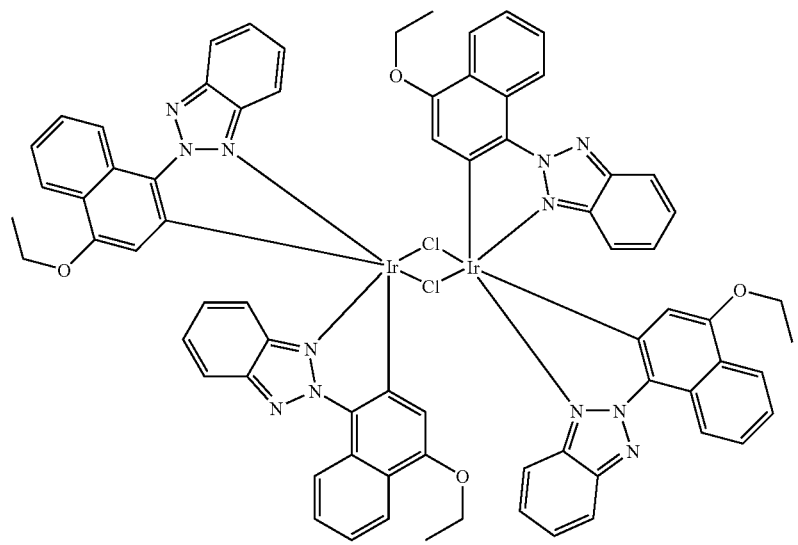 |
| 16 | 4 | 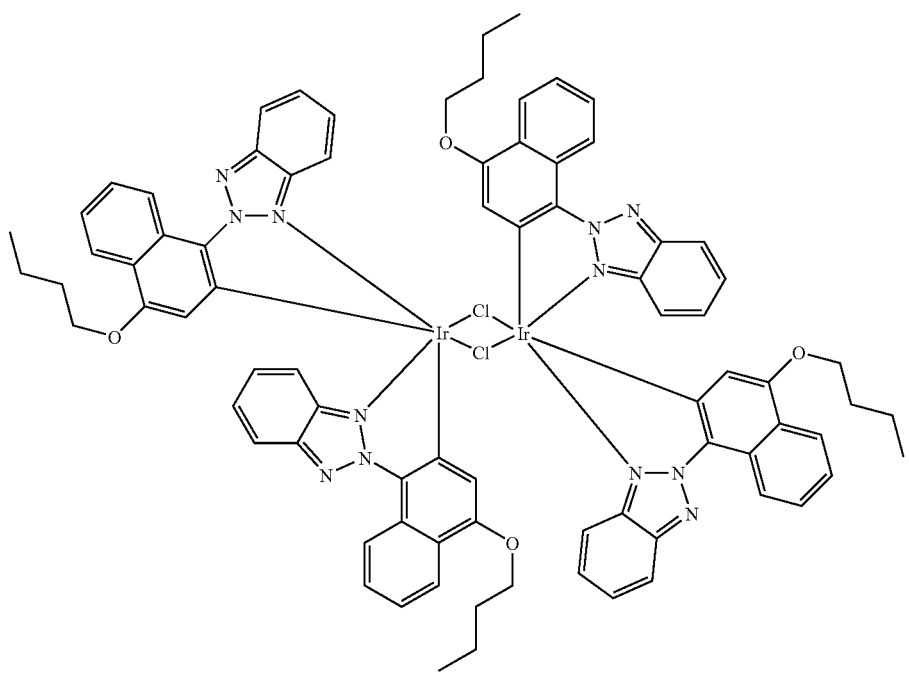 |

-continued
| Example | Ligand | Diiridium complex |
|---|---|---|
| 17 | 5 | 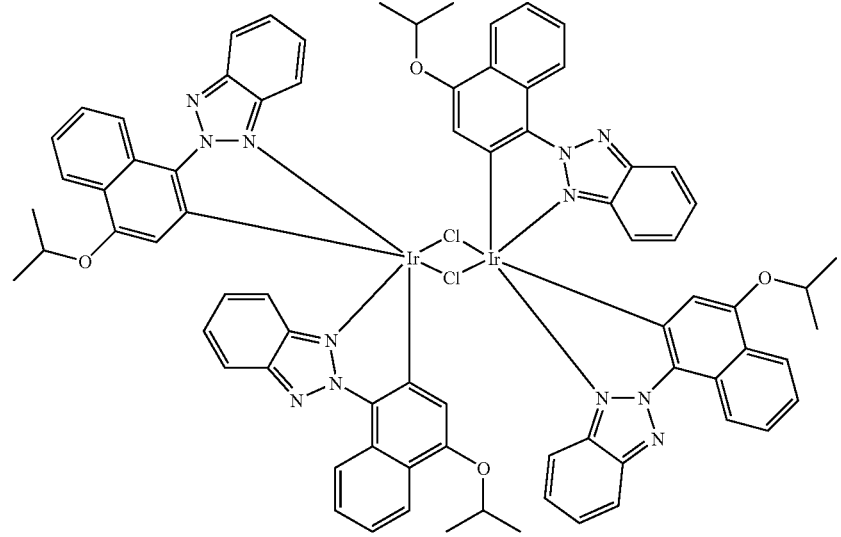 |
| 18 | 6 | 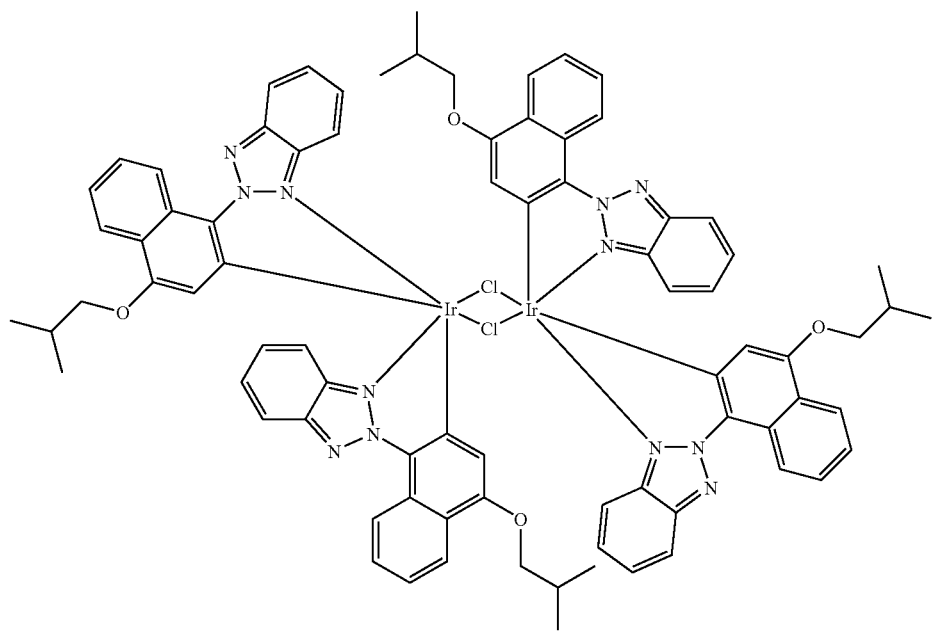 |

-continued
| Example | Ligand | Diiridium complex |
|---------|--------|-------------------|
| 19 | 8d | 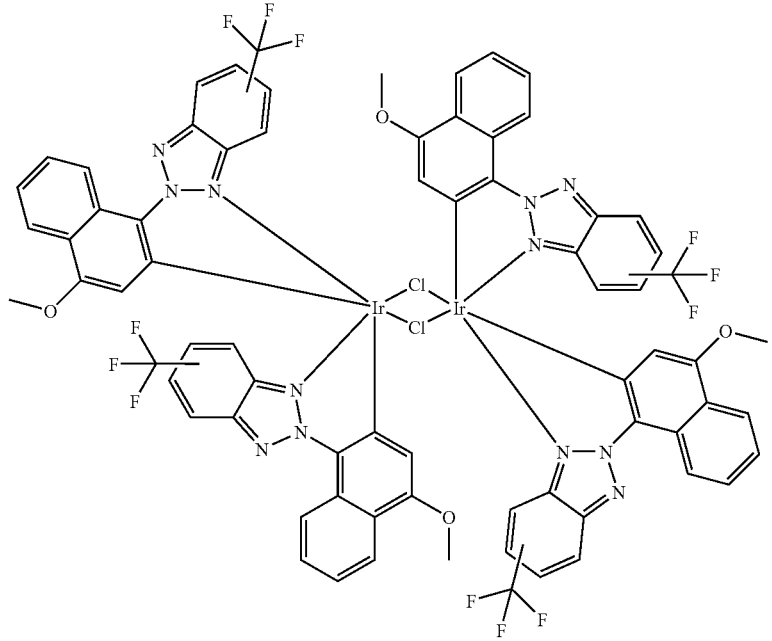 |
| 20 | 9d | 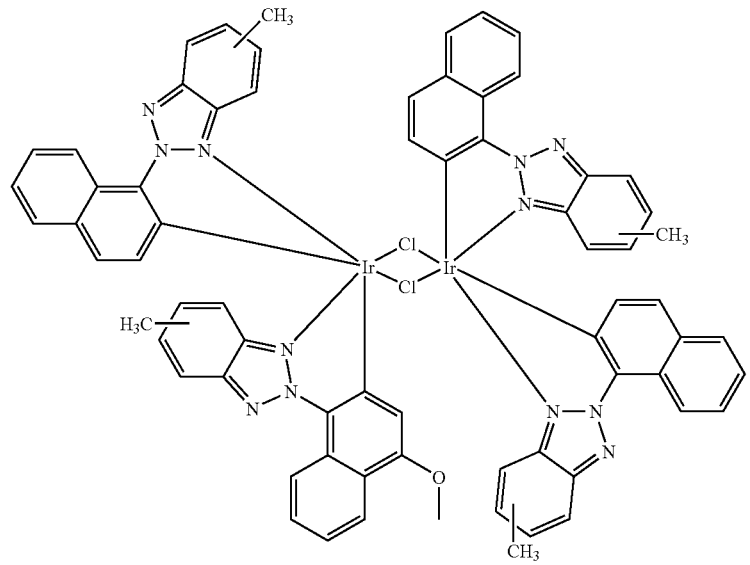 |

| Example | Ligand | Diiridium complex |
|---|---|---|
| 21 | 10b | 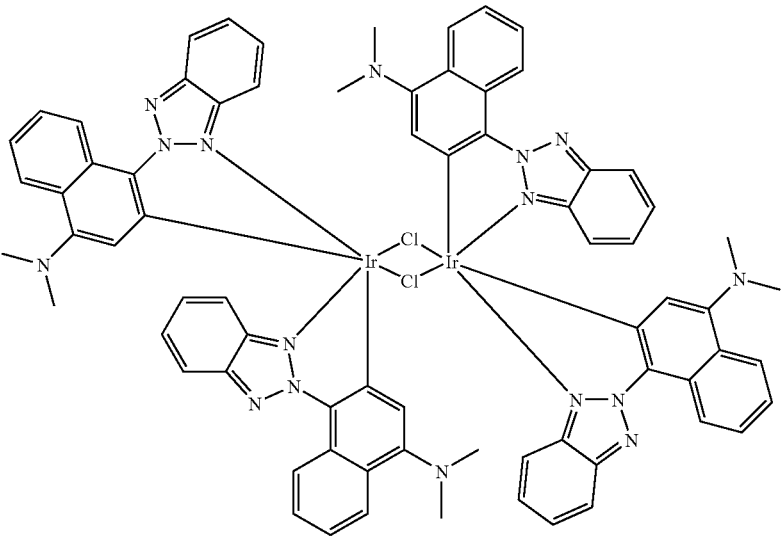 |
Example 22
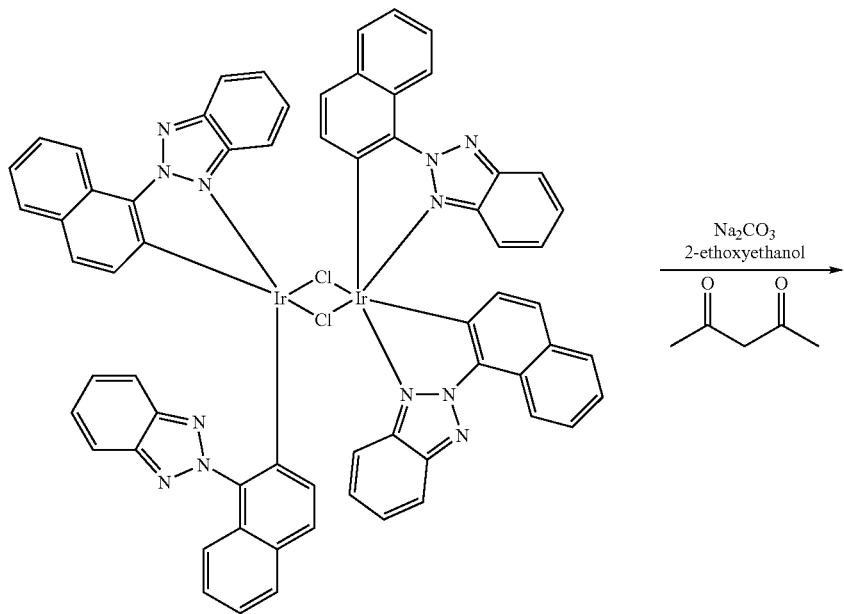

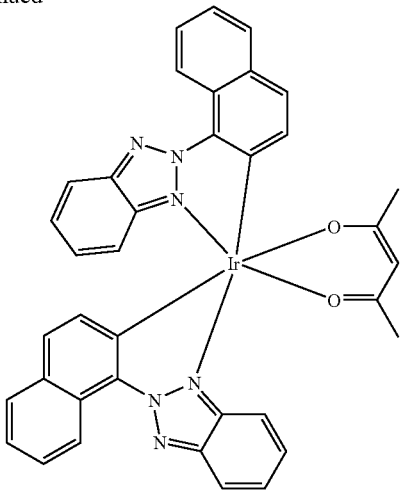

To 2.00 g (1.40 mmol) of the product of example 12 are added under argon 980 mg (9.22 mmol) of sodium carbonate and 66 ml of 2-ethoxyethanol. The suspension is evacuated and put under argon three times. 360 mg (360 mmol) of acetyl acetone are added. The reaction mixture is refluxed under argon for 18 h. The product is filtered off, dissolved in dichloromethane and filtered over silica gel. The solvent is removed and 50 ml of ethoxyethanol are added. The suspension is refluxed for 1 h. The product is filtered off and dried under vacuum, giving the title product as orange-red powder (yield: 1.56 g (72%)).

Example 23

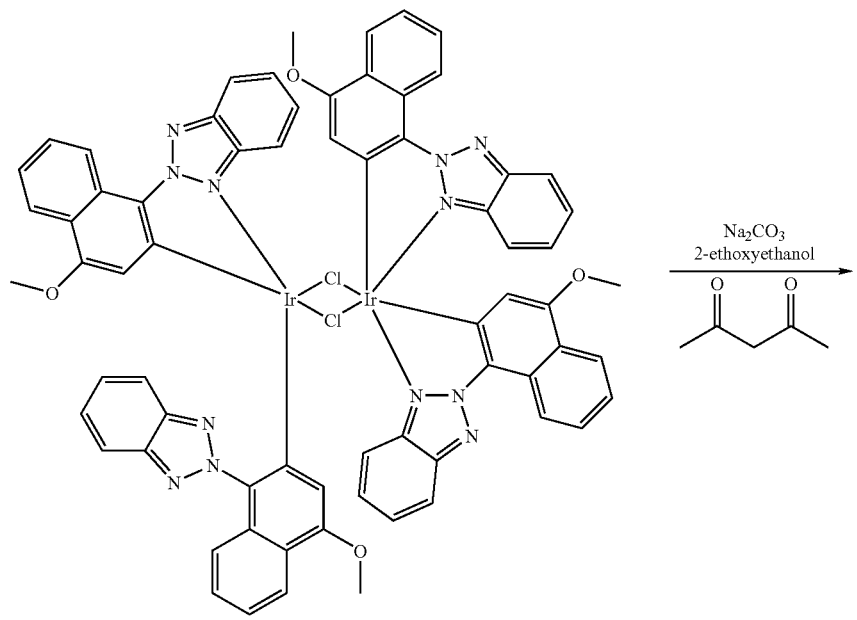

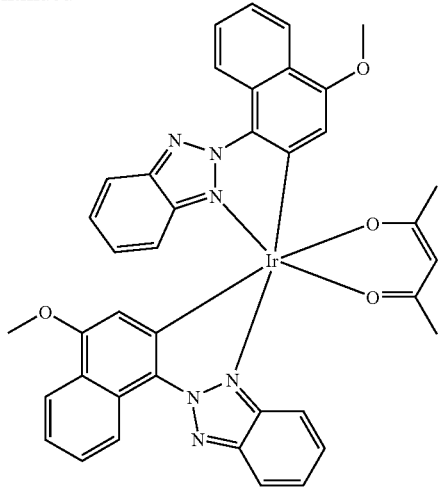

25 g (16.1 mmol) of the product of example 13 and 11.3 g (106 mmol) of sodium carbonate are suspended under argon in 500 ml of 2-ethoxyethanol. The suspension is evacuated and put under argon three times. 4.2 g (41.9 mmol) of acetylacetone are added and the orange suspension heated up to 100° C. and kept at this temperature for 1 h. The reaction mixture is cooled down to room temperature and washed with 200 ml of ethanol, suspended several times with water and washed extensively with ethanol. The resulting solid is dried under vacuum giving the title compound as an red powder (yield: 23.5 g (87%)).

Example 24

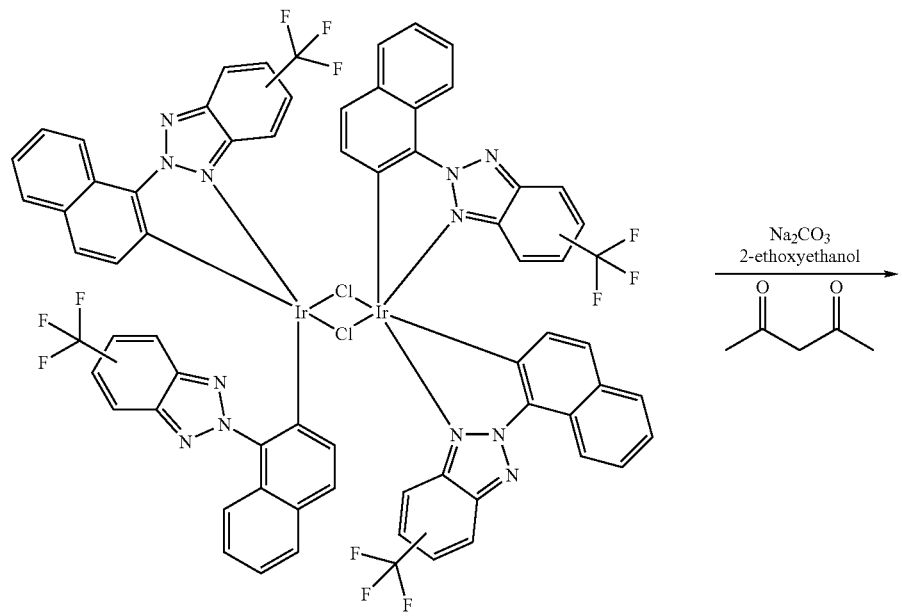

-continued

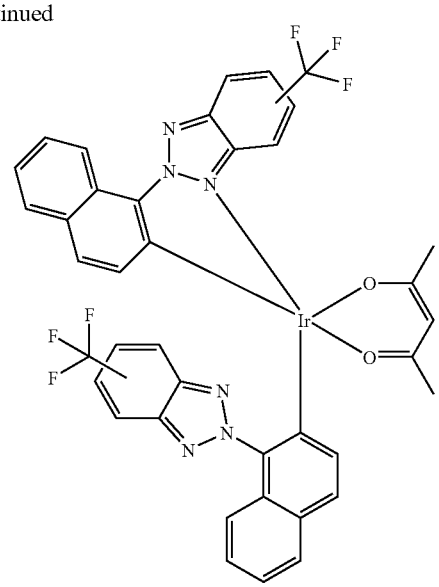

18 g (10.6 mmol) of the product of example 14 and 7.4 g (0.07 mol) of sodium carbonate are suspended under argon in 100 ml of 2-ethoxyethanol. The suspension is evacuated and put under argon three times. 5.5 g (55 mmol) of acetylacetone are added and the orange suspension heated up to 100° C., and kept at this temperature for 45 min. 0.5 g of acetyl acetone are added, and heating continued for 30 min. The reaction mixture is cooled down to room temperature and washed with 200 ml of ethanol, suspended several times in water and washed with ethanol. The resulting solid is dried under vacuum giving the title compound as a red powder (yield: 18.5 g (96%)).

Examples 22-96

The iridium complexes are prepared according to Example 24, with the respective ancillary ligands given in the table below, instead of acetyl acetone, starting from the products of examples 12-21. In the case of the iridium complexes of examples 35, 45, and 87, preparation has been done according to the procedure of Example 12 in WO2006/000544, from the respective diiridium complexes as starting material (products from examples 12-21), with silver trifluoromethane sulfonate in acetone or 2-nonanone, and the respective ancillary ligand given in the table below. The respective m/z-values of the product structures have been detected by HPLC-MS measurements. All photoluminescence (PL) spectra were measured with a Perkin Elmer Luminance Spectrometer LS 50 B. Materials were dissolved in toluene, and the solution purged with nitrogen in a sealed cuvette. Excitation of the solutions was done at various wavelengths dependent on the absorption characteristics which were measured before PL measurement was carried out using the same cuvettes and solutions. The spectrometer is equipped with two different lamps and covers a wavelength range from 250-800 nm. Colour coordinates CIE x,y were determined from PL spectra and calculated by a software provided with the spectrometer.

| Ex. | Compound HL | Iridium complex | CIE x, y |
|---|---|---|---|
| 22 | 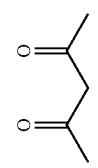 | 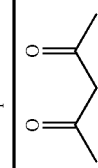 (B-1) | 0.62, 0.37 |
| 23 | 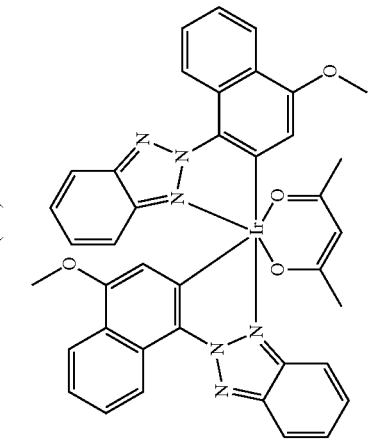 | 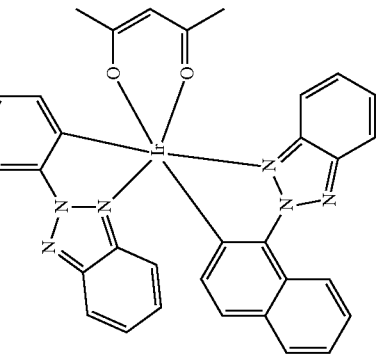 (B-2) | 0.63, 0.36 |

-continued
| Ex. | Compound HL | Iridium complex | CIE x, y |
|---|---|---|---|
| 24 | 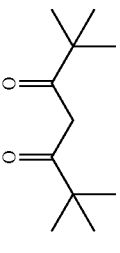 | 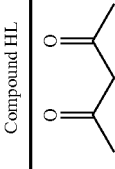 (B-11, B-11) | 0.66, 0.33 |
| 25 | 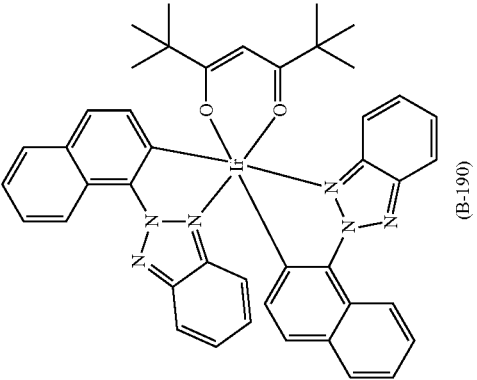 | 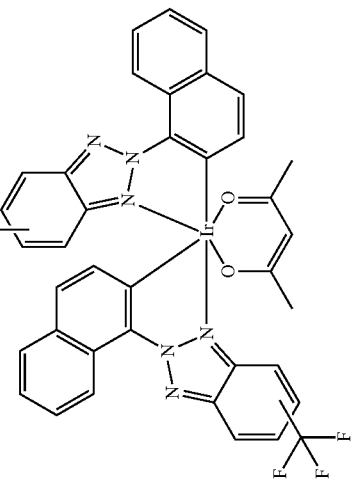 (B-190) | 0.62, 0.37 |

| Ex. | Compound HL | Iridium complex | CIE x, y |
|---|---|---|---|
| 26 | 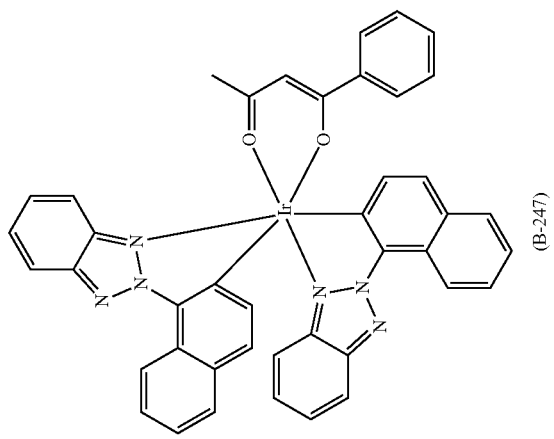 | 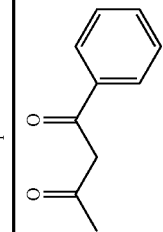 (B-247) | 0.63, 0.37 |

-continued
| Ex. | Compound HL | Iridium complex | CIE x, y |
|---|---|---|---|
| 27 | 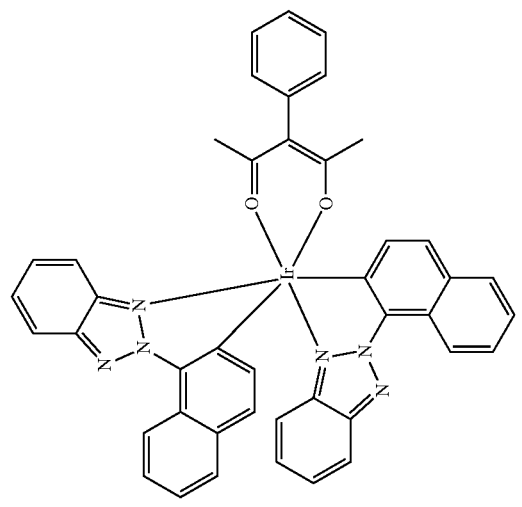 | 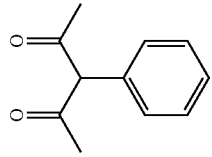 (B-248) | 0.62, 0.37 |

| Ex. | Compound HL | Iridium complex | CIE x, y |
|---|---|---|---|
| 28 | (1,3-diphenyl-1,3-propanedione structure) | (B-249) | 0.62, 0.37 |
| 29 | (2-acetyl-1-tetralone structure) | (B-250) | 0.62, 0.37 |

-continued

| Ex. | Compound HL | Iridium complex | CIE x, y |
|---|---|---|---|
| 30 | (isoquinoline-1-carboxylic acid structure) | (B-251) | 0.60, 0.39 |
| 31 | (quinoline-2-carboxylic acid structure) | (B-252) | 0.59, 0.40 |

-continued
| Ex. | Compound HL | Iridium complex | CIE x, y |
|---|---|---|---|
| 32 | 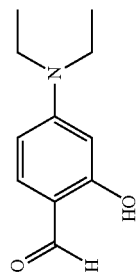 | 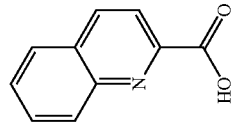 (B-253) | 0.61, 0.38 |
| 33 | 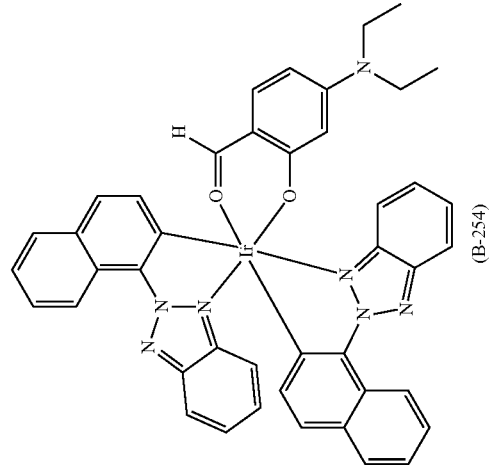 | 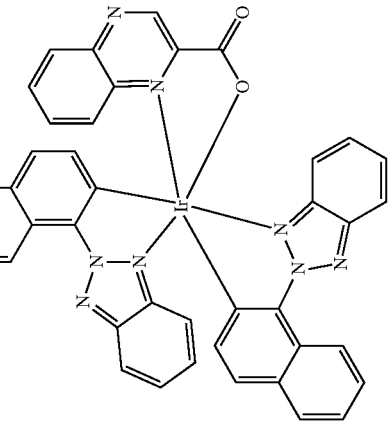 (B-254) | 0.62, 0.37 |

-continued

| Ex. | Compound HL | Iridium complex | CIE x, y |
|---|---|---|---|
| 34 | (1-methylimidazol-2-yl trifluoromethyl ketone enol form) | (B-255) | 0.60, 0.39 |
| 35 | (2-phenylpyridine) | (B-245) | 0.57, 0.42 |

-continued

| Ex. | Compound HL | Iridium complex | CIE x, y |
|---|---|---|---|
| 36 | (benzoxazole-phenol structure) | (B-256) | 0.60, 0.39 |
| 37 | (benzotriazole-naphthol structure) | (A-1) | 0.61, 0.38 |

-continued

| Ex. | Compound HL | Iridium complex | CIE x, y |
|---|---|---|---|
| 38 | (benzotriazole-phenol with tert-butyl, OH) | (B-257) | 0.61, 0.38 |
| 39 | (benzothiazole-phenol, OH) | (B-258) | 0.61, 0.38 |

-continued
| Ex. | Compound HL | Iridium complex | CIE x, y |
|---|---|---|---|
| 40 | 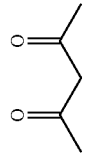 | 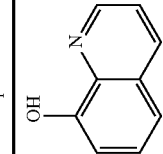 (B-145) | 0.62, 0.38 |
| 41 | 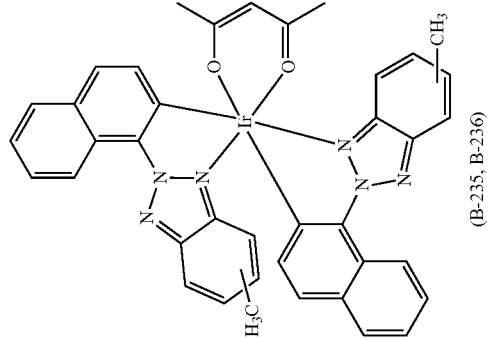 | 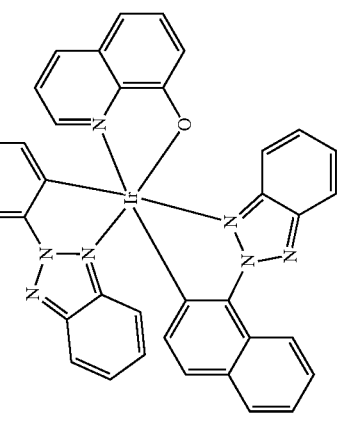 (B-235, B-236) | 0.62, 0.37 |

-continued

| Ex. | Compound HL | Iridium complex | CIE x, y |
|---|---|---|---|
| 42 | (2,2,6,6-tetramethylheptane-3,5-dione structure) | (B-237, B-238) | 0.62, 0.37 |
| 43 | (2-(benzoxazol-2-yl)phenol structure) | (B-259) | 0.61, 0.39 |

| Ex. | Compound HL | Iridium complex | CIE x, y |
|---|---|---|---|
| 44 | (structure of 2,2,6,6-tetramethylheptane-3,5-dione) | (B-239) | 0.63, 0.36 |
| 45 | (structure of 2-phenylpyridine) | (B-246) | 0.59, 0.40 |

-continued
| Ex. | Compound HL | Iridium complex | CIE x, y |
|---|---|---|---|
| 46 | 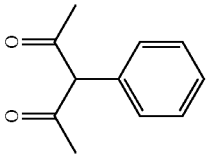 | 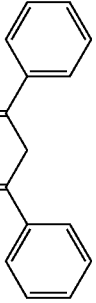 (B-260) | 0.63, 0.36 |
| 47 | 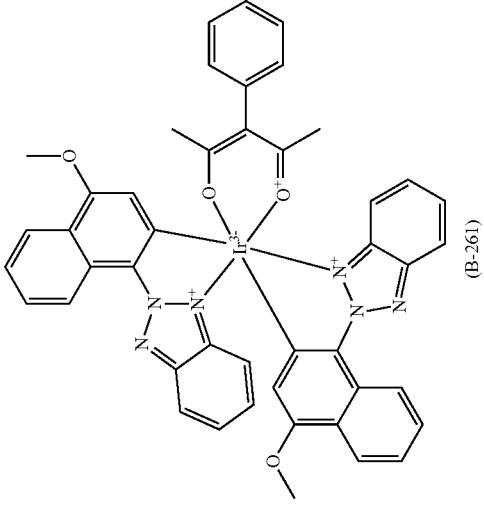 | 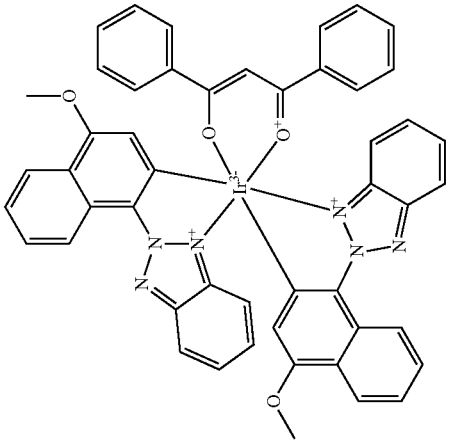 (B-261) | 0.64, 0.35 |

-continued

| Ex. | Compound HL | Iridium complex | CIE x, y |
|---|---|---|---|
| 48 | (quinoline-2-carboxylic acid structure) | (B-262) | 0.62, 0.37 |
| 49 | (isoquinoline-1-carboxylic acid structure) | (B-263) | 0.62, 0.37 |

| Ex. | Compound HL | Iridium complex | CIE x, y |
|---|---|---|---|
| 50 | (pyrazine-2-carboxylic acid structure) | (B-263) | 0.62, 0.36 |
| 51 | (2-(benzoxazol-2-yl)phenol structure) | (B-265) | 0.62, 0.37 |

-continued

| Ex. | Compound HL | Iridium complex | CIE x, y |
|---|---|---|---|
| 52 | (structure of 4-diethylamino-2-hydroxybenzaldehyde) | (B-266) | 0.63, 0.36 |
| 53 | (structure of 1-(1-methyl-1H-imidazol-2-yl)-4,4,4-trifluorobut-1-en-3-one) | (B-267) | 0.63, 0.37 |

| Ex. | Compound HL | Iridium complex | CIE x, y |
|---|---|---|---|
| 54 | 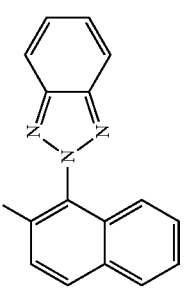 | 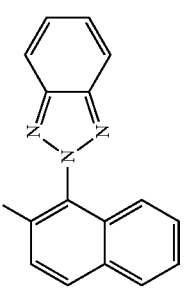 (A-2) | 0.62, 0.37 |
| 55 | 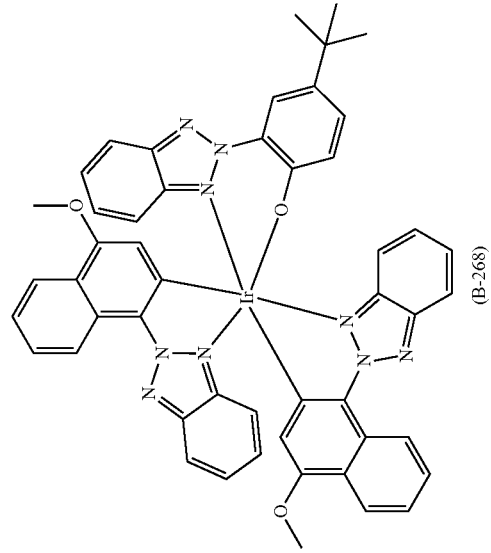 | 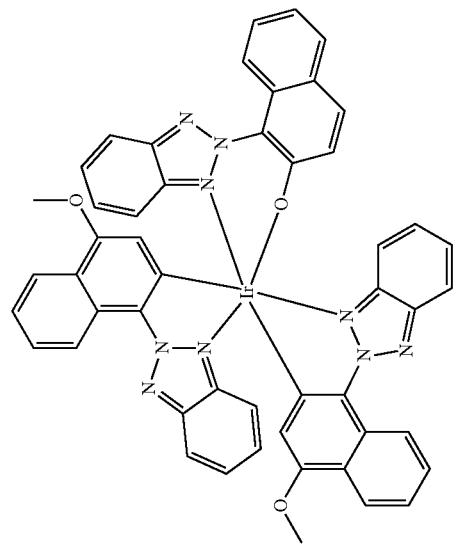 (B-268) | 0.62, 0.37 |

-continued
| Ex. | Compound HL | Iridium complex | CIE x, y |
|---|---|---|---|
| 56 | 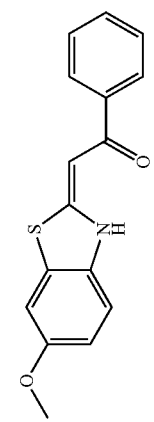 | 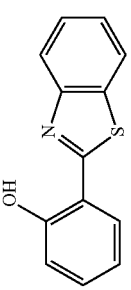 (B-269) | 0.62, 0.37 |
| 57 | 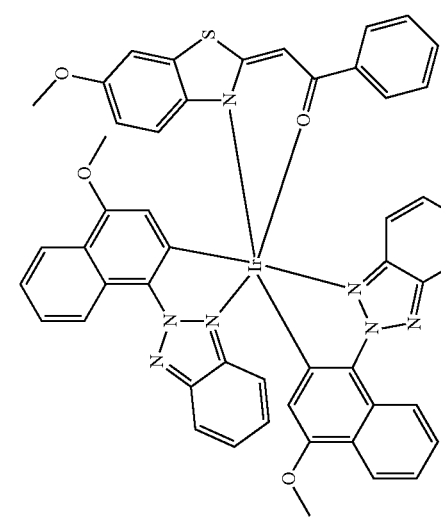 | 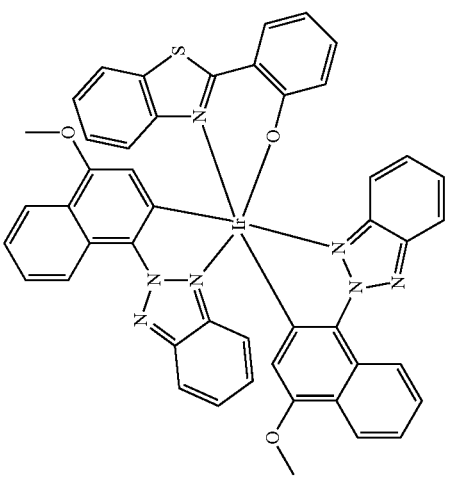 (B-270) | 0.62, 0.37 |

-continued

| Ex. | Compound HL | Iridium complex | CIE x, y |
|---|---|---|---|
| 58 | (benzotriazole-phenol with tert-octyl substituent) | (B-271) | 0.63, 0.37 |
| 59 | 8-hydroxyquinoline | (B-146) | 0.64, 0.36 |

| Ex. | Compound HL | Iridium complex | CIE x, y |
|---|---|---|---|
| 60 | 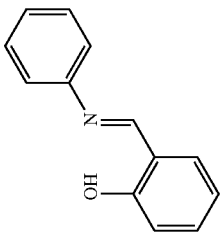 | 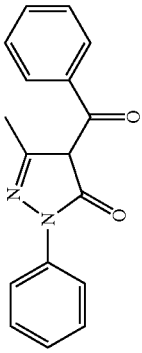 (B-272) | 0.64, 0.36 |
| 61 | 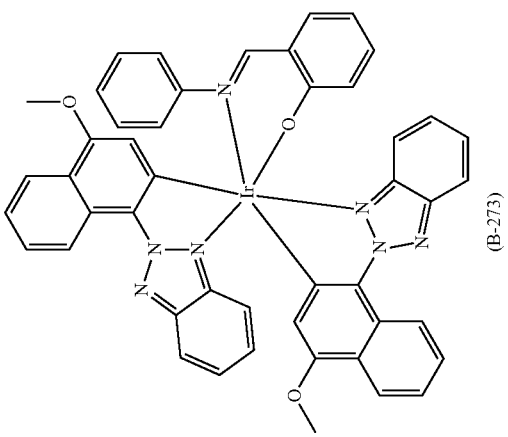 | 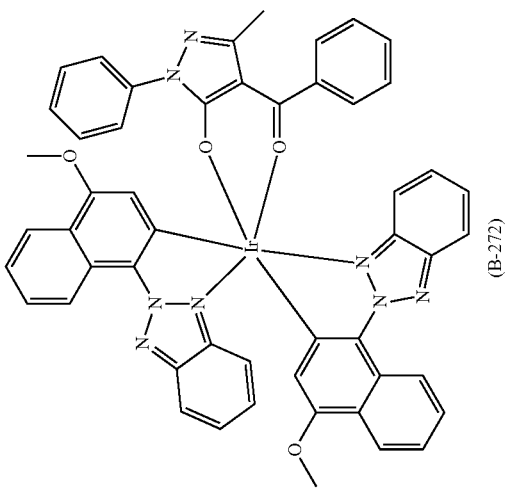 (B-273) | 0.63, 0.37 |

| Ex. | Compound HL | Iridium complex | CIE x, y |
|---|---|---|---|
| 62 | 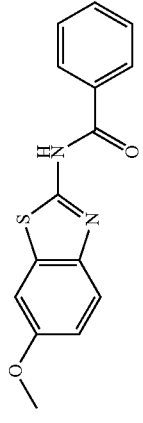 | 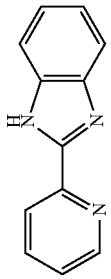 (B-274) | 0.60, 0.40 |
| 63 | 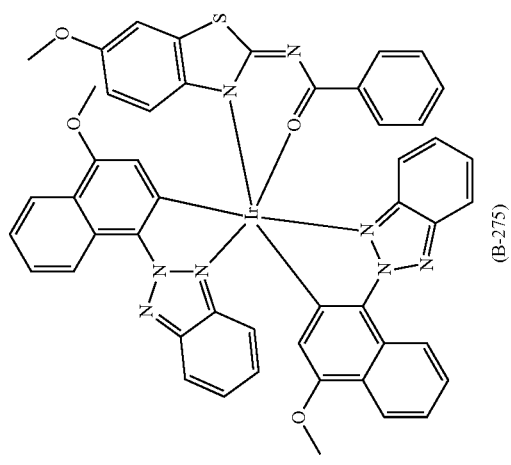 | 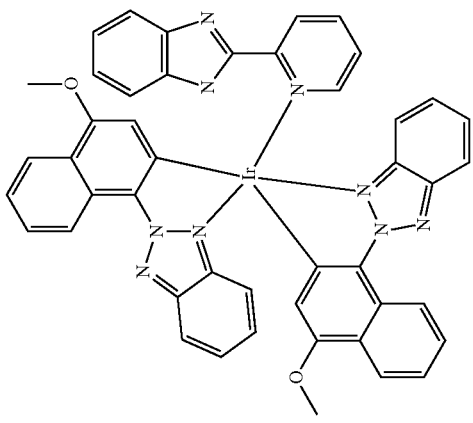 (B-275) | 0.62, 0.38 |

-continued

| Ex. | Compound HL | Iridium complex | CIE x, y |
|---|---|---|---|
| 64 | [structure of N-(thiazol-2-yl)-2,2,2-trifluoroacetamide] | [structure (B-275)] | 0.63, 0.37 |
| 65 | [structure of N-(benzo[d]thiazol-2-yl)benzamide] | [structure (B-277)] | 0.62, 0.38 |

| Ex. | Compound HL | Iridium complex | CIE x, y |
|---|---|---|---|
| 66 | 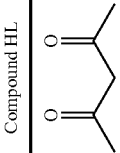 | 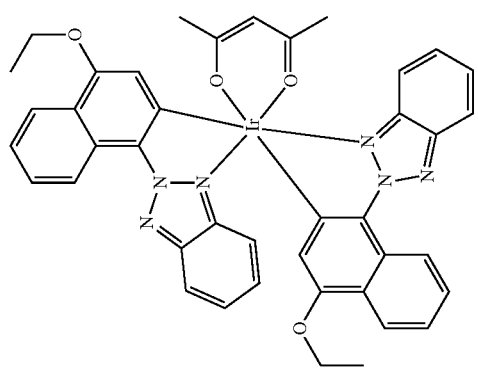 (B-3) | 0.64, 0.36 |
| 67 | 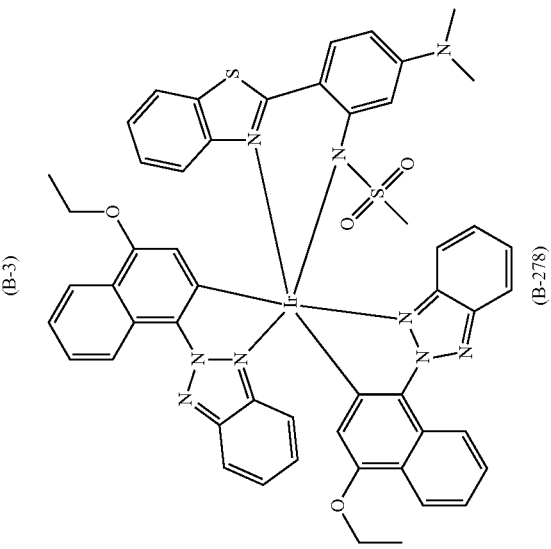 | 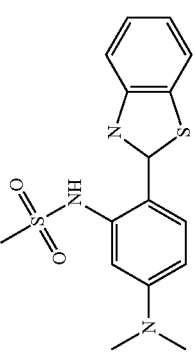 (B-278) | 0.62, 0.37 |

| Ex. | Compound HL | Iridium complex | CIE x, y |
|---|---|---|---|
| 68 | 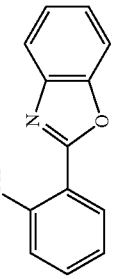 | 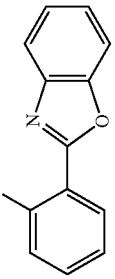 (B-279) | 0.62, 0.37 |
| 69 | 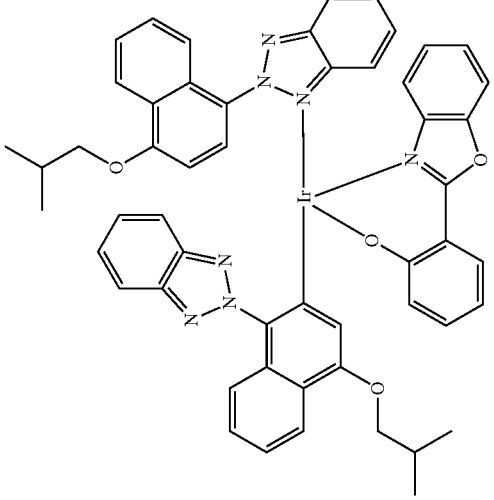 | 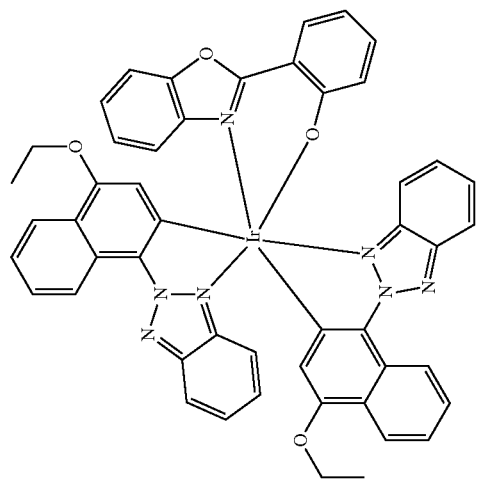 (B-280) | 0.63, 0.37 |

-continued

| Ex. | Compound HL | Iridium complex | CIE x, y |
|---|---|---|---|
| 70 | (2,4-pentanedione structure) | (B-240) | 0.65, 0.35 |
| 71 | (2,2,6,6-tetramethyl-3,5-heptanedione structure) | (B-241) | 0.65, 0.35 |

-continued

| Ex. | Compound HL | Iridium complex | CIE x, y |
|---|---|---|---|
| 72 | (structure shown) | (B-281) | 0.63, 0.37 |
| 73 | (structure shown) | (B-282) | 0.64, 0.36 |

| Ex. | Compound HL | Iridium complex | CIE x, y |
|---|---|---|---|
| 74 | 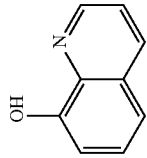 | 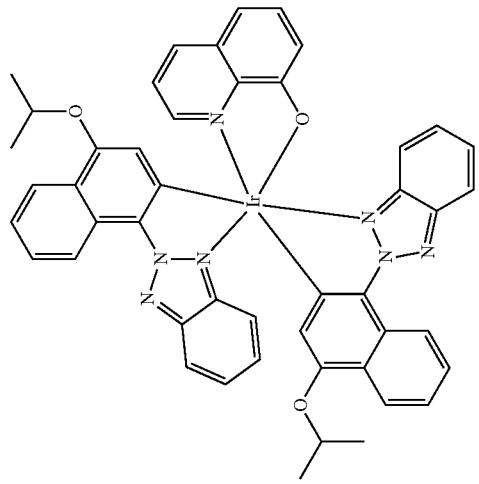 (B-242) | 0.64, 0.36 |
| 75 | 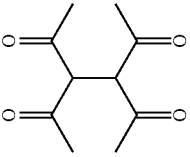 | 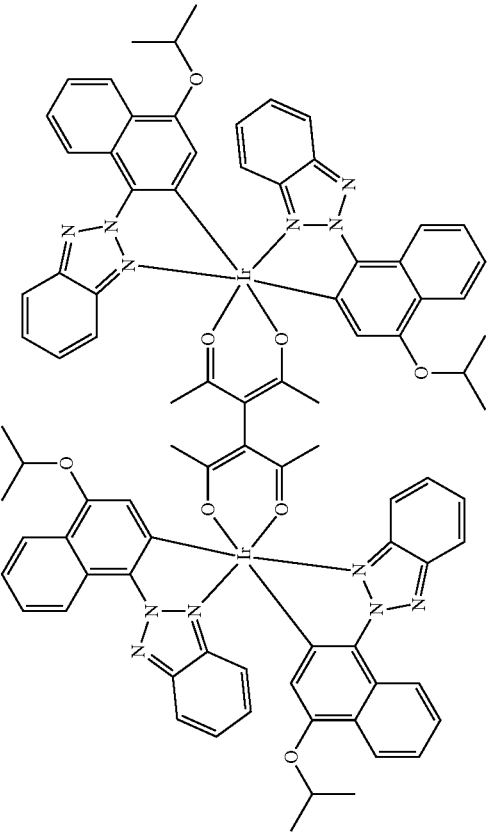 (B-283) | 0.65, 0.35 |

| Ex. | Compound HL | Iridium complex | CIE x, y |
|---|---|---|---|
| 76 | (3-phenylpentane-2,4-dione) | (B-284) | 0.65, 0.35 |
| 77 | (pentane-2,4-dione) | (B-8) | |

-continued
| Ex. | Compound HL | Iridium complex | CIE x, y |
|---|---|---|---|
| 78 | 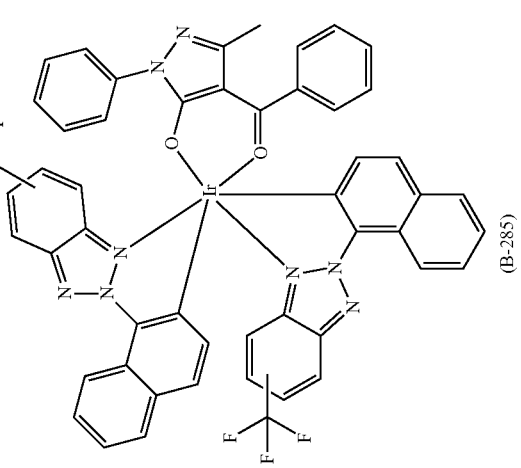 | 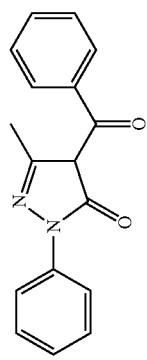 (B-285) | 0.66, 0.34 |

| Ex. | Compound HL | Iridium complex | CIE x, y |
|---|---|---|---|
| 79 | ![benzotriazole-phenol with tert-octyl] | (B-286) | 0.64, 0.36 |

-continued

| Ex. | Compound HL | Iridium complex | CIE x, y |
|---|---|---|---|
| 80 | (naphthol with 5-trifluoromethyl-benzotriazole substituent) | (B-287) | 0.64, 0.36 |

| Ex. | Compound HL | Iridium complex | CIE x, y |
|---|---|---|---|
| 81 | [structure of 2-(benzoxazol-2-yl)phenol] | [structure B-288] | 0.64, 0.36 |

| Ex. | Compound HL | Iridium complex | CIE x, y |
|---|---|---|---|
| 82 | (2-hydroxyphenyl benzothiazole structure) | (B-288) | 0.65, 0.35 |

| Ex. | Compound HL | Iridium complex | CIE x, y |
|---|---|---|---|
| 83 | 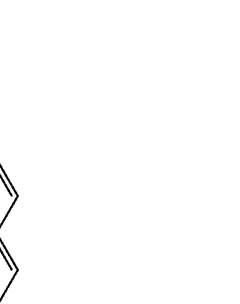 | 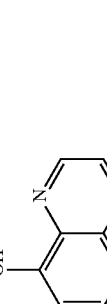 (B-154, B-155) | 0.64, 0.36 |

| Ex. | Compound HL | Iridium complex | CIE x, y |
|---|---|---|---|
| 84 | 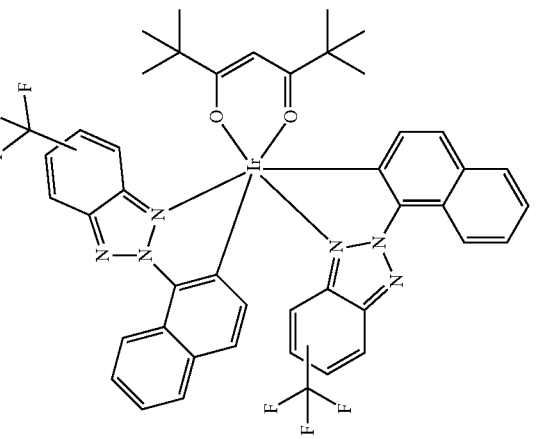 | 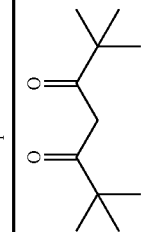 (B-154, B-155) | 0.66, 0.34 |

-continued

| Ex. | Compound HL | Iridium complex | CIE x, y |
|---|---|---|---|
| 85 | (diacetyl-bis-acetylacetone compound) | (B-290) | 0.66, 0.34 |

| Ex. | Compound HL | Iridium complex | CIE x, y |
|---|---|---|---|
| 86 | 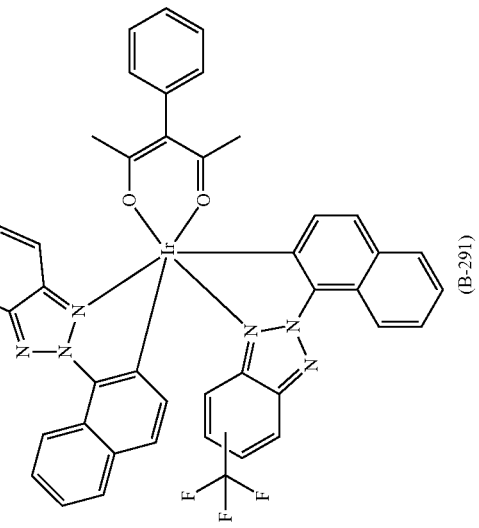 | 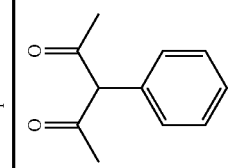 (B-291) | 0.66, 0.34 |

| Ex. | Compound HL | Iridium complex | CIE x, y |
|---|---|---|---|
| 87 | (2-phenylpyridine) | (B-243, B-244) | 0.62, 0.38 |

-continued

| Ex. | Compound HL | Iridium complex | CIE x, y |
|---|---|---|---|
| 88 | (imidazole-CH=C(O)CF₃ structure) | (B-292) | 0.64, 0.36 |
| 89 | ethyl acetoacetate | (B-293) | 0.66, 0.34 |

-continued

| Ex. | Compound HL | Iridium complex | CIE x, y |
|---|---|---|---|
| 90 | (2,4-pentanedione structure) | (B-12, B-13) | 0.68, 0.32 |
| 91 | (2-(2-hydroxyphenyl)benzoxazole structure) | (B-294) | 0.65, 0.34 |

| Ex. | Compound HL | Iridium complex | CIE x, y |
|---|---|---|---|
| 92 | (2,4-pentanedione) | (E-1) | 0.68, 0.32 |

| Ex. | Compound HL | Iridium complex | CIE x, y |
|---|---|---|---|
| 93 | (di-tert-butyl-substituted 1,3-diketone structure) | (E-2) iridium complex structure | 0.68, 0.32 |

-continued

| Ex. | Compound HL | Iridium complex | CIE x, y |
|---|---|---|---|
| 94 | (structure of 1-methyl-imidazole trifluoromethyl ketone ligand) | (E-3) | 0.66, 0.34 |

| Ex. | Compound HL | Iridium complex | CIE x, y |
|---|---|---|---|
| 95 | 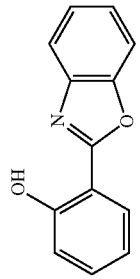 | 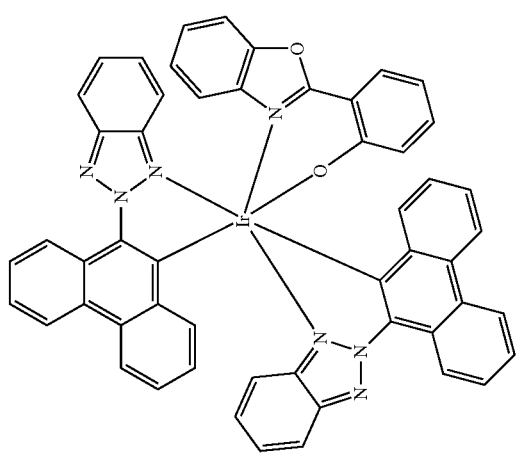 (E-4) | 0.67, 0.33 |
| 96 | 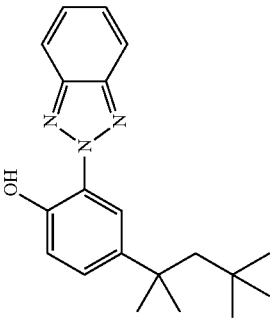 | 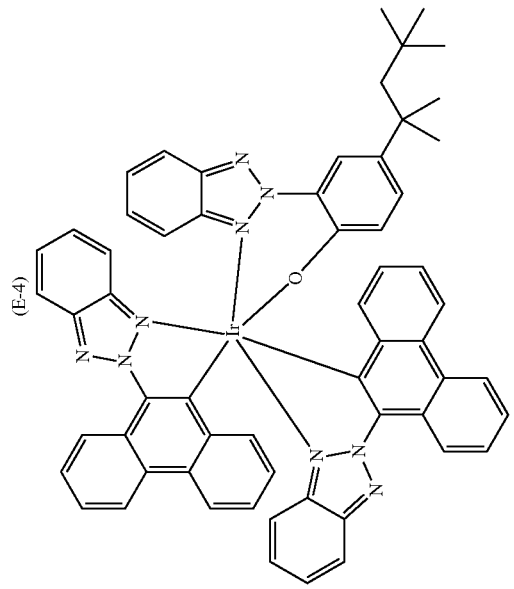 (E-5) | 0.67, 0.33 |

Application Example 1

Product of example 22 of the present invention:

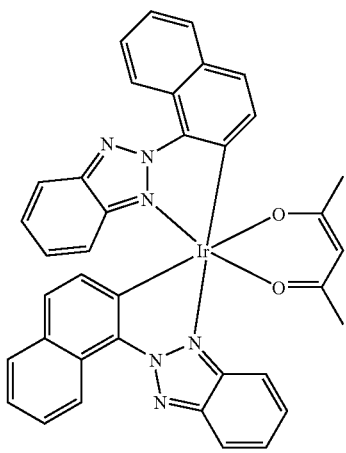
(B-1)

| PL (max.) | CIE (X, Y) | Color |
|---|---|---|
| 601 nm | 0.62, 0.37 | red |

Comparative Application Example 1

Iridium complex of Example 6 in WO2006/000544

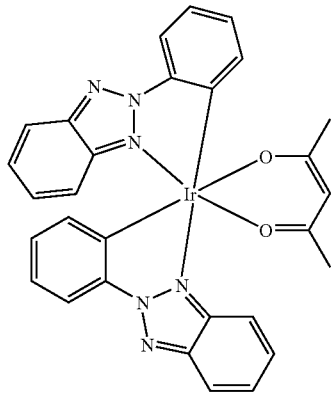

| PL (max.) | CIE (X, Y) | Color |
|---|---|---|
| 557 nm | 0.44, 0.51 | yellow |

As evident from Comparative Application Example 1 the product of Example 6 in WO2006/000544 does not show the desired red luminescence.

Application Example 2

Device fabrication: Prior to device fabrication, indium tin oxide (ITO) on glass is patterned as 2 mm wide stripes (sheet resistance 20 Ω/square). The substrates are cleaned by sonication in a alkaline solution (Deconex), rinsing with deionized water, exposed to acetone and isopropanol for 3-4 min in each solvent. After the cleaning procedure, the substrates are dried under a nitrogen flow followed by UV ozone treatment for 10 min.

Organic layers of the OLEDs are sequentially deposited by thermal evaporation from resistively heated tantalum boats at a base pressure of $2 \times 10^{-6}$ Torr, at 2 Å/s.

The rate of each single component source is controlled by a thickness monitor (Inficon) close to the substrate. All the devices are encapsulated with a glass lid sealed with an epoxy resin in a nitrogen glove box, immediately after fabrication.

The devices are characterized in air. Current-voltage measurements are made with a Keithley source meter (model 2400). Light intensity is measured using a Newport model 1835 optical power meter and a Newport detector. EL specta were measured with a Photon Technology International fluorimeter.

An OLED is prepared having the following structure from the anode to the cathode: 10 nm of copper phtalocyanine (CuPc), using 10 nm of an improved hole transport layer, such as NHT5:NDP2 of Novaled AG, 10 nm of 4,4' bis[N-81-naphthyl)-N-phenylamino]-biphenyl (α-NPD), 20 nm of aluminum(III) bis(2-methyl-8-quinolato) 4-phenyl-phenolate (BAlq) doped with 15 wt % of compound B-2 obtained in example 23, 10 nm of BAlq acting as hole blocking layer, 60 nm of an improved electron transport layer, such as NET-5:NDN-1 from Novaled, and 130 nm of aluminium as top electrode.

Comparative Application Example 2

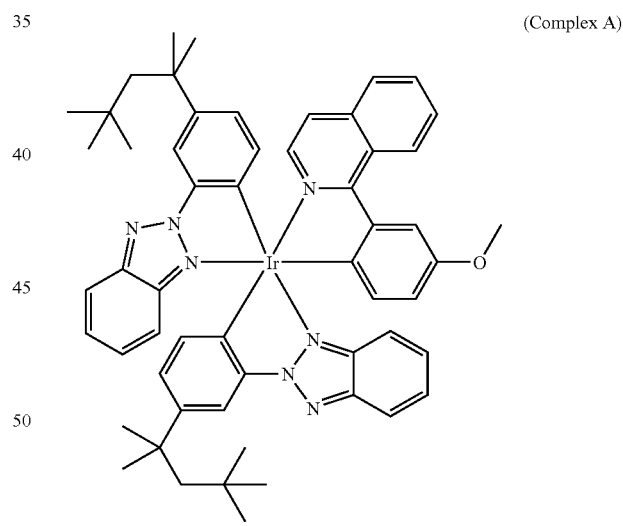
(Complex A)

The element is prepared and evaluated in the same manner as described in Application Example 2, except for using complex A instead of Cpd. B-2. The synthesis of complex A is described in Example 12 of WO2006/000544, with 2-nonanone as solvent instead of acetone, using 1-(3-methoxy-phenyl)-isoquinoline instead of phenylpyridine, and using a reaction temperature of 150-180° C. in the second reaction step.

The organic stack consists of ITO/10 nm of CuPc/10 nm of NHT5:NDP2/10 nm of α-NPD/20 nm of BAlq doped with 15 wt % complex A/10 nm BAlq/60 nm NET-5:NDN-1/130 nm Al.

The power efficiency of the device of Application Example 2 is more than doubled than that of the device of the Comparative Application Example (see the following table):

| EML | | Current eff. cd/A @ 1000 cd/m$^2$ | Power eff. lm/W @1000 cd/m$^2$ | Voltage V @ 1000 cd/m$^2$ | CIE X | CIE Y |
|---|---|---|---|---|---|---|
| Application Example 2 | BAlq: 15 wt % dopant[1] | 8.8 | 8.2 | 3.39 | 0.66 | 0.34 |
| Comparative Application Example 2 | BAlq: 15 wt % dopant[2] | 4.7 | 3.5 | 4.19 | 0.67 | 0.32 |

[1]Compound B-2.
[2]Complex A.

While WO2006/000544 also describes red emitting compounds (Complex A), those compounds are less efficient as corresponding compounds of the present invention (compound B-2).

The invention claimed is:
1. A compound of formulae shown below:

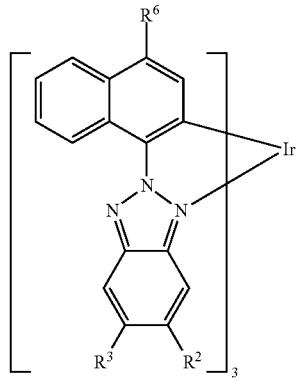

wherein

| Cpd. | R$^2$ | R$^3$ | R$^6$ |
|---|---|---|---|
| A-2 | H | H | OCH$_3$ |
| A-3 | H | H | OCH$_2$CH$_3$ |
| A-4 | H | H | O-n-butyl |
| A-5 | H | H | O-iso-butyl |
| A-6 | H | H | O-2-butyl |
| A-7 | H | H | O-2-ethylhexyl |
| A-8 | H | H | N(CH$_3$)$_2$ |
| A-9 | H | H | NPh$_2$ |
| A-10 | H | CF$_3$ | H |
| A-11 | CF$_3$ | H | H |
| A-12 | H | CF$_3$ | OCH$_3$ |
| A-13 | CF$_3$ | H | OCH$_3$ |
| A-14 | H | CF$_3$ | OCH$_2$CH$_3$ |
| A-15 | CF$_3$ | H | OCH$_2$CH$_3$ |
| A-16 | H | CF$_3$ | O-n-butyl |
| A-17 | CF$_3$ | H | O-n-butyl |
| A-18 | H | CF$_3$ | O-iso-butyl |
| A-19 | CF$_3$ | H | O-iso-butyl |
| A-20 | H | CF$_3$ | O-2-butyl |
| A-21 | CF$_3$ | H | O-2-butyl |
| A-22 | H | CF$_3$ | O-2-ethylhexyl |
| A-23 | CF$_3$ | H | O-2-ethylhexyl |
| A-24 | H | CF$_3$ | N(CH$_3$)$_2$ |
| A-25 | CF$_3$ | H | N(CH$_3$)$_2$ |
| A-26 | H | CF$_3$ | NPh$_2$ |
| A-27 | CF$_3$ | H | NPh$_2$ |
| A-28 | H | CN | H |
| A-29 | CN | H | H |
| A-30 | H | CN | OCH$_3$ |
| A-31 | CN | H | OCH$_2$CH$_3$ |
| A-32 | H | CN | OCH$_2$CH$_3$ |
| A-33 | CN | H | O-n-butyl |

-continued

| | | | |
|---|---|---|---|
| A-34 | H | CN | O-n-butyl |
| A-35 | CN | H | O-iso-butyl |
| A-36 | H | CN | O-iso-butyl |
| A-37 | CN | H | O-2-butyl |
| A-38 | H | CN | O-2-butyl |
| A-39 | CN | H | O-2-ethylhexyl |
| A-40 | H | CN | O-2-ethylhexyl |
| A-41 | CN | H | N(CH$_3$)$_2$ |
| A-42 | H | CN | N(CH$_3$)$_2$ |
| A-43 | CN | H | NPh$_2$ |
| A-44 | H | CN | NPh$_2$ |

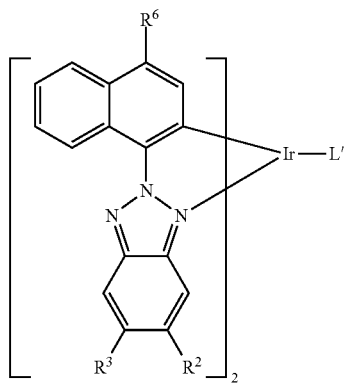

wherein

| Cpd. | L' | R$^2$ | R$^3$ | R$^6$ |
|---|---|---|---|---|
| B-1 | A$^{1)}$ | H | H | H |
| B-2 | A$^{1)}$ | H | H | OCH$_3$ |
| B-3 | A$^{1)}$ | H | H | OCH$_2$CH$_3$ |
| B-4 | A$^{1)}$ | H | H | O-n-butyl |
| B-5 | A$^{1)}$ | H | H | O-iso-butyl |
| B-6 | A$^{1)}$ | H | H | O-2-butyl |
| B-7 | A$^{1)}$ | H | H | O-2-ethylhexyl |
| B-8 | A$^{1)}$ | H | H | N(CH$_3$)$_2$ |
| B-9 | A$^{1)}$ | H | H | NPh$_2$ |
| B-10 | A$^{1)}$ | H | CF$_3$ | H |
| B-11 | A$^{1)}$ | CF$_3$ | H | H |
| B-12 | A$^{1)}$ | H | CF$_3$ | OCH$_3$ |
| B-13 | A$^{1)}$ | CF$_3$ | H | OCH$_3$ |
| B-14 | A$^{1)}$ | H | CF$_3$ | OCH$_2$CH$_3$ |
| B-15 | A$^{1)}$ | CF$_3$ | H | OCH$_2$CH$_3$ |
| B-16 | A$^{1)}$ | H | CF$_3$ | O-n-butyl |
| B-17 | A$^{1)}$ | CF$_3$ | H | O-n-butyl |
| B-18 | A$^{1)}$ | H | CF$_3$ | O-iso-butyl |
| B-19 | A$^{1)}$ | CF$_3$ | H | O-iso-butyl |
| B-20 | A$^{1)}$ | H | CF$_3$ | O-2-butyl |
| B-21 | A$^{1)}$ | CF$_3$ | H | O-2-butyl |
| B-22 | A$^{1)}$ | H | CF$_3$ | O-2-ethylhexyl |
| B-23 | A$^{1)}$ | CF$_3$ | H | O-2-ethylhexyl |
| B-24 | A$^{1)}$ | H | CF$_3$ | N(CH$_3$)$_2$ |
| B-25 | A$^{1)}$ | CF$_3$ | H | N(CH$_3$)$_2$ |
| B-26 | A$^{1)}$ | H | CF$_3$ | NPh$_2$ |
| B-27 | A$^{1)}$ | CF$_3$ | H | NPh$_2$ |
| B-28 | A$^{1)}$ | H | CN | H |
| B-29 | A$^{1)}$ | CN | H | H |
| B-30 | A$^{1)}$ | CN | H | OCH$_3$ |
| B-31 | A$^{1)}$ | H | CN | OCH$_3$ |
| B-32 | A$^{1)}$ | CN | H | OCH$_2$CH$_3$ |
| B-33 | A$^{1)}$ | H | CN | OCH$_2$CH$_3$ |
| B-34 | A$^{1)}$ | CN | H | O-n-butyl |
| B-35 | A$^{1)}$ | H | CN | O-n-butyl |
| B-36 | A$^{1)}$ | CN | H | O-iso-butyl |
| B-37 | A$^{1)}$ | H | CN | O-iso-butyl |
| B-38 | A$^{1)}$ | CN | H | O-2-butyl |
| B-39 | A$^{1)}$ | H | CN | O-2-butyl |
| B-40 | A$^{1)}$ | CN | H | O-2-ethylhexyl |
| B-41 | A$^{1)}$ | H | CN | O-2-ethylhexyl |
| B-42 | A$^{1)}$ | CN | H | N(CH$_3$)$_2$ |
| B-43 | A$^{1)}$ | H | CN | N(CH$_3$)$_2$ |
| B-44 | A$^{1)}$ | CN | H | NPh$_2$ |
| B-45 | A$^{1)}$ | H | CN | NPh$_2$ |
| B-46 | B$^{1)}$ | H | H | H |

-continued

| | | | | |
|---|---|---|---|---|
| B-47 | B[1)] | H | H | OCH$_3$ |
| B-48 | B[1)] | H | H | OCH$_2$CH$_3$ |
| B-49 | B[1)] | H | H | O-n-butyl |
| B-50 | B[1)] | H | H | O-iso-butyl |
| B-51 | B[1)] | H | H | O-2-butyl |
| B-52 | B[1)] | H | H | O-2-ethylhexyl |
| B-53 | B[1)] | H | H | N(CH$_3$)$_2$ |
| B-54 | B[1)] | H | H | NPh$_2$ |
| B-55 | B[1)] | H | CF$_3$ | H |
| B-56 | B[1)] | CF$_3$ | H | H |
| B-57 | B[1)] | H | CF$_3$ | OCH$_3$ |
| B-58 | B[1)] | CF$_3$ | H | OCH$_3$ |
| B-59 | B[1)] | H | CF$_3$ | OCH$_2$CH$_3$ |
| B-60 | B[1)] | CF$_3$ | H | OCH$_2$CH$_3$ |
| B-61 | B[1)] | H | CF$_3$ | O-n-butyl |
| B-62 | B[1)] | CF$_3$ | H | O-n-butyl |
| B-63 | B[1)] | H | CF$_3$ | O-iso-butyl |
| B-64 | B[1)] | CF$_3$ | H | O-iso-butyl |
| B-65 | B[1)] | H | CF$_3$ | O-2-butyl |
| B-66 | B[1)] | CF$_3$ | H | O-2-butyl |
| B-67 | B[1)] | H | CF$_3$ | O-2-ethylhexyl |
| B-68 | B[1)] | CF$_3$ | H | O-2-ethylhexyl |
| B-69 | B[1)] | H | CF$_3$ | N(CH$_3$)$_2$ |
| B-70 | B[1)] | CF$_3$ | H | N(CH$_3$)$_2$ |
| B-71 | B[1)] | H | CF$_3$ | NPh$_2$ |
| B-72 | B[1)] | CF$_3$ | H | NPh$_2$ |
| B-73 | B[1)] | H | CN | H |
| B-74 | B[1)] | CN | H | H |
| B-75 | B[1)] | CN | H | OCH$_3$ |
| B-76 | B[1)] | H | CN | OCH$_3$ |
| B-77 | B[1)] | CN | H | OCH$_2$CH$_3$ |
| B-78 | B[1)] | H | CN | OCH$_2$CH$_3$ |
| B-79 | B[1)] | CN | H | O-n-butyl |
| B-80 | B[1)] | H | CN | O-n-butyl |
| B-81 | B[1)] | CN | H | O-iso-butyl |
| B-82 | B[1)] | H | CN | O-iso-butyl |
| B-83 | B[1)] | CN | H | O-2-butyl |
| B-84 | B[1)] | H | CN | O-2-butyl |
| B-85 | B[1)] | CN | H | O-2-ethylhexyl |
| B-86 | B[1)] | H | CN | O-2-ethylhexyl |
| B-87 | B[1)] | CN | H | N(CH$_3$)$_2$ |
| B-88 | B[1)] | H | CN | N(CH$_3$)$_2$ |
| B-89 | B[1)] | CN | H | NPh$_2$ |
| B-99 | B[1)] | H | CN | NPh$_2$ |
| B-100 | C[1)] | H | H | H |
| B-101 | C[1)] | H | H | OCH$_3$ |
| B-102 | C[1)] | H | H | OCH$_2$CH$_3$ |
| B-103 | C[1)] | H | H | O-n-butyl |
| B-104 | C[1)] | H | H | O-iso-butyl |
| B-105 | C[1)] | H | H | O-2-butyl |
| B-106 | C[1)] | H | H | O-2-ethylhexyl |
| B-107 | C[1)] | H | H | N(CH$_3$)$_2$ |
| B-108 | C[1)] | H | H | NPh$_2$ |
| B-109 | C[1)] | H | CF$_3$ | H |
| B-110 | C[1)] | CF$_3$ | H | H |
| B-111 | C[1)] | H | CF$_3$ | OCH$_3$ |
| B-112 | C[1)] | CF$_3$ | H | OCH$_3$ |
| B-113 | C[1)] | H | CF$_3$ | OCH$_2$CH$_3$ |
| B-114 | C[1)] | CF$_3$ | H | OCH$_2$CH$_3$ |
| B-115 | C[1)] | H | CF$_3$ | O-n-butyl |
| B-116 | C[1)] | CF$_3$ | H | O-n-butyl |
| B-117 | C[1)] | H | CF$_3$ | O-iso-butyl |
| B-118 | C[1)] | CF$_3$ | H | O-iso-butyl |
| B-119 | C[1)] | H | CF$_3$ | O-2-butyl |
| B-120 | C[1)] | CF$_3$ | H | O-2-butyl |
| B-121 | C[1)] | H | CF$_3$ | O-2-ethylhexyl |
| B-122 | C[1)] | CF$_3$ | H | O-2-ethylhexyl |
| B-123 | C[1)] | H | CF$_3$ | N(CH$_3$)$_2$ |
| B-124 | C[1)] | CF$_3$ | H | N(CH$_3$)$_2$ |
| B-125 | C[1)] | H | CF$_3$ | NPh$_2$ |
| B-126 | C[1)] | CF$_3$ | H | NPh$_2$ |
| B-127 | C[1)] | H | CN | H |
| B-128 | C[1)] | CN | H | H |
| B-129 | C[1)] | CN | H | OCH$_3$ |
| B-130 | C[1)] | H | CN | OCH$_3$ |
| B-131 | C[1)] | CN | H | OCH$_2$CH$_3$ |
| B-132 | C[1)] | H | CN | OCH$_2$CH$_3$ |
| B-133 | C[1)] | CN | H | O-n-butyl |
| B-134 | C[1)] | H | CN | O-n-butyl |

-continued

| | | | | |
|---|---|---|---|---|
| B-135 | C[1] | CN | H | O-iso-butyl |
| B-136 | C[1] | H | CN | O-iso-butyl |
| B-137 | C[1] | CN | H | O-2-butyl |
| B-138 | C[1] | H | CN | O-2-butyl |
| B-139 | C[1] | CN | H | O-2-ethylhexyl |
| B-140 | C[1] | H | CN | O-2-ethylhexyl |
| B-141 | C[1] | CN | H | $N(CH_3)_2$ |
| B-142 | C[1] | H | CN | $N(CH_3)_2$ |
| B-143 | C[1] | H | CN | $NPh_2$ |
| B-144 | C[1] | CN | H | $NPh_2$ |
| B-145 | D[1] | H | H | H |
| B-146 | D[1] | H | H | $OCH_3$ |
| B-147 | D[1] | H | H | $OCH_2CH_3$ |
| B-148 | D[1] | H | H | O-n-butyl |
| B-149 | D[1] | H | H | O-iso-butyl |
| B-150 | D[1] | H | H | O-2-butyl |
| B-151 | D[1] | H | H | O-2-ethylhexyl |
| B-152 | D[1] | H | H | $N(CH_3)_2$ |
| B-153 | D[1] | H | H | $NPh_2$ |
| B-154 | D[1] | H | $CF_3$ | H |
| B-155 | D[1] | $CF_3$ | H | H |
| B-156 | D[1] | H | $CF_3$ | $OCH_3$ |
| B-157 | D[1] | $CF_3$ | H | $OCH_3$ |
| B-158 | D[1] | H | $CF_3$ | $OCH_2CH_3$ |
| B-159 | D[1] | $CF_3$ | H | $OCH_2CH_3$ |
| B-160 | D[1] | H | $CF_3$ | O-n-butyl |
| B-161 | D[1] | $CF_3$ | H | O-n-butyl |
| B-162 | D[1] | H | $CF_3$ | O-iso-butyl |
| B-163 | D[1] | $CF_3$ | H | O-iso-butyl |
| B-164 | D[1] | H | $CF_3$ | O-2-butyl |
| B-165 | D[1] | $CF_3$ | H | O-2-butyl |
| B-166 | D[1] | H | $CF_3$ | O-2-ethylhexyl |
| B-167 | D[1] | $CF_3$ | H | O-2-ethylhexyl |
| B-168 | D[1] | H | $CF_3$ | $N(CH_3)_2$ |
| B-169 | D[1] | $CF_3$ | H | $N(CH_3)_2$ |
| B-170 | D[1] | H | $CF_3$ | $NPh_2$ |
| B-171 | D[1] | $CF_3$ | H | $NPh_2$ |
| B-172 | D[1] | H | CN | H |
| B-173 | D[1] | CN | H | H |
| B-174 | D[1] | CN | H | $OCH_3$ |
| B-175 | D[1] | H | CN | $OCH_3$ |
| B-176 | D[1] | CN | H | $OCH_2CH_3$ |
| B-177 | D[1] | H | CN | $OCH_2CH_3$ |
| B-178 | D[1] | CN | H | O-n-butyl |
| B-179 | D[1] | H | CN | O-n-butyl |
| B-180 | D[1] | CN | H | O-iso-butyl |
| B-181 | D[1] | H | CN | O-iso-butyl |
| B-182 | D[1] | CN | H | O-2-butyl |
| B-183 | D[1] | H | CN | O-2-butyl |
| B-184 | D[1] | CN | H | O-2-ethylhexyl |
| B-185 | D[1] | H | CN | O-2-ethylhexyl |
| B-186 | D[1] | CN | H | $N(CH_3)_2$ |
| B-187 | D[1] | H | CN | $N(CH_3)_2$ |
| B-188 | D[1] | CN | H | $NPh_2$ |
| B-189 | D[1] | H | CN | $NPh_2$ |
| B-190 | E[1] | H | H | H |
| B-191 | E[1] | H | H | $OCH_3$ |
| B-192 | E[1] | H | H | $OCH_2CH_3$ |
| B-193 | E[1] | H | H | O-n-butyl |
| B-194 | E[1] | H | H | O-iso-butyl |
| B-195 | E[1] | H | H | O-2-butyl |
| B-196 | E[1] | H | H | O-2-ethylhexyl |
| B-197 | E[1] | H | H | $N(CH_3)_2$ |
| B-198 | E[1] | H | H | $NPh_2$ |
| B-199 | E[1] | H | $CF_3$ | H |
| B-200 | E[1] | $CF_3$ | H | H |
| B-201 | E[1] | H | $CF_3$ | $OCH_3$ |
| B-202 | E[1] | $CF_3$ | H | $OCH_3$ |
| B-203 | E[1] | H | $CF_3$ | $OCH_2CH_3$ |
| B-204 | E[1] | $CF_3$ | H | $OCH_2CH_3$ |
| B-205 | E[1] | H | $CF_3$ | O-n-butyl |
| B-206 | E[1] | $CF_3$ | H | O-n-butyl |
| B-207 | E[1] | H | $CF_3$ | O-iso-butyl |
| B-208 | E[1] | $CF_3$ | H | O-iso-butyl |
| B-209 | E[1] | H | $CF_3$ | O-2-butyl |
| B-210 | E[1] | $CF_3$ | H | O-2-butyl |
| B-211 | E[1] | H | $CF_3$ | O-2-ethylhexyl |
| B-212 | E[1] | $CF_3$ | H | O-2-ethylhexyl |
| B-213 | E[1] | H | $CF_3$ | $N(CH_3)_2$ |

-continued

| Cpd. | | | | |
|---|---|---|---|---|
| B-214 | E[1)] | CF$_3$ | H | N(CH$_3$)$_2$ |
| B-215 | E[1)] | H | CF$_3$ | NPh$_2$ |
| B-216 | E[1)] | CF$_3$ | H | NPh$_2$ |
| B-217 | E[1)] | H | CN | H |
| B-218 | E[1)] | CN | H | H |
| B-219 | E[1)] | CN | H | OCH$_3$ |
| B-220 | E[1)] | H | CN | OCH$_3$ |
| B-221 | E[1)] | CN | H | OCH$_2$CH$_3$ |
| B-222 | E[1)] | H | CN | OCH$_2$CH$_3$ |
| B-223 | E[1)] | CN | H | O-n-butyl |
| B-224 | E[1)] | H | CN | O-n-butyl |
| B-225 | E[1)] | CN | H | O-iso-butyl |
| B-226 | E[1)] | H | CN | O-iso-butyl |
| B-227 | E[1)] | CN | H | O-2-butyl |
| B-228 | E[1)] | H | CN | O-2-butyl |
| B-229 | E[1)] | CN | H | O-2-ethylhexyl |
| B-230 | E[1)] | H | CN | O-2-ethylhexyl |
| B-231 | E[1)] | CN | H | N(CH$_3$)$_2$ |
| B-232 | E[1)] | H | CN | N(CH$_3$)$_2$ |
| B-233 | E[1)] | CN | H | NPh$_2$ |
| B-234 | E[1)] | H | CN | NPh$_2$ |

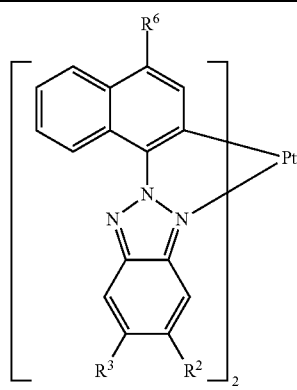

wherein

| Cpd. | R$^2$ | R$^3$ | R$^6$ |
|---|---|---|---|
| C-1 | H | H | H |
| C-2 | H | H | OCH$_3$ |
| C-3 | H | H | OCH$_2$CH$_3$ |
| C-4 | H | H | O-n-butyl |
| C-5 | H | H | O-iso-butyl |
| C-6 | H | H | O-2-butyl |
| C-7 | H | H | O-2-ethylhexyl |
| C-8 | H | H | N(CH$_3$)$_2$ |
| C-9 | H | H | NPh$_2$ |
| C-10 | H | CF$_3$ | H |
| C-11 | CF$_3$ | H | H |
| C-12 | H | CF$_3$ | OCH$_3$ |
| C-13 | CF$_3$ | H | OCH$_3$ |
| C-14 | H | CF$_3$ | OCH$_2$CH$_3$ |
| C-15 | CF$_3$ | H | OCH$_2$CH$_3$ |
| C-16 | H | CF$_3$ | O-n-butyl |
| C-17 | CF$_3$ | H | O-n-butyl |
| C-18 | H | CF$_3$ | O-iso-butyl |
| C-19 | CF$_3$ | H | O-iso-butyl |
| C-20 | H | CF$_3$ | O-2-butyl |
| C-21 | CF$_3$ | H | O-2-butyl |
| C-22 | H | CF$_3$ | O-2-ethylhexyl |
| C-23 | CF$_3$ | H | O-2-ethylhexyl |
| C-24 | H | CF$_3$ | N(CH$_3$)$_2$ |
| C-25 | CF$_3$ | H | N(CH$_3$)$_2$ |
| C-26 | H | CF$_3$ | NPh$_2$ |
| C-27 | CF$_3$ | H | NPh$_2$ |
| C-28 | H | CN | H |
| C-29 | CN | H | H |
| C-30 | H | CN | OCH$_3$ |
| C-31 | CN | H | OCH$_2$CH$_3$ |
| C-32 | H | CN | OCH$_2$CH$_3$ |
| C-33 | CN | H | O-n-butyl |
| C-34 | H | CN | O-n-butyl |
| C-35 | CN | H | O-iso-butyl |
| C-36 | H | CN | O-iso-butyl |

-continued

| Cpd. | | | |
|---|---|---|---|
| C-37 | CN | H | O-2-butyl |
| C-38 | H | CN | O-2-butyl |
| C-39 | CN | H | O-2-ethylhexyl |
| C-40 | H | CN | O-2-ethylhexyl |
| C-41 | CN | H | $N(CH_3)_2$ |
| C-42 | H | CN | $N(CH_3)_2$ |
| C-43 | CN | H | $NPh_2$ |
| C-44 | H | CN | $NPh_2$ |

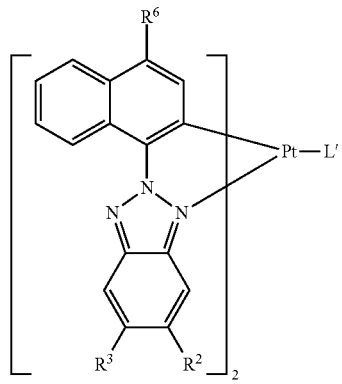

wherein

| Cpd. | L' | $R^2$ | $R^3$ | $R^6$ |
|---|---|---|---|---|
| D-1 | $A^{1)}$ | H | H | H |
| D-2 | $A^{1)}$ | H | H | $OCH_3$ |
| D-3 | $A^{1)}$ | H | H | $OCH_2CH_3$ |
| D-4 | $A^{1)}$ | H | H | O-n-butyl |
| D-5 | $A^{1)}$ | H | H | O-iso-butyl |
| D-6 | $A^{1)}$ | H | H | O-2-butyl |
| D-7 | $A^{1)}$ | H | H | O-2-ethylhexyl |
| D-8 | $A^{1)}$ | H | H | $N(CH_3)_2$ |
| D-9 | $A^{1)}$ | H | H | $NPh_2$ |
| D-10 | $A^{1)}$ | H | $CF_3$ | H |
| D-11 | $A^{1)}$ | $CF_3$ | H | H |
| D-12 | $A^{1)}$ | H | $CF_3$ | $OCH_3$ |
| D-13 | $A^{1)}$ | $CF_3$ | H | $OCH_3$ |
| D-14 | $A^{1)}$ | H | $CF_3$ | $OCH_2CH_3$ |
| D-15 | $A^{1)}$ | $CF_3$ | H | $OCH_2CH_3$ |
| D-16 | $A^{1)}$ | H | $CF_3$ | O-n-butyl |
| D-17 | $A^{1)}$ | $CF_3$ | H | O-n-butyl |
| D-18 | $A^{1)}$ | H | $CF_3$ | O-iso-butyl |
| D-19 | $A^{1)}$ | $CF_3$ | H | O-iso-butyl |
| D-20 | $A^{1)}$ | H | $CF_3$ | O-2-butyl |
| D-21 | $A^{1)}$ | $CF_3$ | H | O-2-butyl |
| D-22 | $A^{1)}$ | H | $CF_3$ | O-2-ethylhexyl |
| D-23 | $A^{1)}$ | $CF_3$ | H | O-2-ethylhexyl |
| D-24 | $A^{1)}$ | H | $CF_3$ | $N(CH_3)_2$ |
| D-25 | $A^{1)}$ | $CF_3$ | H | $N(CH_3)_2$ |
| D-26 | $A^{1)}$ | H | $CF_3$ | $NPh_2$ |
| D-27 | $A^{1)}$ | $CF_3$ | H | $NPh_2$ |
| D-28 | $A^{1)}$ | H | CN | H |
| D-29 | $A^{1)}$ | CN | H | H |
| D-30 | $A^{1)}$ | CN | H | $OCH_3$ |
| D-31 | $A^{1)}$ | H | CN | $OCH_3$ |
| D-32 | $A^{1)}$ | CN | H | $OCH_2CH_3$ |
| D-33 | $A^{1)}$ | H | CN | $OCH_2CH_3$ |
| D-34 | $A^{1)}$ | CN | H | O-n-butyl |
| D-35 | $A^{1)}$ | H | CN | O-n-butyl |
| D-36 | $A^{1)}$ | CN | H | O-iso-butyl |
| D-37 | $A^{1)}$ | H | CN | O-iso-butyl |
| D-38 | $A^{1)}$ | CN | H | O-2-butyl |
| D-39 | $A^{1)}$ | H | CN | O-2-butyl |
| D-40 | $A^{1)}$ | CN | H | O-2-ethylhexyl |
| D-41 | $A^{1)}$ | H | CN | O-2-ethylhexyl |
| D-42 | $A^{1)}$ | CN | H | $N(CH_3)_2$ |
| D-43 | $A^{1)}$ | H | CN | $N(CH_3)_2$ |
| D-44 | $A^{1)}$ | CN | H | $NPh_2$ |
| D-45 | $A^{1)}$ | H | CN | $NPh_2$ |
| D-46 | $B^{1)}$ | H | H | H |
| D-47 | $B^{1)}$ | H | H | $OCH_3$ |
| D-48 | $B^{1)}$ | H | H | $OCH_2CH_3$ |
| D-49 | $B^{1)}$ | H | H | O-n-butyl |

| | | | | |
|---|---|---|---|---|
| D-50 | B[1)] | H | H | O-iso-butyl |
| D-51 | B[1)] | H | H | O-2-butyl |
| D-52 | B[1)] | H | H | O-2-ethylhexyl |
| D-53 | B[1)] | H | H | N(CH$_3$)$_2$ |
| D-54 | B[1)] | H | H | NPh$_2$ |
| D-55 | B[1)] | H | CF$_3$ | H |
| D-56 | B[1)] | CF$_3$ | H | H |
| D-57 | B[1)] | H | CF$_3$ | OCH$_3$ |
| D-58 | B[1)] | CF$_3$ | H | OCH$_3$ |
| D-59 | B[1)] | H | CF$_3$ | OCH$_2$CH$_3$ |
| D-60 | B[1)] | CF$_3$ | H | OCH$_2$CH$_3$ |
| D-61 | B[1)] | H | CF$_3$ | O-n-butyl |
| D-62 | B[1)] | CF$_3$ | H | O-n-butyl |
| D-63 | B[1)] | H | CF$_3$ | O-iso-butyl |
| D-64 | B[1)] | CF$_3$ | H | O-iso-butyl |
| D-65 | B[1)] | H | CF$_3$ | O-2-butyl |
| D-66 | B[1)] | CF$_3$ | H | O-2-butyl |
| D-67 | B[1)] | H | CF$_3$ | O-2-ethylhexyl |
| D-68 | B[1)] | CF$_3$ | H | O-2-ethylhexyl |
| D-69 | B[1)] | H | CF$_3$ | N(CH$_3$)$_2$ |
| D-70 | B[1)] | CF$_3$ | H | N(CH$_3$)$_2$ |
| D-71 | B[1)] | H | CF$_3$ | NPh$_2$ |
| D-72 | B[1)] | CF$_3$ | H | NPh$_2$ |
| D-73 | B[1)] | H | CN | H |
| D-74 | B[1)] | CN | H | H |
| D-75 | B[1)] | CN | H | OCH$_3$ |
| D-76 | B[1)] | H | CN | OCH$_3$ |
| D-77 | B[1)] | CN | H | OCH$_2$CH$_3$ |
| D-78 | B[1)] | H | CN | OCH$_2$CH$_3$ |
| D-79 | B[1)] | CN | H | O-n-butyl |
| D-80 | B[1)] | H | CN | O-n-butyl |
| D-81 | B[1)] | CN | H | O-iso-butyl |
| D-82 | B[1)] | H | CN | O-iso-butyl |
| D-83 | B[1)] | CN | H | O-2-butyl |
| D-84 | B[1)] | H | CN | O-2-butyl |
| D-85 | B[1)] | CN | H | O-2-ethylhexyl |
| D-86 | B[1)] | H | CN | O-2-ethylhexyl |
| D-87 | B[1)] | CN | H | N(CH$_3$)$_2$ |
| D-88 | B[1)] | H | CN | N(CH$_3$)$_2$ |
| D-89 | B[1)] | CN | H | NPh$_2$ |
| D-99 | B[1)] | H | CN | NPh$_2$ |
| D-100 | C[1)] | H | H | H |
| D-101 | C[1)] | H | H | OCH$_3$ |
| D-102 | C[1)] | H | H | OCH$_2$CH$_3$ |
| D-103 | C[1)] | H | H | O-n-butyl |
| D-104 | C[1)] | H | H | O-iso-butyl |
| D-105 | C[1)] | H | H | O-2-butyl |
| D-106 | C[1)] | H | H | O-2-ethylhexyl |
| D-107 | C[1)] | H | H | N(CH$_3$)$_2$ |
| D-108 | C[1)] | H | H | NPh$_2$ |
| D-109 | C[1)] | H | CF$_3$ | H |
| D-110 | C[1)] | CF$_3$ | H | H |
| D-111 | C[1)] | H | CF$_3$ | OCH$_3$ |
| D-112 | C[1)] | CF$_3$ | H | OCH$_3$ |
| D-113 | C[1)] | H | CF$_3$ | OCH$_2$CH$_3$ |
| D-114 | C[1)] | CF$_3$ | H | OCH$_2$CH$_3$ |
| D-115 | C[1)] | H | CF$_3$ | O-n-butyl |
| D-116 | C[1)] | CF$_3$ | H | O-n-butyl |
| D-117 | C[1)] | H | CF$_3$ | O-iso-butyl |
| D-118 | C[1)] | CF$_3$ | H | O-iso-butyl |
| D-119 | C[1)] | H | CF$_3$ | O-2-butyl |
| D-120 | C[1)] | CF$_3$ | H | O-2-butyl |
| D-121 | C[1)] | H | CF$_3$ | O-2-ethylhexyl |
| D-122 | C[1)] | CF$_3$ | H | O-2-ethylhexyl |
| D-123 | C[1)] | H | CF$_3$ | N(CH$_3$)$_2$ |
| D-124 | C[1)] | CF$_3$ | H | N(CH$_3$)$_2$ |
| D-125 | C[1)] | H | CF$_3$ | NPh$_2$ |
| D-126 | C[1)] | CF$_3$ | H | NPh$_2$ |
| D-127 | C[1)] | H | CN | H |
| D-128 | C[1)] | CN | H | H |
| D-129 | C[1)] | CN | H | OCH$_3$ |
| D-130 | C[1)] | H | CN | OCH$_3$ |
| D-131 | C[1)] | CN | H | OCH$_2$CH$_3$ |
| D-132 | C[1)] | H | CN | OCH$_2$CH$_3$ |
| D-133 | C[1)] | CN | H | O-n-butyl |
| D-134 | C[1)] | H | CN | O-n-butyl |
| D-135 | C[1)] | CN | H | O-iso-butyl |
| D-136 | C[1)] | H | CN | O-iso-butyl |
| D-137 | C[1)] | CN | H | O-2-butyl |

-continued

| | | | | |
|---|---|---|---|---|
| D-138 | C[1) | H | CN | O-2-butyl |
| D-139 | C[1) | CN | H | O-2-ethylhexyl |
| D-140 | C[1) | H | CN | O-2-ethylhexyl |
| D-141 | C[1) | CN | H | $N(CH_3)_2$ |
| D-142 | C[1) | H | CN | $N(CH_3)_2$ |
| D-143 | C[1) | H | CN | $NPh_2$ |
| D-144 | C[1) | CN | H | $NPh_2$ |
| D-145 | D[1) | H | H | H |
| D-146 | D[1) | H | H | $OCH_3$ |
| D-147 | D[1) | H | H | $OCH_2CH_3$ |
| D-148 | D[1) | H | H | O-n-butyl |
| D-149 | D[1) | H | H | O-iso-butyl |
| D-150 | D[1) | H | H | O-2-butyl |
| D-151 | D[1) | H | H | O-2-ethylhexyl |
| D-152 | D[1) | H | H | $N(CH_3)_2$ |
| D-153 | D[1) | H | H | $NPh_2$ |
| D-154 | D[1) | H | $CF_3$ | H |
| D-155 | D[1) | $CF_3$ | H | H |
| D-156 | D[1) | H | $CF_3$ | $OCH_3$ |
| D-157 | D[1) | $CF_3$ | H | $OCH_3$ |
| D-158 | D[1) | H | $CF_3$ | $OCH_2CH_3$ |
| D-159 | D[1) | $CF_3$ | H | $OCH_2CH_3$ |
| D-160 | D[1) | H | $CF_3$ | O-n-butyl |
| D-161 | D[1) | $CF_3$ | H | O-n-butyl |
| D-162 | D[1) | H | $CF_3$ | O-iso-butyl |
| D-163 | D[1) | $CF_3$ | H | O-iso-butyl |
| D-164 | D[1) | H | $CF_3$ | O-2-butyl |
| D-165 | D[1) | $CF_3$ | H | O-2-butyl |
| D-166 | D[1) | H | $CF_3$ | O-2-ethylhexyl |
| D-167 | D[1) | $CF_3$ | H | O-2-ethylhexyl |
| D-168 | D[1) | H | $CF_3$ | $N(CH_3)_2$ |
| D-169 | D[1) | $CF_3$ | H | $N(CH_3)_2$ |
| D-170 | D[1) | H | $CF_3$ | $NPh_2$ |
| D-171 | D[1) | $CF_3$ | H | $NPh_2$ |
| D-172 | D[1) | H | CN | H |
| D-173 | D[1) | CN | H | H |
| D-174 | D[1) | CN | H | $OCH_3$ |
| D-175 | D[1) | H | CN | $OCH_3$ |
| D-176 | D[1) | CN | H | $OCH_2CH_3$ |
| D-177 | D[1) | H | CN | $OCH_2CH_3$ |
| D-178 | D[1) | CN | H | O-n-butyl |
| D-179 | D[1) | H | CN | O-n-butyl |
| D-180 | D[1) | CN | H | O-iso-butyl |
| D-181 | D[1) | H | CN | O-iso-butyl |
| D-182 | D[1) | CN | H | O-2-butyl |
| D-183 | D[1) | H | CN | O-2-butyl |
| D-184 | D[1) | CN | H | O-2-ethylhexyl |
| D-185 | D[1) | H | CN | O-2-ethylhexyl |
| D-186 | D[1) | CN | H | $N(CH_3)_2$ |
| D-187 | D[1) | H | CN | $N(CH_3)_2$ |
| D-188 | D[1) | CN | H | $NPh_2$ |
| D-189 | D[1) | H | CN | $NPh_2$ |
| D-190 | F[1) | H | H | H |
| D-191 | F[1) | H | H | $OCH_3$ |
| D-192 | F[1) | H | H | $OCH_2CH_3$ |
| D-193 | F[1) | H | H | O-n-butyl |
| D-194 | F[1) | H | H | O-iso-butyl |
| D-195 | F[1) | H | H | O-2-butyl |
| D-196 | F[1) | H | H | O-2-ethylhexyl |
| D-197 | F[1) | H | H | $N(CH_3)_2$ |
| D-198 | F[1) | H | H | $NPh_2$ |
| D-199 | F[1) | H | $CF_3$ | H |
| D-200 | F[1) | $CF_3$ | H | H |
| D-201 | F[1) | H | $CF_3$ | $OCH_3$ |
| D-202 | F[1) | $CF_3$ | H | $OCH_3$ |
| D-203 | F[1) | H | $CF_3$ | $OCH_2CH_3$ |
| D-204 | F[1) | $CF_3$ | H | $OCH_2CH_3$ |
| D-205 | F[1) | H | $CF_3$ | O-n-butyl |
| D-206 | F[1) | $CF_3$ | H | O-n-butyl |
| D-207 | F[1) | H | $CF_3$ | O-iso-butyl |
| D-208 | F[1) | $CF_3$ | H | O-iso-butyl |
| D-209 | F[1) | H | $CF_3$ | O-2-butyl |
| D-210 | F[1) | $CF_3$ | H | O-2-butyl |
| D-211 | F[1) | H | $CF_3$ | O-2-ethylhexyl |
| D-212 | F[1) | $CF_3$ | H | O-2-ethylhexyl |
| D-213 | F[1) | H | $CF_3$ | $N(CH_3)_2$ |
| D-214 | F[1) | $CF_3$ | H | $N(CH_3)_2$ |
| D-215 | F[1) | H | $CF_3$ | $NPh_2$ |
| D-216 | F[1) | $CF_3$ | H | $NPh_2$ |

-continued

| | | | | |
|---|---|---|---|---|
| D-217 | F[1] | H | CN | H |
| D-218 | F[1] | CN | H | H |
| D-219 | F[1] | CN | H | $OCH_3$ |
| D-220 | F[1] | H | CN | $OCH_3$ |
| D-221 | F[1] | CN | H | $OCH_2CH_3$ |
| D-222 | F[1] | H | CN | $OCH_2CH_3$ |
| D-223 | F[1] | CN | H | O-n-butyl |
| D-224 | F[1] | H | CN | O-n-butyl |
| D-225 | F[1] | CN | H | O-iso-butyl |
| D-226 | F[1] | H | CN | O-iso-butyl |
| D-227 | F[1] | CN | H | O-2-butyl |
| D-228 | F[1] | H | CN | O-2-butyl |
| D-229 | F[1] | CN | H | O-2-ethylhexyl |
| D-230 | F[1] | H | CN | O-2-ethylhexyl |
| D-231 | F[1] | CN | H | $N(CH_3)_2$ |
| D-232 | F[1] | H | CN | $N(CH_3)_2$ |
| D-233 | F[1] | CN | H | $NPh_2$ |
| D-234 | F[1] | H | CN | $NPh_2$ |
| D-235 | E[1] | H | H | H |
| D-236 | E[1] | H | H | $OCH_3$ |
| D-237 | E[1] | H | H | $OCH_2CH_3$ |
| D-238 | E[1] | H | H | O-n-butyl |
| D-239 | E[1] | H | H | O-iso-butyl |
| D-240 | E[1] | H | H | O-2-butyl |
| D-241 | E[1] | H | H | O-2-ethylhexyl |
| D-242 | E[1] | H | H | $N(CH_3)_2$ |
| D-243 | E[1] | H | H | $NPh_2$ |
| D-244 | E[1] | H | $CF_3$ | H |
| D-245 | E[1] | $CF_3$ | H | H |
| D-246 | E[1] | H | $CF_3$ | $OCH_3$ |
| D-247 | E[1] | $CF_3$ | H | $OCH_3$ |
| D-248 | E[1] | H | $CF_3$ | $OCH_2CH_3$ |
| D-249 | E[1] | $CF_3$ | H | $OCH_2CH_3$ |
| D-250 | E[1] | H | $CF_3$ | O-n-butyl |
| D-251 | E[1] | $CF_3$ | H | O-n-butyl |
| D-252 | E[1] | H | $CF_3$ | O-iso-butyl |
| D-253 | E[1] | $CF_3$ | H | O-iso-butyl |
| D-254 | E[1] | H | $CF_3$ | O-2-butyl |
| D-255 | E[1] | $CF_3$ | H | O-2-butyl |
| D-256 | E[1] | H | $CF_3$ | O-2-ethylhexyl |
| D-257 | E[1] | $CF_3$ | H | O-2-ethylhexyl |
| D-258 | E[1] | H | $CF_3$ | $N(CH_3)_2$ |
| D-259 | E[1] | $CF_3$ | H | $N(CH_3)_2$ |
| D-260 | E[1] | H | $CF_3$ | $NPh_2$ |
| D-261 | E[1] | $CF_3$ | H | $NPh_2$ |
| D-262 | E[1] | H | CN | H |
| D-263 | E[1] | CN | H | H |
| D-264 | E[1] | CN | H | $OCH_3$ |
| D-265 | E[1] | H | CN | $OCH_3$ |
| D-266 | E[1] | CN | H | $OCH_2CH_3$ |
| D-267 | E[1] | H | CN | $OCH_2CH_3$ |
| D-268 | E[1] | CN | H | O-n-butyl |
| D-269 | E[1] | H | CN | O-n-butyl |
| D-270 | E[1] | CN | H | O-iso-butyl |
| D-271 | E[1] | H | CN | O-iso-butyl |
| D-272 | E[1] | CN | H | O-2-butyl |
| D-273 | E[1] | H | CN | O-2-butyl |
| D-274 | E[1] | CN | H | O-2-ethylhexyl |
| D-275 | E[1] | H | CN | O-2-ethylhexyl |
| D-276 | E[1] | CN | H | $N(CH_3)_2$ |
| D-277 | E[1] | H | CN | $N(CH_3)_2$ |
| D-278 | E[1] | CN | H | $NPh_2$ |
| D-279 | E[1] | H | CN | $NPh_2$ |
| B-235 | A[1] | $CH_3$ | H | H |
| B-236 | A[1] | H | $CH_3$ | H |
| B-237 | E[1] | $CH_3$ | H | H |
| B-238 | E[1] | H | $CH_3$ | H |
| B-239 | E[1] | H | H | $OCH_3$ |
| B-240 | A[1] | H | H | 2-propoxy |

-continued
| | | | | |
|---|---|---|---|---|
| B-241 | E[1) | H | H | 2-propoxy |
| B-242 | D[1) | H | H | 2-propoxy |
| B-243 | F[1) | CF$_3$ | H | H |
| B-244 | F[1) | H | CF$_3$ | H |
| B-245 | F[1) | H | H | H |
| B-246 | F[1) | H | H | OCH$_3$ |
[1) A = 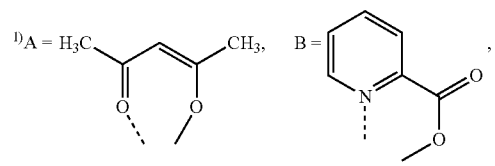, B = 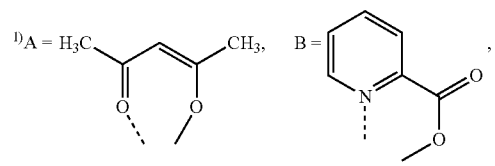,
C = 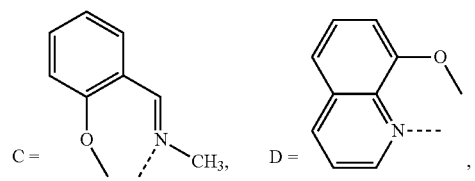, D = 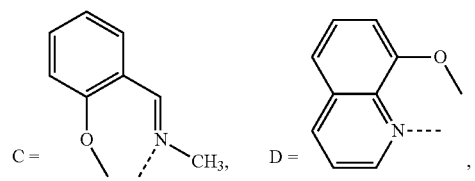,
E = 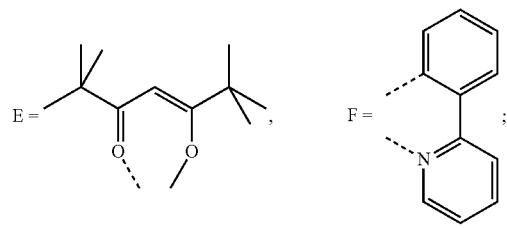, F = 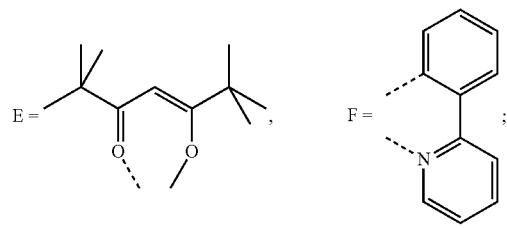;
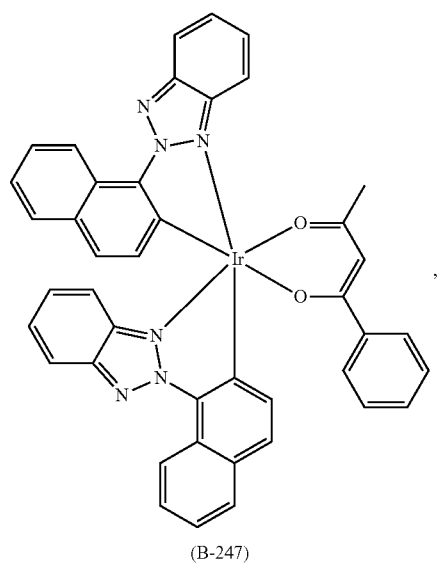
(B-247)

-continued
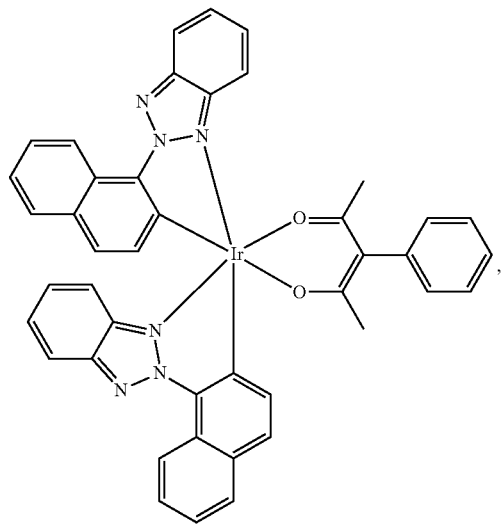
(B-248)
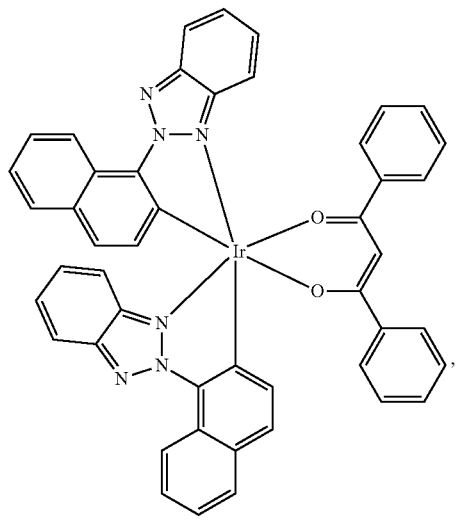
(B-249)
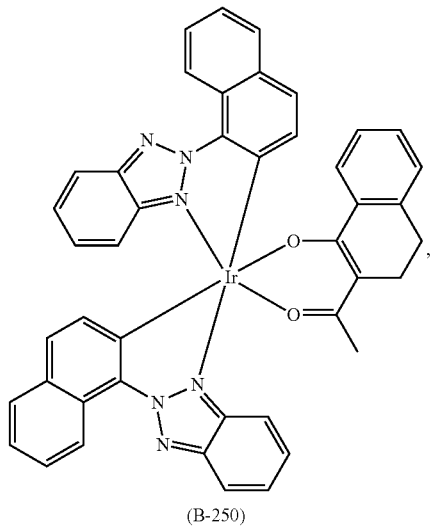
(B-250)

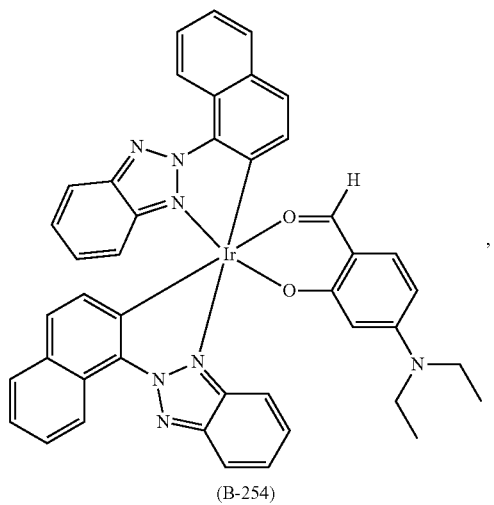
(B-254)
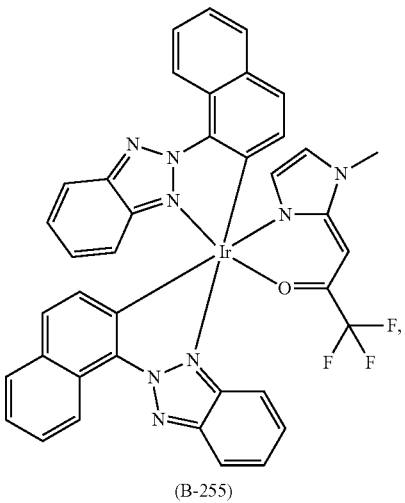
(B-255)
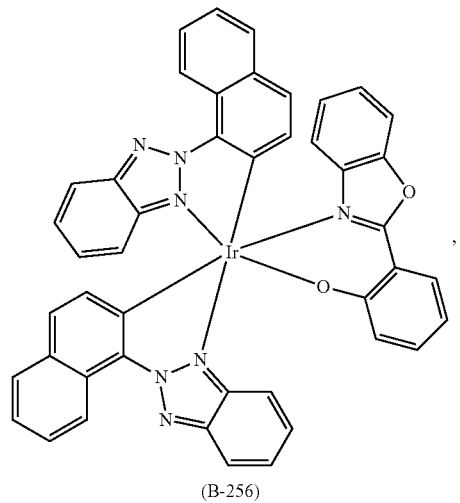
(B-256)

-continued
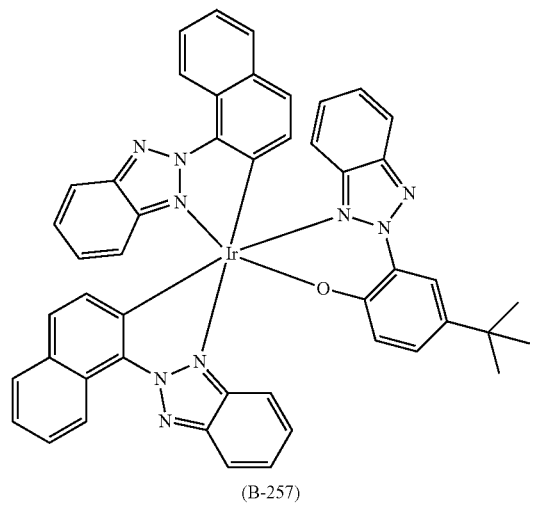
(B-257)
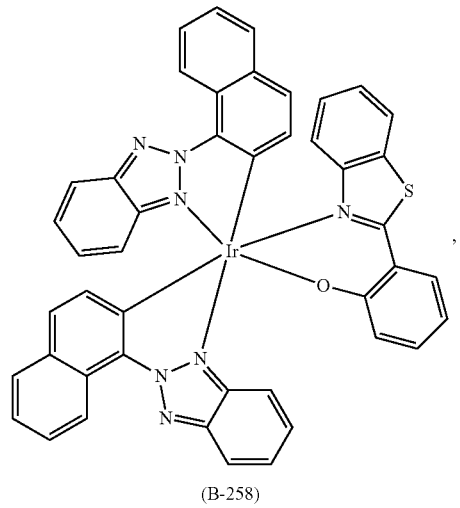
(B-258)
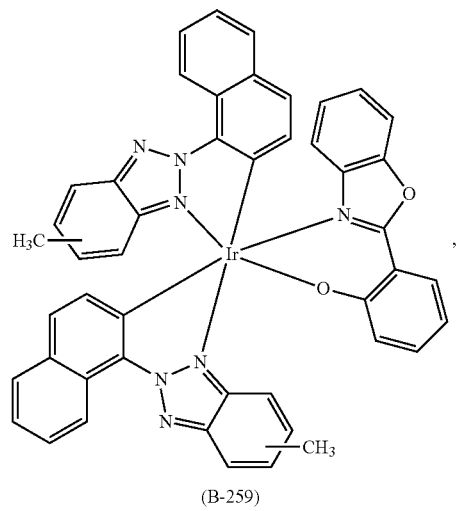
(B-259)

-continued
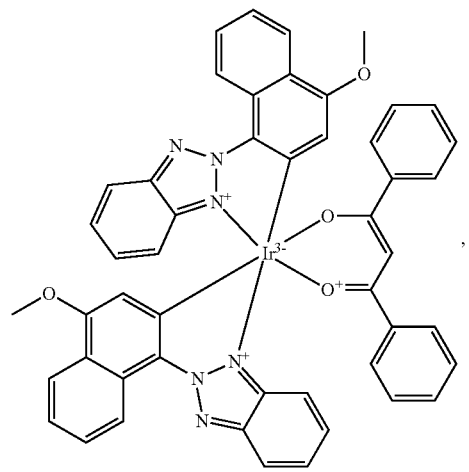
(B-260)
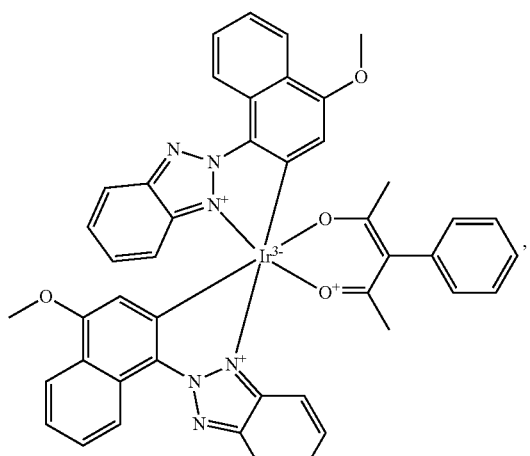
(B-261)
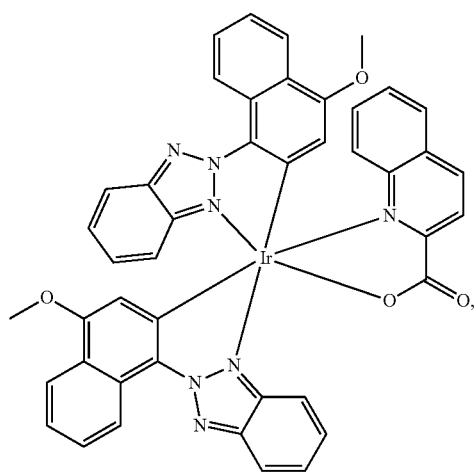
(B-262)

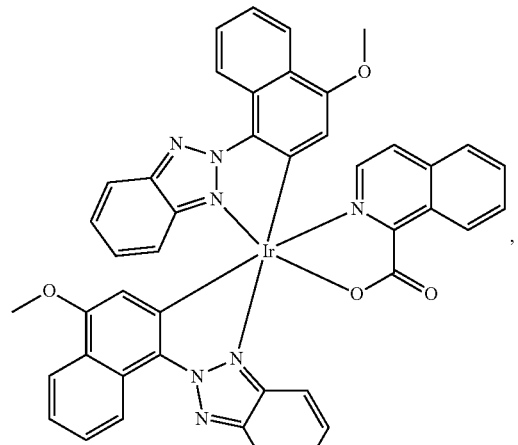
(B-263)
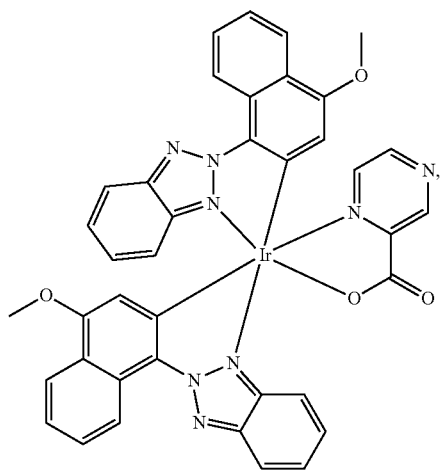
(B-264)
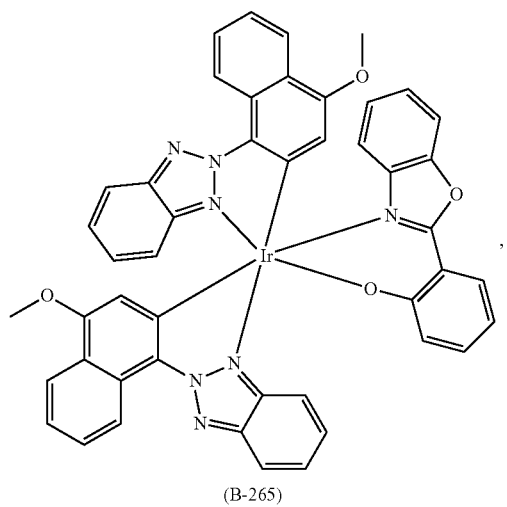
(B-265)

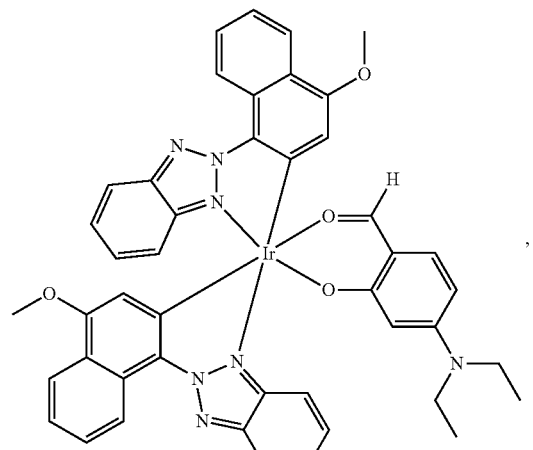
(B-266)
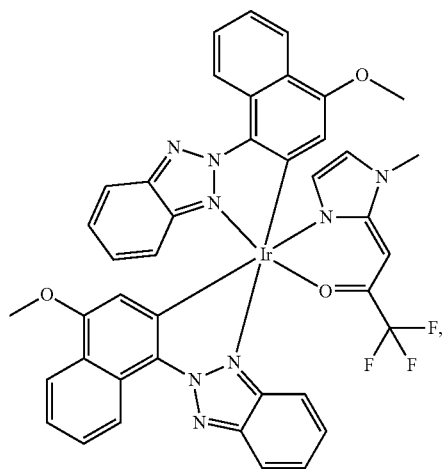
(B-267)
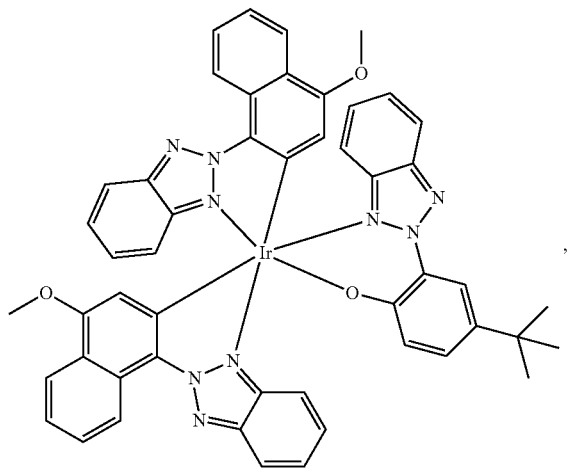
(B-268)

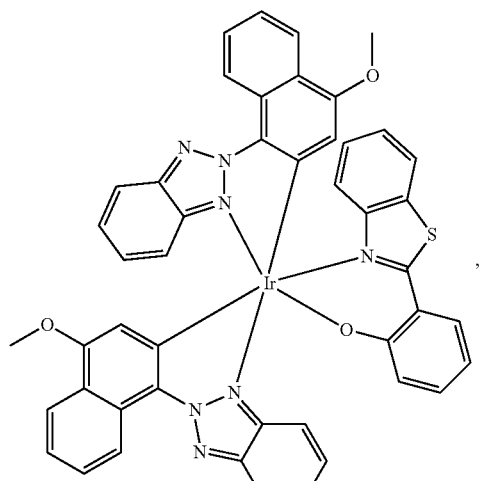
(B-269)
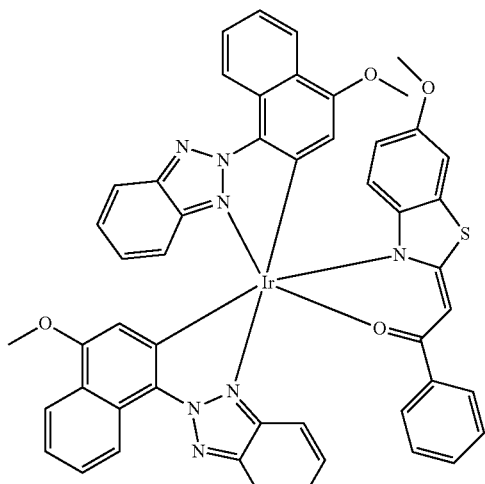
(B-270)
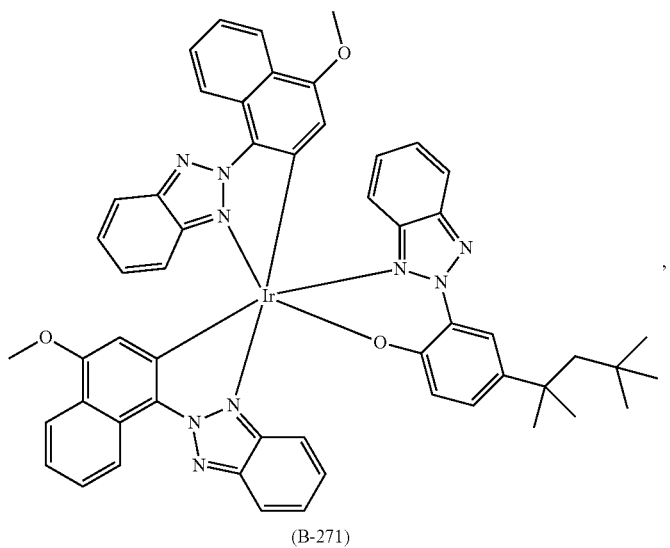
(B-271)

-continued
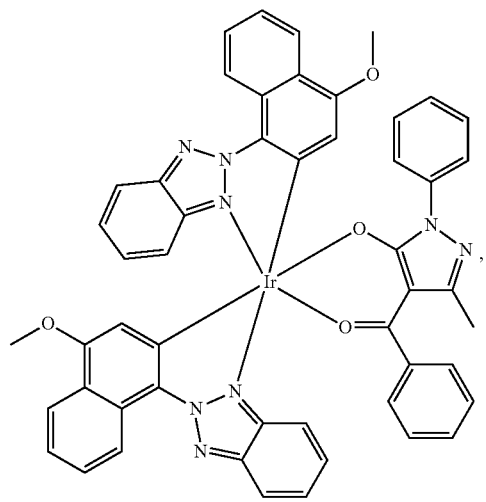
(B-272)
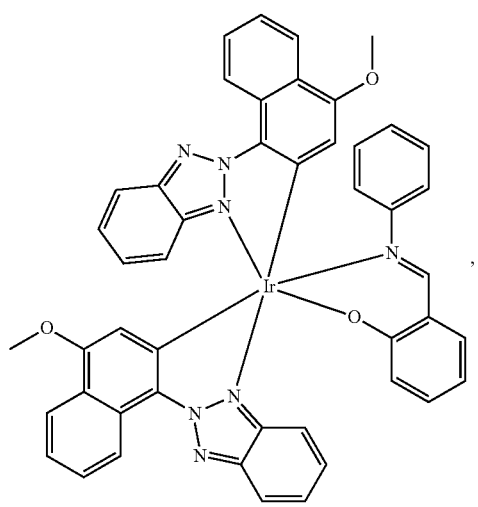
(B-273)
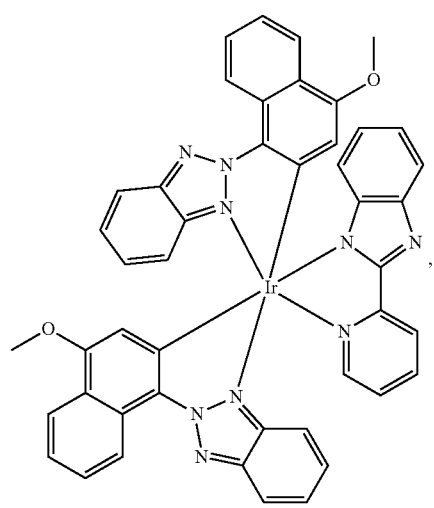
(B-274)

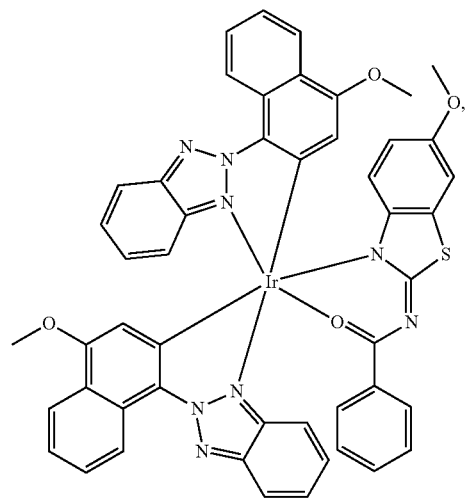
(B-275)
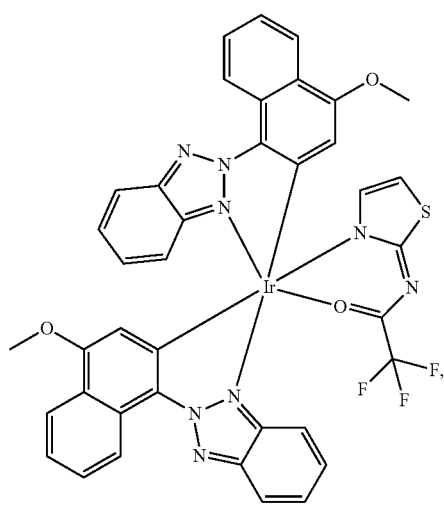
(B-276)
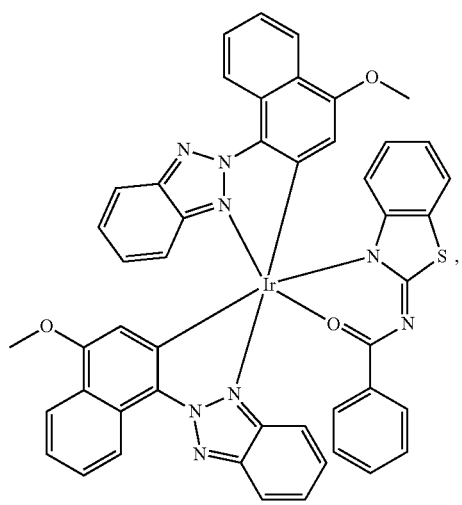
(B-277)

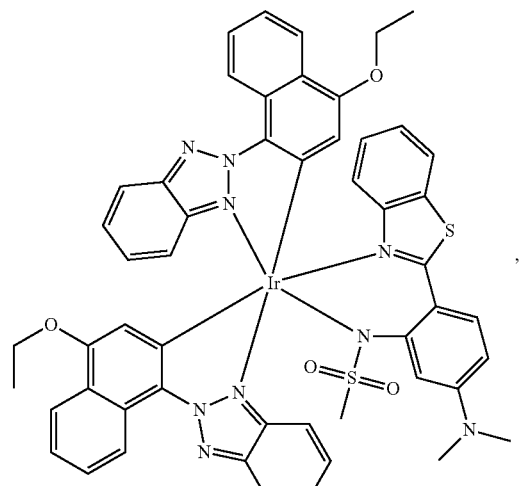
(B-278)
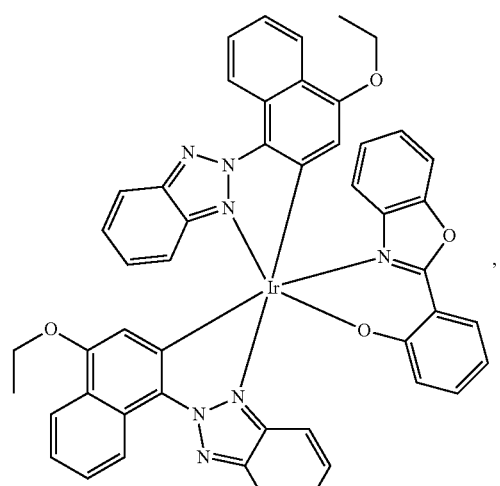
(B-279)
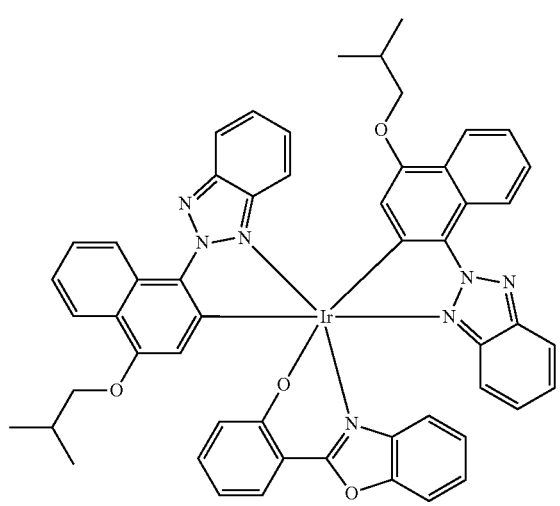
(B-280)

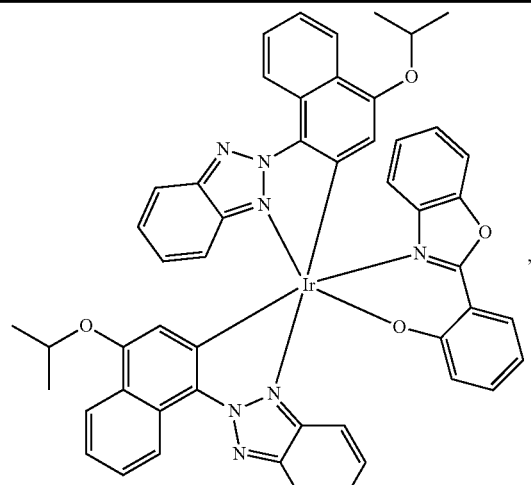
(B-281)
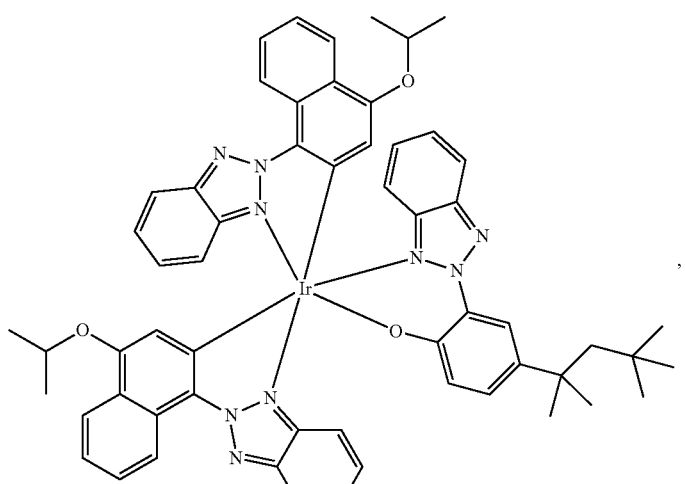
(B-282)
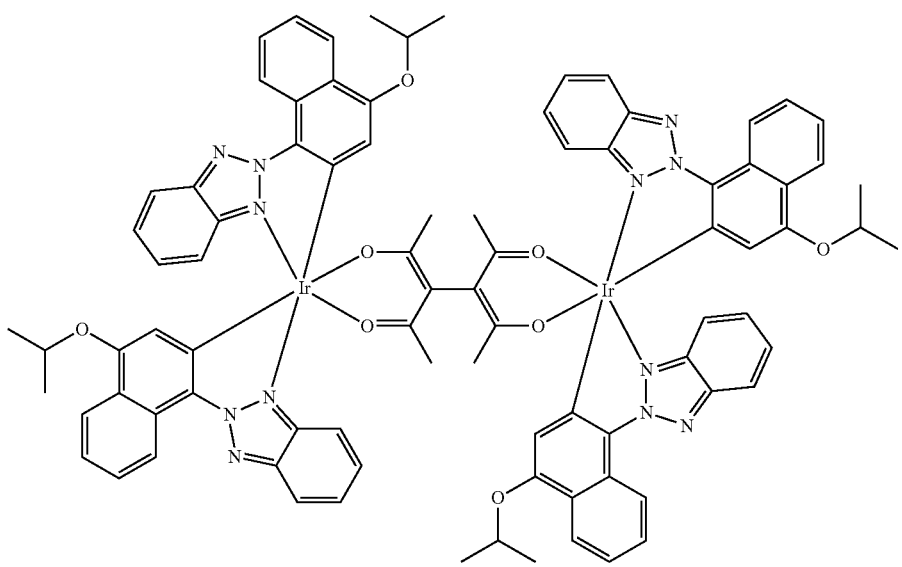
(B-283)

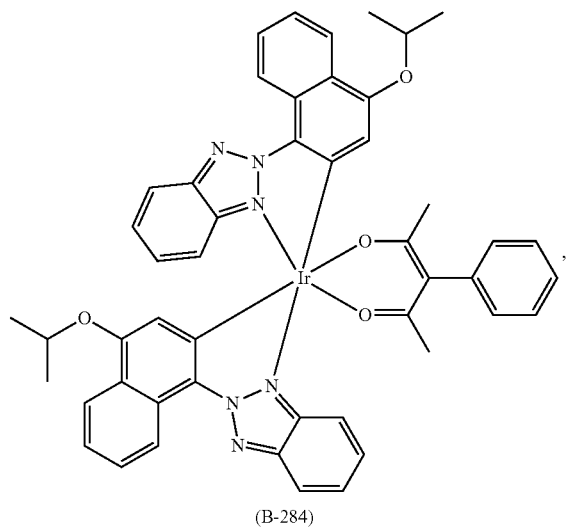
(B-284)
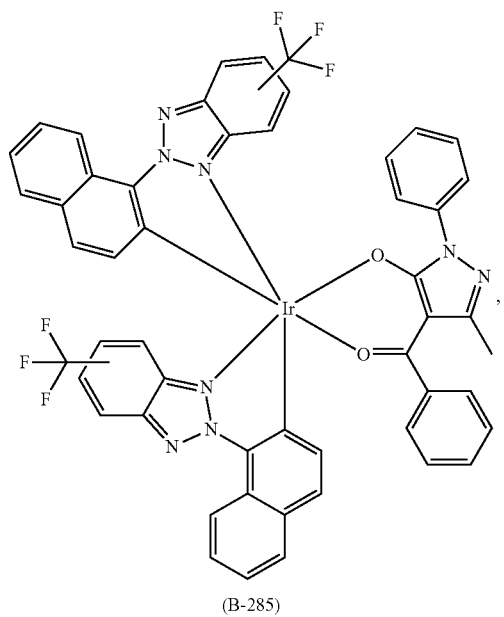
(B-285)

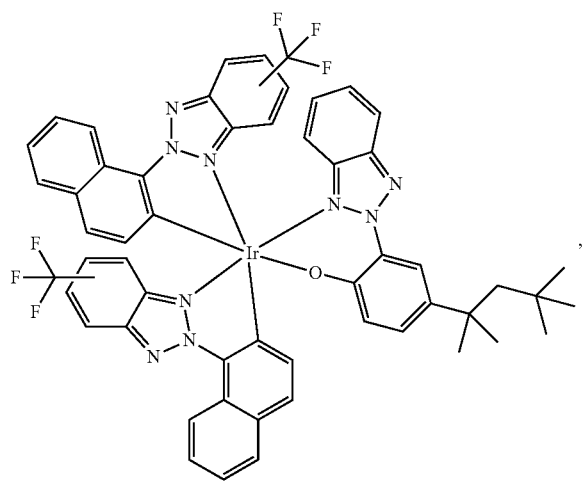
(B-286)
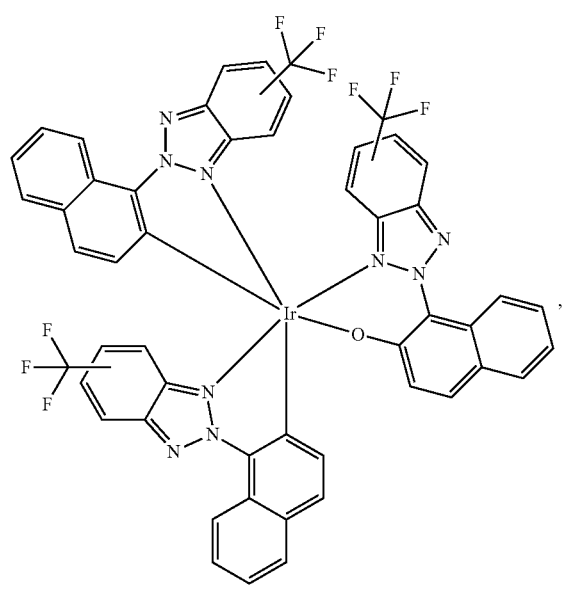
(B-287)

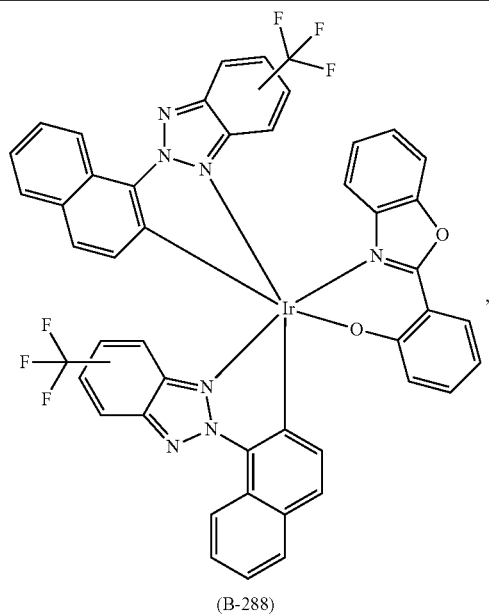
(B-288)
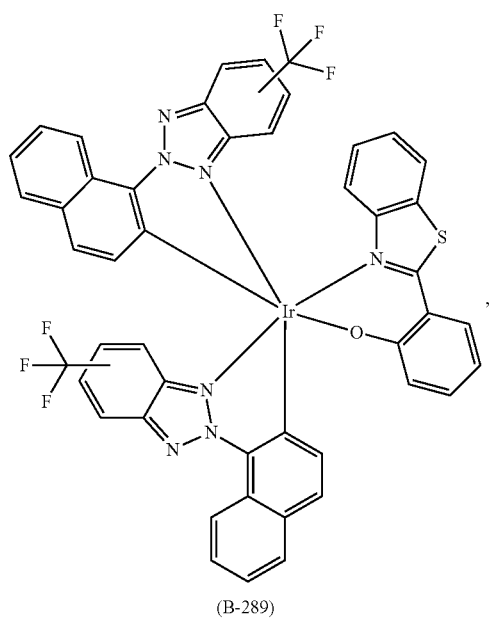
(B-289)
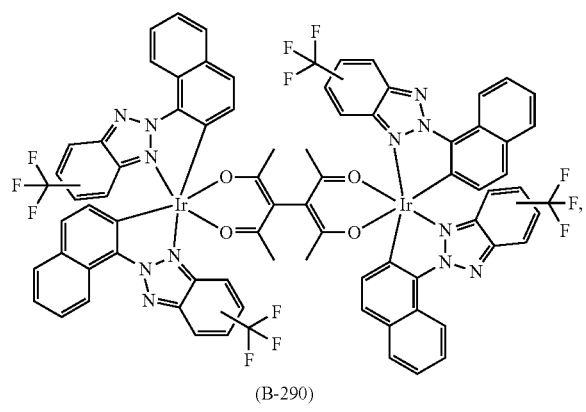
(B-290)

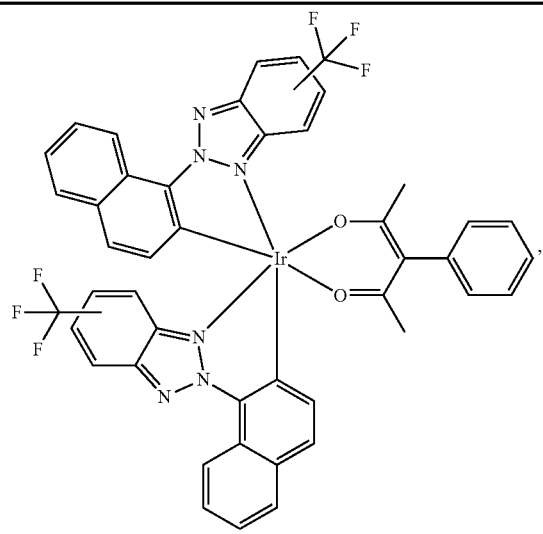
(B-291)
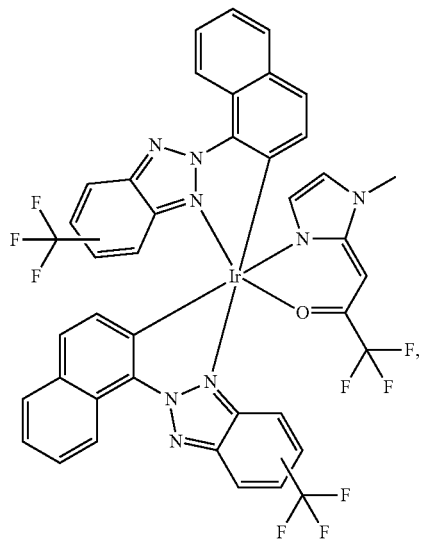
(B-292)
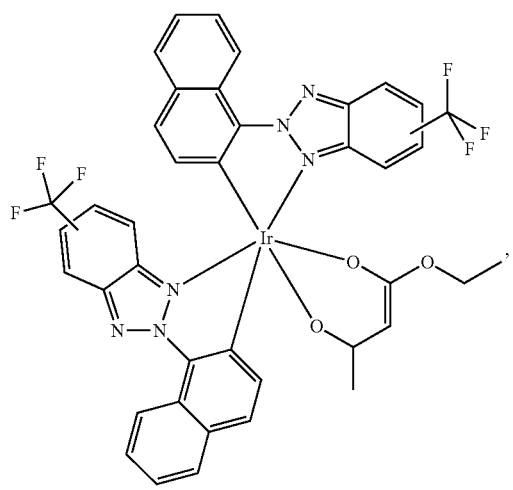
(B-293)

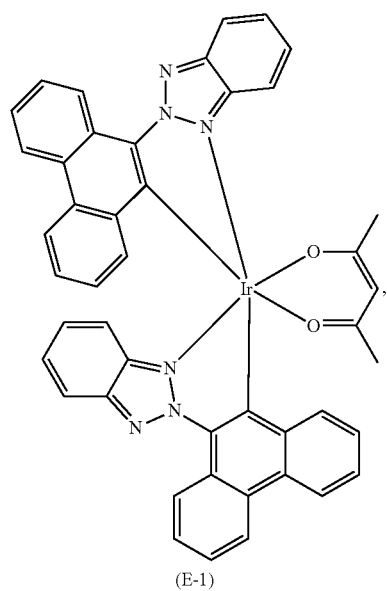
(E-1)
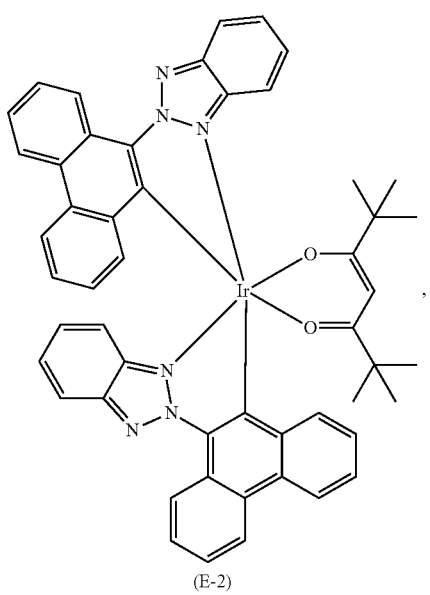
(E-2)

-continued
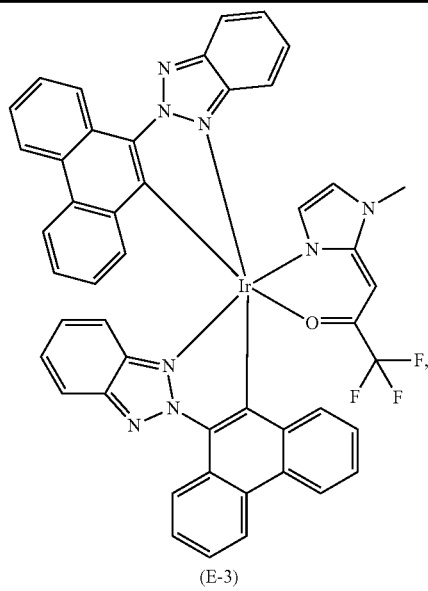
(E-3)
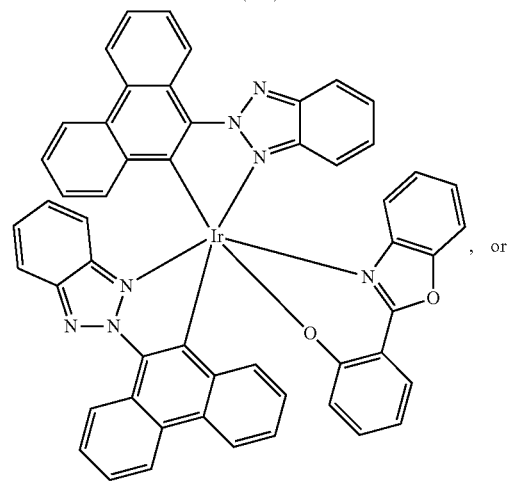
(E-4), or
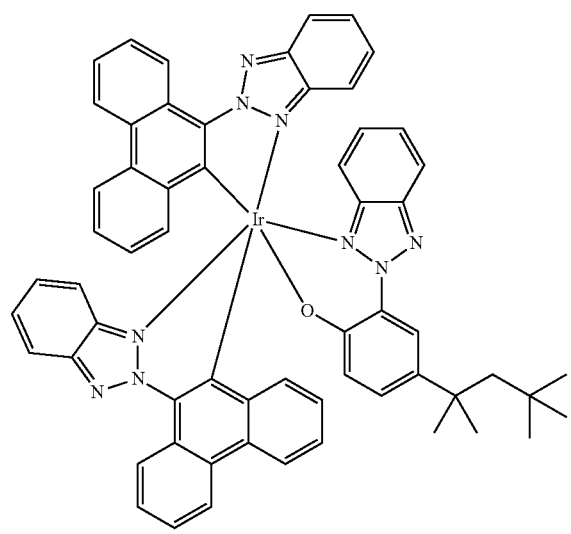
(E-5).

2. An organic electronic device comprising an emitting layer wherein the emitting layer comprises a compound according to claim 1.

3. The device of claim 1, further comprising a hole transport layer selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-di-α-naphthyl-N,N'-diphenyl-4,4'-diphenyldiamine (α-NPD), porphyrinic compounds, and combinations thereof.

4. An organic light emitting diode, oxygen sensitive indicator, phosphorescent indicator or catalyst comprises a compound according to claim 1.

5. The compound of claim 1, having a structure shown below:

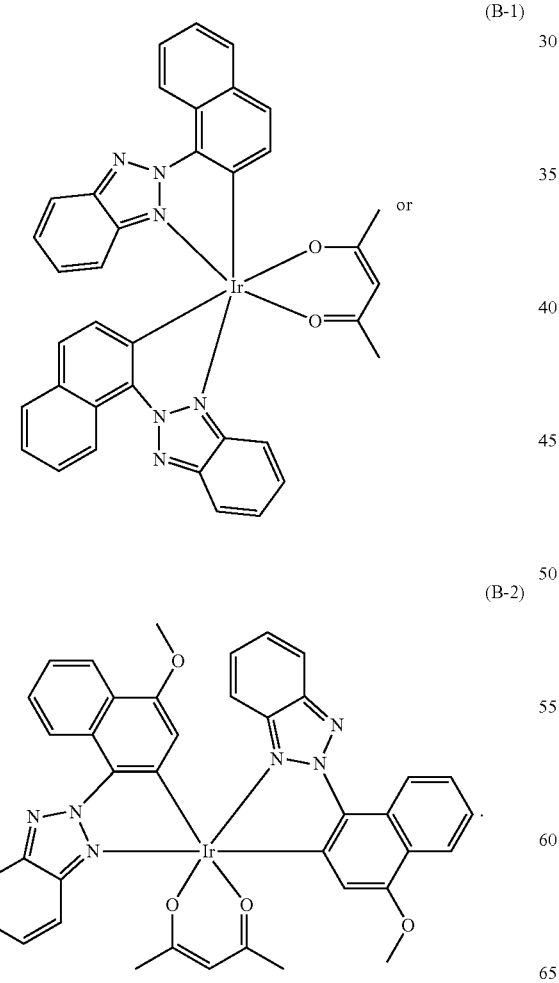

6. A compound of formula (Va), (Vb), (VIIa), or (VIIb) shown below:

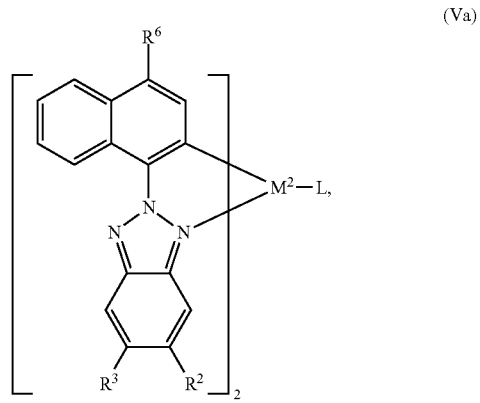

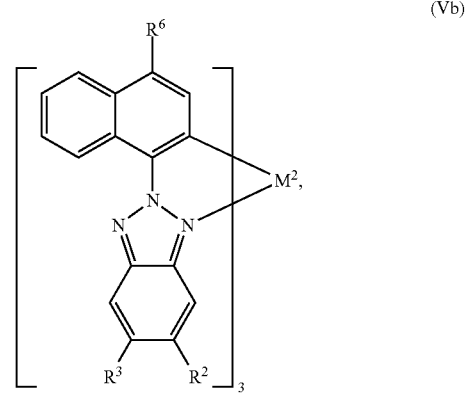

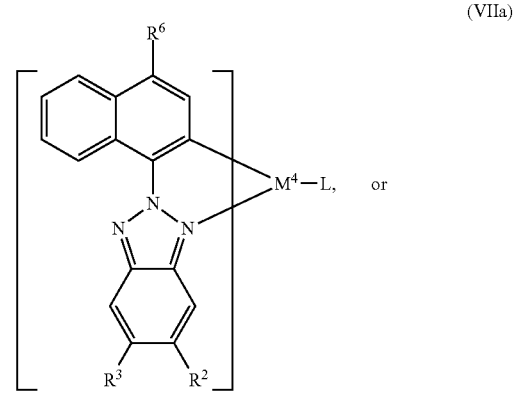

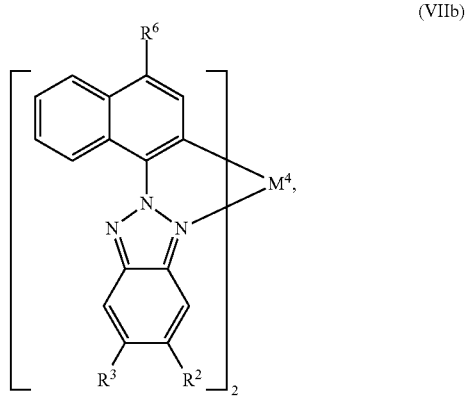

wherein

M² is Rh, Re or Ir,

M⁴ is Pd, or Pt, $R^2$ and $R^3$ are independently of each other H, $C_1$-$C_8$alkyl, $C_1$-$C_8$perfluoroalkyl or CN, $R^6$ is H, —$NR^{25}R^{26}$, or $C_1$-$C_{18}$alkoxy, wherein $R^{25}$ and $R^{26}$ are independently of each other $C_1$-$C_{18}$alkyl, or $C_6$-$C_{10}$aryl, which may be substituted by one, or more groups $C_1$-$C_{18}$alkoxy, or $C_1$-$C_{18}$alkyl, L is a bidentate ligand selected from

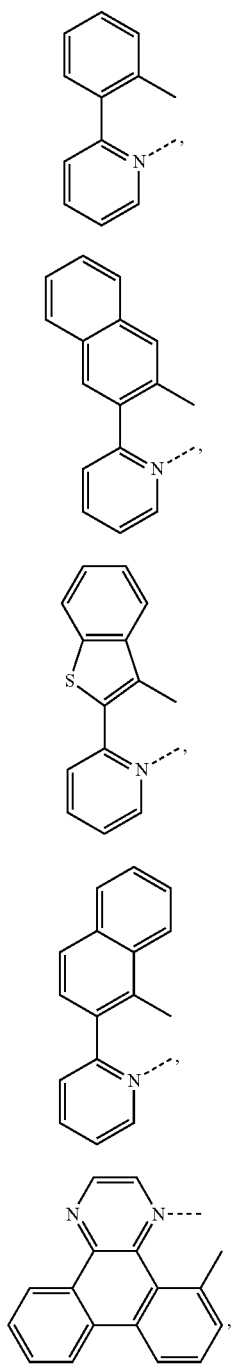

or L is a bidentate ligand L' selected from

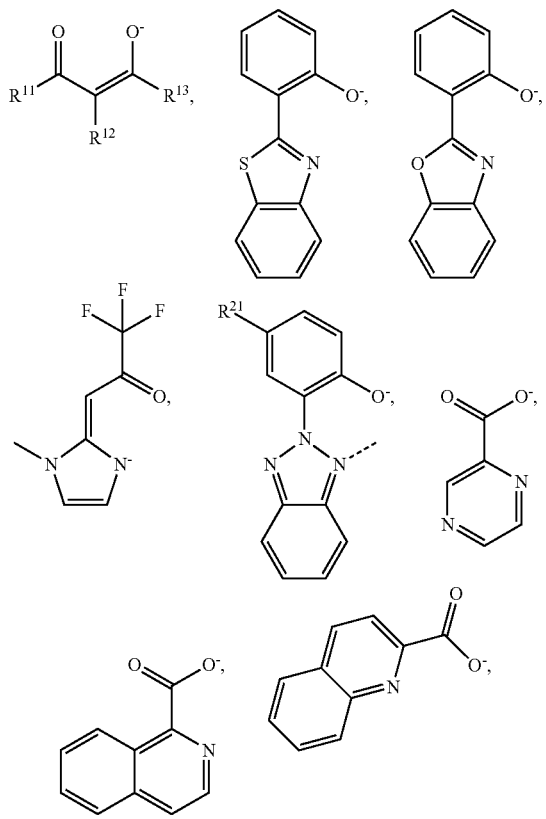

-continued

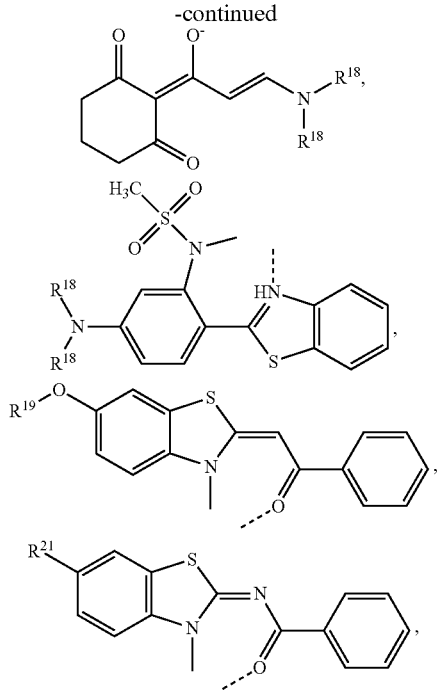

-continued

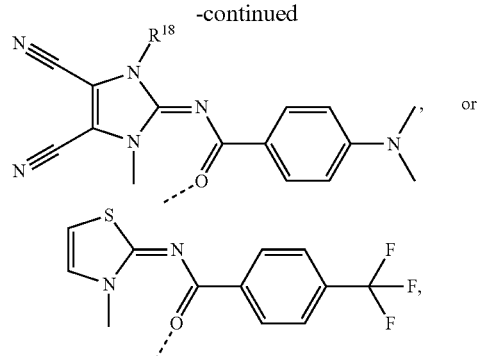

wherein
R$^{11}$ is hydrogen, C$_1$-C$_8$alkyl, C$_6$-C$_{18}$aryl, C$_2$-C$_{10}$heteroaryl, or C$_1$-C$_8$perfluoroalkyl,
R$^{12}$ is hydrogen, C$_6$-C$_{18}$aryl, or C$_1$-C$_8$alkyl, and
R$^{13}$ is hydrogen, C$_1$-C$_8$alkyl, C$_6$-C$_{18}$aryl, C$_2$-C$_{10}$heteroaryl, C$_1$-C$_8$perfluoroalkyl, or C$_1$-C$_8$alkoxy, and
R$^{18}$ is C$_6$-C$_{10}$aryl,
R$^{19}$ is C$_1$-C$_8$alkyl, or C$_1$-C$_8$perfluoroalkyl, and
R$^{21}$ is hydrogen, C$_1$-C$_8$alkyl, or C$_1$-C$_8$alkoxy, which may be partially or fully fluorinated.

* * * * *